US011779640B2

(12) United States Patent
Charneau et al.

(10) Patent No.: US 11,779,640 B2
(45) Date of Patent: Oct. 10, 2023

(54) LENTIVIRAL VECTOR-BASED JAPANESE ENCEPHALITIS IMMUNOGENIC COMPOSITION

(71) Applicants: INSTITUT PASTEUR, Paris (FR); CENTRE NATIONAL DE LA RECHERCHE SCIENTIFIQUE, Paris (FR)

(72) Inventors: Pierre Charneau, Paris (FR); Philippe Despres, Sant-Denis (FR); Melissanne De Wispelaere, Paris (FR); Philippe Souque, Plaisir (FR); Marie-Pascale Frenkiel, Levallois Perret (FR)

(73) Assignees: INSTITUT PASTEUR, Paris (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 16/794,854

(22) Filed: Feb. 19, 2020

(65) Prior Publication Data

US 2020/0230228 A1 Jul. 23, 2020

Related U.S. Application Data

(62) Division of application No. 15/531,157, filed as application No. PCT/EP2015/078891 on Dec. 7, 2015, now Pat. No. 10,603,374.

(30) Foreign Application Priority Data

Dec. 11, 2014 (EP) .................................... 14307008

(51) Int. Cl.

| | |
|---|---|
| ***A61K 39/02*** | (2006.01) |
| ***C07K 14/005*** | (2006.01) |
| ***C12N 7/00*** | (2006.01) |
| ***A61K 39/12*** | (2006.01) |
| ***C12N 15/86*** | (2006.01) |
| ***C07K 14/18*** | (2006.01) |
| ***A61K 9/19*** | (2006.01) |
| ***A61K 47/26*** | (2006.01) |
| *A61K 39/00* | (2006.01) |

(52) U.S. Cl.

CPC ................ *A61K 39/12* (2013.01); *A61K 9/19* (2013.01); *A61K 47/26* (2013.01); *C07K 14/005* (2013.01); *C07K 14/1825* (2013.01); *C12N 7/00* (2013.01); *C12N 15/86* (2013.01); *A61K 2039/5256* (2013.01); *A61K 2039/5258* (2013.01); *A61K 2039/54* (2013.01); *A61K 2039/552* (2013.01); *A61K 2039/575* (2013.01); *C07K 2319/40* (2013.01); *C12N 2740/15043* (2013.01); *C12N 2740/16043* (2013.01); *C12N 2770/24122* (2013.01); *C12N 2770/24123* (2013.01); *C12N 2770/24134* (2013.01); *C12N 2770/24171* (2013.01); *Y02A 50/30* (2018.01)

(58) Field of Classification Search

None

See application file for complete search history.

(56) References Cited

U.S. PATENT DOCUMENTS

2009/0155301 A1* 6/2009 Mason .................. A61K 39/12 424/199.1

FOREIGN PATENT DOCUMENTS

| | | | |
|---|---|---|---|
| CN | 102337248 | A * | 2/2012 |
| JP | 2001510053 | A | 7/2001 |
| WO | 1999/004036 | | 1/1999 |
| WO | 02/081754 | A1 | 10/2002 |
| WO | 2005/023313 | A1 | 3/2005 |
| WO | 2005/065707 | A2 | 7/2005 |
| WO | 2005/111221 | A1 | 11/2005 |
| WO | 2006/010834 | A1 | 2/2006 |
| WO | 2009/019612 | A2 | 2/2009 |
| WO | 2012/103510 | A2 | 8/2012 |
| WO | 2013/033362 | A1 | 8/2012 |
| WO | 2014/016383 | A2 | 1/2014 |

OTHER PUBLICATIONS

Naldini et al., Science, 1996, 272(5259):263-267. (Year: 1996).*
Solomon et al., J. Virology, 2003, 77(5):3091-3098. (Year: 2003).*
Van den Hurk et al., Emerging Infectious Diseases, Nov. 2008, 14(11):1736-1738. (Year: 2008).*
Shaw et al., Biomedicines, 2014, 2:14-35. (Year: 2014).*
Lin et al., Virus Research, 1996, 44:45-56. (Year: 1996).*
English machine translation of CN102337248A (2022) (Year: 2022).*
Luo, et al., "Eliciting broad neutralizing antibody to HIV-1: Envelopes of different lentivirus cross immunization by prime-boost vaccination," Vaccine 30 (2012) 5316-5323.
"The Elementary Study of Developing Nonintegrating Lentiviral Vector", Fang Huang, DOI: 10.7666/d.y1401153, published on Mar. 31, 2009. (English abstract only).
Office Action, Chinese Patent Application No. 2015800758430, dated Sep. 18, 2020.
N. Petrovsky et al: "An Inactivated Cell Culture Japanese Encephalitis Vaccine (JE-ADVAX) Formulated with Delta Inulin Adjuvant Provides Robust Heterologous Protection against West Nile Encephalitis via Cross-Protective Memory B Cells and Neutralizing Antibody", Journaolfvirology, vol. 87, No. 18, Jul. 17, 2013 (Jul. 17, 2013), pp. 10324-1033.

(Continued)

*Primary Examiner* — Stacy B Chen

(74) *Attorney, Agent, or Firm* — Arrigo, Lee, Guttman & Mouta-Bellum LLP

(57) ABSTRACT

The present invention relates to a lentiviral vector-based Japanese encephalitis (JE) immunogenic composition. The present invention is directed to a recombinant lentiviral vector expressing the precursor of membrane (prM) and the envelope (E) protein, in particular glycoprotein of a Japanese encephalitis virus (JEV) or immunogenic fragments thereof. The present invention also provides cells expressing the lentiviral vector, uses and methods to prevent a JEV infection in a mammalian host, especially in a human or an animal host, in particular a pig or a piglet, preferably a domestic pig or a domestic piglet.

17 Claims, 7 Drawing Sheets

Specification includes a Sequence Listing.

(56) References Cited

OTHER PUBLICATIONS

Erra Elina O et al: "Cross-protection elicited by primary and booster vaccinations against Japanese encephalitis: A two-year follow-up study" Vaccine, vol. 32, No. 1, Oct. 28, 2013 (Oct. 28, 2013), pp. 119-123.
Sasaki O et al: "Protection of pigs against mosquito-borne japanese encephalitis virus by immunization with a live attenuated vaccine," Antivirarlesearch Elsevier BV,NL, vol. 2, No. 6, Dec. 1982 (Dec. 1982), pp. 355-360.

* cited by examiner

SEQUENCE LISTING

<160> NUMBER OF SEQ ID NOS: 41

<210> SEQ ID NO 1
<211> LENGTH: 69
<212> TYPE: DNA
<213> ORGANISM: Artificial Sequence
<220> FEATURE:
<223> OTHER INFORMATION: native nucleotide sequence of the polynucleotide encoding the signal peptide for prM.

<400> SEQUENCE: 1
atgggaggaa atgaaggctc aatcatgtgg ctcgcgagct tggcagttgt catagcttgt 60
gcaggagcc 69

<210> SEQ ID NO 2
<211> LENGTH: 69
<212> TYPE: DNA
<213> ORGANISM: Artificial Sequence
<220> FEATURE:
<223> OTHER INFORMATION: codon-optimized nucleotide sequence of the polynucleotide encoding the signal peptide for prM.

<400> SEQUENCE: 2
atgggcggaa acgaagggtc cattatgtgg ctcgcctccc tggccgtggt gatcgcctgc 60
gccggagca 69

<210> SEQ ID NO 3
<211> LENGTH: 23
<212> TYPE: PRT
<213> ORGANISM: Artificial Sequence
<220> FEATURE:
<223> OTHER INFORMATION: signal peptide for prM.

<400> SEQUENCE: 3

Met Gly Gly Asn Glu Gly Ser Ile Met Trp Leu Ala Ser Leu Ala Val
1 5 10 15

Val Ile Ala Cys Ala Gly Ala
20

<210> SEQ ID NO 4
<211> LENGTH: 501
<212> TYPE: DNA
<213> ORGANISM: Artificial Sequence
<220> FEATURE:
<223> OTHER INFORMATION: native nucleotide sequence of the polynucleotide encoding the full-length prM protein.

<400> SEQUENCE: 4
atgaagttgt caaatttcca ggggaagctt ttgatgacca ttaacaacac ggacattgca 60
gacgttatcg tgattcccac ctcaaaagga gagaacagat gctgggtccg ggcaatcgac 120
gtcggctaca tgtgtgagga cactatcacg tacgaatgtc ctaagcttac catgggcaat 180
gatccagagg atgtggattg ctggtgtgac aaccaagaag tctacgtcca atatggacgg 240
tgcacgcgga ccagacattc caagcgaagc aggagatccg tgtcggtcca aacacatggg 300
gagagttcac tagtgaataa aaaagaggct tggctggatt caacgaaagc cacacgatat 360
ctcatgaaaa ctgagaactg gatcataagg aatcctggct atgctttcct ggcggcggta 420
cttggctgga tgcttggcag taacaacggt caacgcgtgg tattcaccat cctcctgctg 480
ctggttgctc cggcttacag t 501

<210> SEQ ID NO 5

<211> LENGTH: 501
<212> TYPE: DNA
<213> ORGANISM: Artificial Sequence
<220> FEATURE:
<223> OTHER INFORMATION: codon-optimized nucleotide sequence of the polynucleotide encoding the full-length prM protein.

<400> SEQUENCE: 5

```
atgaagctgt ccaactttca ggggaagctg ctcatgacaa ttaacaacac tgatattgcc     60

gatgtcattg tcatccctac atccaagggc gaaaaccggt gctgggtccg ggccatcgac    120

gtcgggtaca tgtgcgaaga taccattaca tacgaatgcc ccaagctgac catgggaaac    180

gatcctgagg acgtggattg ctggtgcgac aaccaggagg tgtacgtgca gtacgggcgg    240

tgcacaagga cacggcactc caagcgctct cggcggagcg tgtccgtgca gacccacggc    300

gagtcttctc tcgtcaacaa gaaggaggca tggctggata gcactaaggc cacccgctac    360

ctcatgaaga ctgagaactg gatcattcgg aaccctggat acgcttttct ggctgccgtg    420

ctggggtgga tgctggggag caacaacgga cagcgcgtgg tcttcaccat tcttctcttg    480

ttggtcgctc ctgcttacag c                                              501
```

<210> SEQ ID NO 6
<211> LENGTH: 167
<212> TYPE: PRT
<213> ORGANISM: Artificial Sequence
<220> FEATURE:
<223> OTHER INFORMATION: full-length prM protein.

<400> SEQUENCE: 6

```
Met Lys Leu Ser Asn Phe Gln Gly Lys Leu Leu Met Thr Ile Asn Asn
1               5                   10                  15

Thr Asp Ile Ala Asp Val Ile Val Ile Pro Thr Ser Lys Gly Glu Asn
            20                  25                  30

Arg Cys Trp Val Arg Ala Ile Asp Val Gly Tyr Met Cys Glu Asp Thr
        35                  40                  45

Ile Thr Tyr Glu Cys Pro Lys Leu Thr Met Gly Asn Asp Pro Glu Asp
    50                  55                  60

Val Asp Cys Trp Cys Asp Asn Gln Glu Val Tyr Val Gln Tyr Gly Arg
65                  70                  75                  80

Cys Thr Arg Thr Arg His Ser Lys Arg Ser Arg Arg Ser Val Ser Val
                85                  90                  95

Gln Thr His Gly Glu Ser Ser Leu Val Asn Lys Lys Glu Ala Trp Leu
            100                 105                 110

Asp Ser Thr Lys Ala Thr Arg Tyr Leu Met Lys Thr Glu Asn Trp Ile
        115                 120                 125

Ile Arg Asn Pro Gly Tyr Ala Phe Leu Ala Ala Val Leu Gly Trp Met
    130                 135                 140

Leu Gly Ser Asn Asn Gly Gln Arg Val Val Phe Thr Ile Leu Leu Leu
145                 150                 155                 160

Leu Val Ala Pro Ala Tyr Ser
                165
```

<210> SEQ ID NO 7
<211> LENGTH: 1500
<212> TYPE: DNA
<213> ORGANISM: Artificial Sequence
<220> FEATURE:
<223> OTHER INFORMATION: native nucleotide sequence of the polynucleotide encoding the full-length E protein.

<400> SEQUENCE: 7
tttaattgtc tgggaatggg caatcgtgac ttcatagaag gagccagtgg agccacttgg 60
gtggacttgg tgctagaagg agatagctgc ttgacaatta tggcaaacga caaaccaaca 120
ttggacgtcc gcatgatcaa catcgaagct agccaacttg ctgaggtcag aagttactgt 180
tatcatgctt cagtcactga catctcgacg gtggctcggt gccccacgac tggagaagcc 240
cacaacgaga agcgagctga tagtagctat gtgtgcaaac aaggcttcac tgatcgtggg 300
tggggcaacg gatgtggact tttcgggaag ggaagcattg acacatgtgc aaaattctcc 360
tgcaccagta aagcgattgg gagaacaatc cagccagaaa acatcaaata cgaagttggc 420
atttttgtgc atggaaccac cacttcggaa aaccatggga attattcagc gcaagttggg 480
gcgtcccagg cggcaaagtt tacagtaaca cccaatgctc cttcgataac cctcaaactt 540
ggtgactacg gagaagtcac actggactgt gagccaagga gtggactgaa cactgaagcg 600
ttttacgtca tgaccgtggg gtcaaagtca tttctggtcc atagggaatg gtttcatgac 660
ctcgctctcc cctggacgtc cccttcgagc acagcgtgga gaaacagaga actcctcatg 720
gagtttgaag aggcgcacgc cacaaaacag tccgttgttg ctcttgggtc acaggaagga 780
ggcctccatc aggcgttggc aggagccatc gtggtggagt actcaagctc agtgaagtta 840
acatcaggcc acctgaaatg taggctgaaa atggacaaac tggctctgaa aggcacaacc 900
tatggcatgt gcacagaaaa attctcgttc gcaaaaaatc cggcggacac tggtcacgga 960
acagttgtca tcgaactctc ctactctggg agtgatggcc cctgcaaaat tccgattgtc 1020
tccgttgcga gcctcaatga catgaccccc gttgggcggc tggtgacagt gaaccccttc 1080
gtcgcgactt ccagtgccaa ttcaaaggtg ctggtcgaga tggaaccccc cttcggagac 1140
tcctacatcg tagttggaag gggagacaag cagatcaacc accattggca caaagctgga 1200
agcacgctgg gcaaagcctt ttcaacaact ttgaagggag ctcagagact ggcagcgttg 1260
ggtgacacag cctgggactt tggctccatt ggaggggtct tcaactccat aggaaaagcc 1320
gttcaccaag tgtttggtgg tgccttcaga acactctttg gggaatgtc ttggatcaca 1380 caagggctaa tgggtgccct actactctgg atgggcgtca acgcacgaga ccgatcaatt 1440
gctttggcct tcttagccac aggaggtgtg ctcgtgttct tagcgaccaa tgtgcatgct 1500

<210> SEQ ID NO 8
<211> LENGTH: 1500
<212> TYPE: DNA
<213> ORGANISM: Artificial Sequence
<220> FEATURE:
<223> OTHER INFORMATION: codon-optimized nucleotide sequence of the
      polynucleotide encoding the full-length E protein.

<400> SEQUENCE: 8
tttaactgct tgggcatggg caacagggat ttcatcgagg gcgcctccgg ggcaacctgg 60
gtggatttgg tgctcgaagg agacagctgc ctcaccatca tggccaacga caagcccacc 120
ctcgacgtga ggatgatcaa catcgaggct tcccaactgg ccgaggtcag aagctactgt 180
taccatgcca gcgtgacaga tatttccaca gtggctaggt gcccaactac aggcgaggcc 240
cacaacgaga aaagggctga tagtagctat gtctgtaaac agggctttac cgatcggggg 300
tggggcaacg ggtgtgggct gttcgggaag gggtccattg atacctgtgc taagttcagt 360
tgcacttcca aggccatcgg caggacaatt cagcctgaga atattaagta cgaggtcggc 420
atctttgtgc acgggacaac cacaagcgag aaccacggga actactccgc tcaagtgggc 480

-continued gccagccagg ccgccaagtt tacagtgact cccaacgccc ccagtattac tctgaagctg 540
ggagactatg gcgaggtgac cctggattgc gagcccagat ccggcctgaa caccgaggct 600
ttttacgtga tgacagtcgg ctccaagagt ttcttggtgc acagggagtg gtttcacgac 660
ctcgctctcc cctggacaag cccctcctca actgcttgga gaaacagaga gctcctgatg 720
gagttcgaag aggctcatgc cactaagcag agcgtcgtgg cattggggag tcaggaaggc 780
ggactccacc aggcccttgc cggagccatc gtggtcgagt acagctcaag cgtgaagttg 840
accagtggac acctgaagtg tagactgaag atggacaaac tggctctgaa ggggacaaca 900
tacggcatgt gcaccgagaa gttcagcttc gccaaaaatc ccgcagacac cgggcatggg 960
acagtcgtca tcgagcttag ctacagcggc tccgacggac catgcaagat tccaattgtg 1020
agcgtggcct ctctcaacga tatgactccc gtgggccggc tggtgactgt gaacccattc 1080
gtggccactt ccagcgctaa cagcaaggtg ttggtggaga tggagccacc tttcggggac 1140
agctatattg tggtggggcg gggagacaaa cagatcaacc atcattggca caaggccggg 1200
tcaacactcg gcaaggcctt ttcaacaact ctcaagggag cccagagact ggccgccctc 1260
ggcgacacag cctgggattt cgggtcaatc ggcggggtgt tcaactcaat cgggaaggct 1320
gtccaccagg tgttcggcgg agcctttcgg accctgtttg gggaatgtc ttggattact 1380 caggggctga tgggggctct gcttctttgg atgggcgtca acgcccggga caggagtatc 1440
gctctggctt tcctggccac aggcggggtg ctcgtgtttc tggctaccaa tgtccatgct 1500

<210> SEQ ID NO 9
<211> LENGTH: 500
<212> TYPE: PRT
<213> ORGANISM: Artificial Sequence
<220> FEATURE:
<223> OTHER INFORMATION: full-length E protein.

<400> SEQUENCE: 9

Phe Asn Cys Leu Gly Met Gly Asn Arg Asp Phe Ile Glu Gly Ala Ser
1 5 10 15

Gly Ala Thr Trp Val Asp Leu Val Leu Glu Gly Asp Ser Cys Leu Thr
20 25 30

Ile Met Ala Asn Asp Lys Pro Thr Leu Asp Val Arg Met Ile Asn Ile
35 40 45

Glu Ala Ser Gln Leu Ala Glu Val Arg Ser Tyr Cys Tyr His Ala Ser
50 55 60

Val Thr Asp Ile Ser Thr Val Ala Arg Cys Pro Thr Thr Gly Glu Ala
65 70 75 80

His Asn Glu Lys Arg Ala Asp Ser Ser Tyr Val Cys Lys Gln Gly Phe
85 90 95

Thr Asp Arg Gly Trp Gly Asn Gly Cys Gly Leu Phe Gly Lys Gly Ser
100 105 110

Ile Asp Thr Cys Ala Lys Phe Ser Cys Thr Ser Lys Ala Ile Gly Arg
115 120 125

Thr Ile Gln Pro Glu Asn Ile Lys Tyr Glu Val Gly Ile Phe Val His
130 135 140

Gly Thr Thr Thr Ser Glu Asn His Gly Asn Tyr Ser Ala Gln Val Gly
145 150 155 160

Ala Ser Gln Ala Ala Lys Phe Thr Val Thr Pro Asn Ala Pro Ser Ile
165 170 175

Thr Leu Lys Leu Gly Asp Tyr Gly Glu Val Thr Leu Asp Cys Glu Pro
180 185 190

-continued

```
Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Ser Ile Gly Lys Ala Val His Gln Val Phe Gly Gly Ala
        435                 440                 445

Phe Arg Thr Leu Phe Gly Gly Met Ser Trp Ile Thr Gln Gly Leu Met
    450                 455                 460

Gly Ala Leu Leu Leu Trp Met Gly Val Asn Ala Arg Asp Arg Ser Ile
465                 470                 475                 480

Ala Leu Ala Phe Leu Ala Thr Gly Gly Val Leu Val Phe Leu Ala Thr
                485                 490                 495

Asn Val His Ala
            500
```

<210> SEQ ID NO 10
<211> LENGTH: 1356
<212> TYPE: DNA
<213> ORGANISM: Artificial Sequence
<220> FEATURE:
<223> OTHER INFORMATION: native nucleotide sequence of the polynucleotide encoding the soluble form of the E protein lacking the two C-terminal transmembrane domains (EdeltaTM).

<400> SEQUENCE: 10

```
tttaattgtc tgggaatggg caatcgtgac ttcatagaag gagccagtgg agccacttgg      60

gtggacttgg tgctagaagg agatagctgc ttgacaatta tggcaaacga caaaccaaca     120

ttggacgtcc gcatgatcaa catcgaagct agccaacttg ctgaggtcag aagttactgt     180
```

-continued

```
tatcatgctt cagtcactga catctcgacg gtggctcggt gccccacgac tggagaagcc    240
cacaacgaga agcgagctga tagtagctat gtgtgcaaac aaggcttcac tgatcgtggg    300
tggggcaacg gatgtggact tttcgggaag ggaagcattg acacatgtgc aaaattctcc    360
tgcaccagta aagcgattgg gagaacaatc cagccagaaa acatcaaata cgaagttggc    420
atttttgtgc atggaaccac cacttcggaa aaccatggga attattcagc gcaagttggg    480
gcgtcccagg cggcaaagtt tacagtaaca cccaatgctc cttcgataac cctcaaactt    540
ggtgactacg gagaagtcac actggactgt gagccaagga gtggactgaa cactgaagcg    600
ttttacgtca tgaccgtggg gtcaaagtca tttctggtcc atagggaatg gtttcatgac    660
ctcgctctcc cctggacgtc cccttcgagc acagcgtgga gaaacagaga actcctcatg    720
gagtttgaag aggcgcacgc cacaaaacag tccgttgttg ctcttgggtc acaggaagga    780
ggcctccatc aggcgttggc aggagccatc gtggtggagt actcaagctc agtgaagtta    840
acatcaggcc acctgaaatg taggctgaaa atggacaaac tggctctgaa aggcacaacc    900
tatggcatgt gcacagaaaa attctcgttc gcaaaaaatc cggcggacac tggtcacgga    960
acagttgtca tcgaactctc ctactctggg agtgatggcc cctgcaaaat tccgattgtc   1020
tccgttgcga gcctcaatga catgaccccc gttgggcggc tggtgacagt gaacccettc   1080
gtcgcgactt ccagtgccaa ttcaaaggtg ctggtcgaga tggaaccccc cttcggagac   1140
tcctacatcg tagttggaag gggagacaag cagatcaacc accattggca caaagctgga   1200
agcacgctgg gcaaagcctt ttcaacaact ttgaagggag ctcagagact ggcagcgttg   1260
ggtgacacag cctgggactt tggctccatt ggaggggtct tcaactccat aggaaaagcc   1320
gttcaccaag tgtttggtgg tgccttcaga acactc                             1356
```

<210> SEQ ID NO 11
<211> LENGTH: 1356
<212> TYPE: DNA
<213> ORGANISM: Artificial Sequence
<220> FEATURE:
<223> OTHER INFORMATION: codon-optimized nucleotide sequence of the polynucleotide encoding the soluble form of the E protein lacking the two C-terminal transmembrane domains (EdeltaTM).

<400> SEQUENCE: 11

```
tttaactgct tgggcatggg caacagggat ttcatcgagg gcgcctccgg ggcaacctgg     60
gtggatttgg tgctcgaagg agacagctgc ctcaccatca tggccaacga caagcccacc    120
ctcgacgtga ggatgatcaa catcgaggct tcccaactgg ccgaggtcag aagctactgt    180
taccatgcca gcgtgacaga tatttccaca gtggctaggt gcccaactac aggcgaggcc    240
cacaacgaga aaagggctga tagtagctat gtctgtaaac agggctttac cgatcggggg    300
tggggcaacg ggtgtgggct gttcgggaag gggtccattg atacctgtgc taagttcagt    360
tgcacttcca aggccatcgg caggacaatt cagcctgaga atattaagta cgaggtcggc    420
atctttgtgc acgggacaac cacaagcgag aaccacggga actactccgc tcaagtgggc    480
gccagccagg ccgccaagtt tacagtgact cccaacgccc ccagtattac tctgaagctg    540
ggagactatg gcgaggtgac cctggattgc gagcccagat ccggcctgaa caccgaggct    600
ttttacgtga tgacagtcgg ctccaagagt ttcttggtgc acagggagtg gtttcacgac    660
ctcgctctcc cctggacaag cccctcctca actgcttgga gaaacagaga gctcctgatg    720
gagttcgaag aggctcatgc cactaagcag agcgtcgtgg cattggggag tcaggaaggc    780
ggactccacc aggcccttgc cggagccatc gtggtcgagt acagctcaag cgtgaagttg    840
```

```
accagtggac acctgaagtg tagactgaag atggacaaac tggctctgaa ggggacaaca    900

tacggcatgt gcaccgagaa gttcagcttc gccaaaaatc ccgcagacac cgggcatggg    960

acagtcgtca tcgagcttag ctacagcggc tccgacggac catgcaagat tccaattgtg   1020

agcgtggcct ctctcaacga tatgactccc gtgggccggc tggtgactgt gaacccattc   1080

gtggccactt ccagcgctaa cagcaaggtg ttggtggaga tggagccacc tttcggggac   1140

agctatattg tggtggggcg gggagacaaa cagatcaacc atcattggca caaggccggg   1200

tcaacactcg gcaaggcctt ttcaacaact ctcaagggag cccagagact ggccgccctc   1260

ggcgacacag cctgggattt cgggtcaatc ggcggggtgt tcaactcaat cgggaaggct   1320

gtccaccagg tgttcggcgg agcctttcgg accctg                              1356
```

```
<210> SEQ ID NO 12
<211> LENGTH: 452
<212> TYPE: PRT
<213> ORGANISM: Artificial Sequence
<220> FEATURE:
<223> OTHER INFORMATION: soluble form of the E protein lacking the two
      C-terminal transmembrane domains (EdeltaTM).

<400> SEQUENCE: 12

Phe Asn Cys Leu Gly Met Gly Asn Arg Asp Phe Ile Glu Gly Ala Ser
1               5                   10                  15

Gly Ala Thr Trp Val Asp Leu Val Leu Glu Gly Asp Ser Cys Leu Thr
            20                  25                  30

Ile Met Ala Asn Asp Lys Pro Thr Leu Asp Val Arg Met Ile Asn Ile
        35                  40                  45

Glu Ala Ser Gln Leu Ala Glu Val Arg Ser Tyr Cys Tyr His Ala Ser
    50                  55                  60

Val Thr Asp Ile Ser Thr Val Ala Arg Cys Pro Thr Thr Gly Glu Ala
65                  70                  75                  80

His Asn Glu Lys Arg Ala Asp Ser Ser Tyr Val Cys Lys Gln Gly Phe
                85                  90                  95

Thr Asp Arg Gly Trp Gly Asn Gly Cys Gly Leu Phe Gly Lys Gly Ser
            100                 105                 110

Ile Asp Thr Cys Ala Lys Phe Ser Cys Thr Ser Lys Ala Ile Gly Arg
        115                 120                 125

Thr Ile Gln Pro Glu Asn Ile Lys Tyr Glu Val Gly Ile Phe Val His
    130                 135                 140

Gly Thr Thr Thr Ser Glu Asn His Gly Asn Tyr Ser Ala Gln Val Gly
145                 150                 155                 160

Ala Ser Gln Ala Ala Lys Phe Thr Val Thr Pro Asn Ala Pro Ser Ile
                165                 170                 175

Thr Leu Lys Leu Gly Asp Tyr Gly Glu Val Thr Leu Asp Cys Glu Pro
            180                 185                 190

Arg Ser Gly Leu Asn Thr Glu Ala Phe Tyr Val Met Thr Val Gly Ser
        195                 200                 205

Lys Ser Phe Leu Val His Arg Glu Trp Phe His Asp Leu Ala Leu Pro
    210                 215                 220

Trp Thr Ser Pro Ser Ser Thr Ala Trp Arg Asn Arg Glu Leu Leu Met
225                 230                 235                 240

Glu Phe Glu Glu Ala His Ala Thr Lys Gln Ser Val Val Ala Leu Gly
                245                 250                 255

Ser Gln Glu Gly Gly Leu His Gln Ala Leu Ala Gly Ala Ile Val Val
```

-continued

```
            260                 265                 270

Glu Tyr Ser Ser Ser Val Lys Leu Thr Ser Gly His Leu Lys Cys Arg
        275                 280                 285

Leu Lys Met Asp Lys Leu Ala Leu Lys Gly Thr Thr Tyr Gly Met Cys
    290                 295                 300

Thr Glu Lys Phe Ser Phe Ala Lys Asn Pro Ala Asp Thr Gly His Gly
305                 310                 315                 320

Thr Val Val Ile Glu Leu Ser Tyr Ser Gly Ser Asp Gly Pro Cys Lys
                325                 330                 335

Ile Pro Ile Val Ser Val Ala Ser Leu Asn Asp Met Thr Pro Val Gly
            340                 345                 350

Arg Leu Val Thr Val Asn Pro Phe Val Ala Thr Ser Ser Ala Asn Ser
        355                 360                 365

Lys Val Leu Val Glu Met Glu Pro Pro Phe Gly Asp Ser Tyr Ile Val
    370                 375                 380

Val Gly Arg Gly Asp Lys Gln Ile Asn His His Trp His Lys Ala Gly
385                 390                 395                 400

Ser Thr Leu Gly Lys Ala Phe Ser Thr Thr Leu Lys Gly Ala Gln Arg
                405                 410                 415

Leu Ala Ala Leu Gly Asp Thr Ala Trp Asp Phe Gly Ser Ile Gly Gly
            420                 425                 430

Val Phe Asn Ser Ile Gly Lys Ala Val His Gln Val Phe Gly Gly Ala
        435                 440                 445

Phe Arg Thr Leu
    450
```

<210> SEQ ID NO 13
<211> LENGTH: 60
<212> TYPE: DNA
<213> ORGANISM: Artificial Sequence
<220> FEATURE:
<223> OTHER INFORMATION: native nucleotide sequence of the polynucleotide encoding the first transmembrane domain (TMD1) of the E protein.

<400> SEQUENCE: 13
tttgggggaa tgtcttggat cacacaaggg ctaatgggtg ccctactact ctggatgggc 60

<210> SEQ ID NO 14
<211> LENGTH: 60
<212> TYPE: DNA
<213> ORGANISM: Artificial Sequence
<220> FEATURE:
<223> OTHER INFORMATION: codon-optimized nucleotide sequence of the polynucleotide encoding the first transmembrane domain (TMD1) of the E protein.

<400> SEQUENCE: 14
tttgggggaa tgtcttggat tactcagggg ctgatggggg ctctgcttct ttggatgggc 60

<210> SEQ ID NO 15
<211> LENGTH: 20
<212> TYPE: PRT
<213> ORGANISM: Artificial Sequence
<220> FEATURE:
<223> OTHER INFORMATION: first transmembrane domain (TMD1) of the E protein.

<400> SEQUENCE: 15

```
Phe Gly Gly Met Ser Trp Ile Thr Gln Gly Leu Met Gly Ala Leu Leu
1               5                   10                  15
```

Leu Trp Met Gly
20

<210> SEQ ID NO 16
<211> LENGTH: 48
<212> TYPE: DNA
<213> ORGANISM: Artificial Sequence
<220> FEATURE:
<223> OTHER INFORMATION: native nucleotide sequence of the polynucleotide encoding the second transmembrane domain (TMD2) of the E protein.

<400> SEQUENCE: 16
gctttggcct tcttagccac aggaggtgtg ctcgtgttct tagcgacc 48

<210> SEQ ID NO 17
<211> LENGTH: 48
<212> TYPE: DNA
<213> ORGANISM: Artificial Sequence
<220> FEATURE:
<223> OTHER INFORMATION: codon-optimized nucleotide sequence of the polynucleotide encoding the second transmembrane domain (TMD2) of the E protein.

<400> SEQUENCE: 17
gctctggctt tcctggccac aggcggggtg ctcgtgtttc tggctacc 48

<210> SEQ ID NO 18
<211> LENGTH: 16
<212> TYPE: PRT
<213> ORGANISM: Artificial Sequence
<220> FEATURE:
<223> OTHER INFORMATION: second transmembrane domain (TMD2) of the E protein.

<400> SEQUENCE: 18

Ala Leu Ala Phe Leu Ala Thr Gly Gly Val Leu Val Phe Leu Ala Thr
1 5 10 15

<210> SEQ ID NO 19
<211> LENGTH: 2001
<212> TYPE: DNA
<213> ORGANISM: Artificial Sequence
<220> FEATURE:
<223> OTHER INFORMATION: native nucleotide sequence of the polynucleotide encoding the prM-E protein.

<400> SEQUENCE: 19
atgaagttgt caaatttcca ggggaagctt ttgatgacca ttaacaacac ggacattgca 60
gacgttatcg tgattcccac ctcaaaagga gagaacagat gctgggtccg ggcaatcgac 120
gtcggctaca tgtgtgagga cactatcacg tacgaatgtc ctaagcttac catgggcaat 180
gatccagagg atgtggattg ctggtgtgac aaccaagaag tctacgtcca atatggacgg 240
tgcacgcgga ccagacattc caagcgaagc aggagatccg tgtcggtcca aacacatggg 300
gagagttcac tagtgaataa aaaagaggct tggctggatt caacgaaagc cacacgatat 360
ctcatgaaaa ctgagaactg gatcataagg aatcctggct atgctttcct ggcggcggta 420
cttggctgga tgcttggcag taacaacggt caacgcgtgg tattcaccat cctcctgctg 480
ctggttgctc cggcttacag ttttaattgt ctgggaatgg gcaatcgtga cttcatagaa 540
ggagccagtg gagccacttg ggtggacttg gtgctagaag gagatagctg cttgacaatt 600
atggcaaacg acaaaccaac attggacgtc cgcatgatca acatcgaagc tagccaactt 660

```
gctgaggtca gaagttactg ttatcatgct tcagtcactg acatctcgac ggtggctcgg    720
tgccccacga ctggagaagc ccacaacgag aagcgagctg atagtagcta tgtgtgcaaa    780
caaggcttca ctgatcgtgg gtggggcaac ggatgtggac ttttcgggaa gggaagcatt    840
gacacatgtg caaaattctc ctgcaccagt aaagcgattg ggagaacaat ccagccagaa    900
aacatcaaat acgaagttgg catttttgtg catggaacca ccacttcgga aaaccatggg    960
aattattcag cgcaagttgg ggcgtcccag gcggcaaagt ttacagtaac acccaatgct   1020
ccttcgataa ccctcaaact tggtgactac ggagaagtca cactggactg tgagccaagg   1080
agtggactga acactgaagc gttttacgtc atgaccgtgg ggtcaaagtc atttctggtc   1140
catagggaat ggtttcatga cctcgctctc ccctggacgt ccccttcgag cacagcgtgg   1200
agaaacagag aactcctcat ggagtttgaa gaggcgcacg ccacaaaaca gtccgttgtt   1260
gctcttgggt cacaggaagg aggcctccat caggcgttgg caggagccat cgtggtggag   1320
tactcaagct cagtgaagtt aacatcaggc cacctgaaat gtaggctgaa aatggacaaa   1380
ctggctctga aaggcacaac ctatggcatg tgcacagaaa aattctcgtt cgcaaaaaat   1440
ccggcggaca ctggtcacgg aacagttgtc atcgaactct cctactctgg gagtgatggc   1500
ccctgcaaaa ttccgattgt ctccgttgcg agcctcaatg acatgacccc cgttgggcgg   1560
ctggtgacag tgaacccctt cgtcgcgact tccagtgcca attcaaaggt gctggtcgag   1620
atggaacccc ccttcggaga ctcctacatc gtagttggaa ggggagacaa gcagatcaac   1680
caccattggc acaaagctgg aagcacgctg ggcaaagcct tttcaacaac tttgaaggga   1740
gctcagagac tggcagcgtt gggtgacaca gcctgggact ttggctccat tggaggggtc   1800
ttcaactcca taggaaaagc cgttcaccaa gtgtttggtg gtgccttcag aacactcttt   1860
gggggaatgt cttggatcac acaagggcta atgggtgccc tactactctg gatgggcgtc   1920
aacgcacgag accgatcaat tgctttggcc ttcttagcca caggaggtgt gctcgtgttc   1980
ttagcgacca atgtgcatgc t                                             2001
```

```
<210> SEQ ID NO 20
<211> LENGTH: 2001
<212> TYPE: DNA
<213> ORGANISM: Artificial Sequence
<220> FEATURE:
<223> OTHER INFORMATION: codon-optimized nucleotide sequence of the
      polynucleotide encoding the prM-E protein.

<400> SEQUENCE: 20
```

```
atgaagctgt ccaactttca ggggaagctg ctcatgacaa ttaacaacac tgatattgcc     60
gatgtcattg tcatccctac atccaagggc gaaaaccggt gctgggtccg ggccatcgac    120
gtcgggtaca tgtgcgaaga taccattaca tacgaatgcc ccaagctgac catgggaaac    180
gatcctgagg acgtggattg ctggtgcgac aaccaggagg tgtacgtgca gtacgggcgg    240
tgcacaagga cacggcactc caagcgctct cggcggagcg tgtccgtgca gacccacggc    300
gagtcttctc tcgtcaacaa gaaggaggca tggctggata gcactaaggc cacccgctac    360
ctcatgaaga ctgagaactg gatcattcgg aaccctggat acgcttttct ggctgccgtg    420
ctggggtgga tgctggggag caacaacgga cagcgcgtgg tcttcaccat tcttctcttg    480
ttggtcgctc ctgcttacag ctttaactgc ttgggcatgg gcaacaggga tttcatcgag    540
ggcgcctccg gggcaacctg ggtggatttg gtgctcgaag gagacagctg cctcaccatc    600
atggccaacg acaagcccac cctcgacgtg aggatgatca acatcgaggc ttcccaactg    660
```

gccgaggtca gaagctactg ttaccatgcc agcgtgacag atatttccac agtggctagg 720
tgcccaacta caggcgaggc ccacaacgag aaaagggctg atagtagcta tgtctgtaaa 780
cagggcttta ccgatcgggg gtggggcaac gggtgtgggc tgttcgggaa ggggtccatt 840
gatacctgtg ctaagttcag ttgcacttcc aaggccatcg gcaggacaat tcagcctgag 900
aatattaagt acgaggtcgg catctttgtg cacgggacaa ccacaagcga gaaccacggg 960
aactactccg ctcaagtggg cgccagccag gccgccaagt ttacagtgac tcccaacgcc 1020
cccagtatta ctctgaagct gggagactat ggcgaggtga ccctggattg cgagcccaga 1080
tccggcctga acaccgaggc tttttacgtg atgacagtcg gctccaagag tttcttggtg 1140
cacagggagt ggtttcacga cctcgctctc ccctggacaa gcccctcctc aactgcttgg 1200
agaaacagag agctcctgat ggagttcgaa gaggctcatg ccactaagca gagcgtcgtg 1260
gcattgggga gtcaggaagg cggactccac caggcccttg ccggagccat cgtggtcgag 1320
tacagctcaa gcgtgaagtt gaccagtgga cacctgaagt gtagactgaa gatggacaaa 1380
ctggctctga aggggacaac atacggcatg tgcaccgaga agttcagctt cgccaaaaat 1440
cccgcagaca ccgggcatgg gacagtcgtc atcgagctta gctacagcgg ctccgacgga 1500
ccatgcaaga ttccaattgt gagcgtggcc tctctcaacg atatgactcc cgtgggccgg 1560
ctggtgactg tgaacccatt cgtggccact tccagcgcta acagcaaggt gttggtggag 1620
atggagccac ctttcgggga cagctatatt gtggtggggc ggggagacaa acagatcaac 1680
catcattggc acaaggccgg gtcaacactc ggcaaggcct tttcaacaac tctcaaggga 1740
gcccagagac tggccgccct cggcgacaca gcctgggatt tcgggtcaat cggcggggtg 1800
ttcaactcaa tcgggaaggc tgtccaccag gtgttcggcg gagcctttcg gaccctgttt 1860
gggggaatgt cttggattac tcaggggctg atgggggctc tgcttctttg gatgggcgtc 1920
aacgcccggg acaggagtat cgctctggct ttcctggcca caggcggggt gctcgtgttt 1980
ctggctacca atgtccatgc t 2001

<210> SEQ ID NO 21
<211> LENGTH: 667
<212> TYPE: PRT
<213> ORGANISM: Artificial Sequence
<220> FEATURE:
<223> OTHER INFORMATION: prM-E protein.

<400> SEQUENCE: 21

Met Lys Leu Ser Asn Phe Gln Gly Lys Leu Leu Met Thr Ile Asn Asn
1 5 10 15

Thr Asp Ile Ala Asp Val Ile Val Ile Pro Thr Ser Lys Gly Glu Asn
20 25 30

Arg Cys Trp Val Arg Ala Ile Asp Val Gly Tyr Met Cys Glu Asp Thr
35 40 45

Ile Thr Tyr Glu Cys Pro Lys Leu Thr Met Gly Asn Asp Pro Glu Asp
50 55 60

Val Asp Cys Trp Cys Asp Asn Gln Glu Val Tyr Val Gln Tyr Gly Arg
65 70 75 80

Cys Thr Arg Thr Arg His Ser Lys Arg Ser Arg Arg Ser Val Ser Val
85 90 95

Gln Thr His Gly Glu Ser Ser Leu Val Asn Lys Lys Glu Ala Trp Leu
100 105 110

Asp Ser Thr Lys Ala Thr Arg Tyr Leu Met Lys Thr Glu Asn Trp Ile
115 120 125

-continued

```
Ile Arg Asn Pro Gly Tyr Ala Phe Leu Ala Ala Val Leu Gly Trp Met
    130                 135                 140

Leu Gly Ser Asn Asn Gly Gln Arg Val Val Phe Thr Ile Leu Leu Leu
145                 150                 155                 160

Leu Val Ala Pro Ala Tyr Ser Phe Asn Cys Leu Gly Met Gly Asn Arg
                165                 170                 175

Asp Phe Ile Glu Gly Ala Ser Gly Ala Thr Trp Val Asp Leu Val Leu
            180                 185                 190

Glu Gly Asp Ser Cys Leu Thr Ile Met Ala Asn Asp Lys Pro Thr Leu
        195                 200                 205

Asp Val Arg Met Ile Asn Ile Glu Ala Ser Gln Leu Ala Glu Val Arg
    210                 215                 220

Ser Tyr Cys Tyr His Ala Ser Val Thr Asp Ile Ser Thr Val Ala Arg
225                 230                 235                 240

Cys Pro Thr Thr Gly Glu Ala His Asn Glu Lys Arg Ala Asp Ser Ser
                245                 250                 255

Tyr Val Cys Lys Gln Gly Phe Thr Asp Arg Gly Trp Gly Asn Gly Cys
            260                 265                 270

Gly Leu Phe Gly Lys Gly Ser Ile Asp Thr Cys Ala Lys Phe Ser Cys
        275                 280                 285

Thr Ser Lys Ala Ile Gly Arg Thr Ile Gln Pro Glu Asn Ile Lys Tyr
    290                 295                 300

Glu Val Gly Ile Phe Val His Gly Thr Thr Thr Ser Glu Asn His Gly
305                 310                 315                 320

Asn Tyr Ser Ala Gln Val Gly Ala Ser Gln Ala Ala Lys Phe Thr Val
                325                 330                 335

Thr Pro Asn Ala Pro Ser Ile Thr Leu Lys Leu Gly Asp Tyr Gly Glu
            340                 345                 350

Val Thr Leu Asp Cys Glu Pro Arg Ser Gly Leu Asn Thr Glu Ala Phe
        355                 360                 365

Tyr Val Met Thr Val Gly Ser Lys Ser Phe Leu Val His Arg Glu Trp
    370                 375                 380

Phe His Asp Leu Ala Leu Pro Trp Thr Ser Pro Ser Ser Thr Ala Trp
385                 390                 395                 400

Arg Asn Arg Glu Leu Leu Met Glu Phe Glu Glu Ala His Ala Thr Lys
                405                 410                 415

Gln Ser Val Val Ala Leu Gly Ser Gln Glu Gly Gly Leu His Gln Ala
            420                 425                 430

Leu Ala Gly Ala Ile Val Val Glu Tyr Ser Ser Ser Val Lys Leu Thr
        435                 440                 445

Ser Gly His Leu Lys Cys Arg Leu Lys Met Asp Lys Leu Ala Leu Lys
    450                 455                 460

Gly Thr Thr Tyr Gly Met Cys Thr Glu Lys Phe Ser Phe Ala Lys Asn
465                 470                 475                 480

Pro Ala Asp Thr Gly His Gly Thr Val Val Ile Glu Leu Ser Tyr Ser
                485                 490                 495

Gly Ser Asp Gly Pro Cys Lys Ile Pro Ile Val Ser Val Ala Ser Leu
            500                 505                 510

Asn Asp Met Thr Pro Val Gly Arg Leu Val Thr Val Asn Pro Phe Val
        515                 520                 525

Ala Thr Ser Ser Ala Asn Ser Lys Val Leu Val Glu Met Glu Pro Pro
    530                 535                 540
```

```
Phe Gly Asp Ser Tyr Ile Val Val Gly Arg Gly Asp Lys Gln Ile Asn
545                 550                 555                 560

His His Trp His Lys Ala Gly Ser Thr Leu Gly Lys Ala Phe Ser Thr
                565                 570                 575

Thr Leu Lys Gly Ala Gln Arg Leu Ala Ala Leu Gly Asp Thr Ala Trp
            580                 585                 590

Asp Phe Gly Ser Ile Gly Gly Val Phe Asn Ser Ile Gly Lys Ala Val
        595                 600                 605

His Gln Val Phe Gly Gly Ala Phe Arg Thr Leu Phe Gly Gly Met Ser
    610                 615                 620

Trp Ile Thr Gln Gly Leu Met Gly Ala Leu Leu Leu Trp Met Gly Val
625                 630                 635                 640

Asn Ala Arg Asp Arg Ser Ile Ala Leu Ala Phe Leu Ala Thr Gly Gly
                645                 650                 655

Val Leu Val Phe Leu Ala Thr Asn Val His Ala
            660                 665


<210> SEQ ID NO 22
<211> LENGTH: 1857
<212> TYPE: DNA
<213> ORGANISM: Artificial Sequence
<220> FEATURE:
<223> OTHER INFORMATION: native nucleotide sequence of the
      polynucleotide encoding the prM-EdeltaTM protein.

<400> SEQUENCE: 22

atgaagttgt caaatttcca ggggaagctt ttgatgacca ttaacaacac ggacattgca     60

gacgttatcg tgattcccac ctcaaaagga gagaacagat gctgggtccg ggcaatcgac    120

gtcggctaca tgtgtgagga cactatcacg tacgaatgtc ctaagcttac catgggcaat    180

gatccagagg atgtggattg ctggtgtgac aaccaagaag tctacgtcca atatggacgg    240

tgcacgcgga ccagacattc caagcgaagc aggagatccg tgtcggtcca aacacatggg    300

gagagttcac tagtgaataa aaaagaggct tggctggatt caacgaaagc cacacgatat    360

ctcatgaaaa ctgagaactg gatcataagg aatcctggct atgctttcct ggcggcggta    420

cttggctgga tgcttggcag taacaacggt caacgcgtgg tattcaccat cctcctgctg    480

ctggttgctc cggcttacag ttttaattgt ctgggaatgg gcaatcgtga cttcatagaa    540

ggagccagtg gagccacttg ggtggacttg gtgctagaag gagatagctg cttgacaatt    600

atggcaaacg acaaaccaac attggacgtc cgcatgatca acatcgaagc tagccaactt    660

gctgaggtca gaagttactg ttatcatgct tcagtcactg acatctcgac ggtggctcgg    720

tgccccacga ctggagaagc ccacaacgag aagcgagctg atagtagcta tgtgtgcaaa    780

caaggcttca ctgatcgtgg gtggggcaac ggatgtggac ttttcgggaa gggaagcatt    840

gacacatgtg caaaattctc ctgcaccagt aaagcgattg ggagaacaat ccagccagaa    900

aacatcaaat acgaagttgg cattttttgtg catggaacca ccacttcgga aaaccatggg    960

aattattcag cgcaagttgg ggcgtcccag gcggcaaagt ttacagtaac acccaatgct   1020

ccttcgataa ccctcaaact tggtgactac ggagaagtca cactggactg tgagccaagg   1080

agtggactga acactgaagc gttttacgtc atgaccgtgg ggtcaaagtc atttctggtc   1140

catagggaat ggtttcatga cctcgctctc ccctggacgt ccccttcgag cacagcgtgg   1200

agaaacagag aactcctcat ggagtttgaa gaggcgcacg ccacaaaaca gtccgttgtt   1260

gctcttgggt cacaggaagg aggcctccat caggcgttgg caggagccat cgtggtggag   1320
```

-continued

```
tactcaagct cagtgaagtt aacatcaggc cacctgaaat gtaggctgaa aatggacaaa   1380

ctggctctga aaggcacaac ctatggcatg tgcacagaaa aattctcgtt cgcaaaaaat   1440

ccggcggaca ctggtcacgg aacagttgtc atcgaactct cctactctgg gagtgatggc   1500

ccctgcaaaa ttccgattgt ctccgttgcg agcctcaatg acatgacccc cgttgggcgg   1560

ctggtgacag tgaacccctt cgtcgcgact tccagtgcca attcaaaggt gctggtcgag   1620

atggaacccc ccttcggaga ctcctacatc gtagttggaa ggggagacaa gcagatcaac   1680

caccattggc acaaagctgg aagcacgctg ggcaaagcct tttcaacaac tttgaaggga   1740

gctcagagac tggcagcgtt gggtgacaca gcctgggact ttggctccat tggaggggtc   1800

ttcaactcca taggaaaagc cgttcaccaa gtgtttggtg gtgccttcag aacactc      1857


<210> SEQ ID NO 23
<211> LENGTH: 1857
<212> TYPE: DNA
<213> ORGANISM: Artificial Sequence
<220> FEATURE:
<223> OTHER INFORMATION: codon-optimized nucleotide sequence of the
      polynucleotide encoding the prM-EdeltaTM protein.

<400> SEQUENCE: 23

atgaagctgt ccaactttca ggggaagctg ctcatgacaa ttaacaacac tgatattgcc     60

gatgtcattg tcatccctac atccaagggc gaaaaccggt gctgggtccg ggccatcgac    120

gtcgggtaca tgtgcgaaga taccattaca tacgaatgcc ccaagctgac catgggaaac    180

gatcctgagg acgtggattg ctggtgcgac aaccaggagg tgtacgtgca gtacgggcgg    240

tgcacaagga cacggcactc caagcgctct cggcggagcg tgtccgtgca gacccacggc    300

gagtcttctc tcgtcaacaa gaaggaggca tggctggata gcactaaggc cacccgctac    360

ctcatgaaga ctgagaactg gatcattcgg aaccctggat acgcttttct ggctgccgtg    420

ctggggtgga tgctggggag caacaacgga cagcgcgtgg tcttcaccat tcttctcttg    480

ttggtcgctc ctgcttacag ctttaactgc ttgggcatgg gcaacaggga tttcatcgag    540

ggcgcctccg ggcaacctgg ggtggatttg gtgctcgaag gagacagctg cctcaccatc    600

atggccaacg acaagcccac cctcgacgtg aggatgatca acatcgaggc ttcccaactg    660

gccgaggtca gaagctactg ttaccatgcc agcgtgacag atatttccac agtggctagg    720

tgcccaacta caggcgaggc ccacaacgag aaaagggctg atagtagcta tgtctgtaaa    780

cagggcttta ccgatcgggg gtggggcaac gggtgtgggc tgttcgggaa ggggtccatt    840

gatacctgtg ctaagttcag ttgcacttcc aaggccatcg gcaggacaat tcagcctgag    900

aatattaagt acgaggtcgg catctttgtg cacgggacaa ccacaagcga gaaccacggg    960

aactactccg ctcaagtggg cgccagccag gccgccaagt ttacagtgac tcccaacgcc   1020

cccagtatta ctctgaagct gggagactat ggcgaggtga ccctggattg cgagcccaga   1080

tccggcctga acaccgaggc tttttacgtg atgacagtcg gctccaagag tttcttggtg   1140

cacagggagt ggtttcacga cctcgctctc ccctggacaa gcccctcctc aactgcttgg   1200

agaaacagag agctcctgat ggagttcgaa gaggctcatg ccactaagca gagcgtcgtg   1260

gcattgggga gtcaggaagg cggactccac caggcccttg ccggagccat cgtggtcgag   1320

tacagctcaa gcgtgaagtt gaccagtgga cacctgaagt gtagactgaa gatggacaaa   1380

ctggctctga aggggacaac atacggcatg tgcaccgaga agttcagctt cgccaaaaat   1440

cccgcagaca ccgggcatgg gacagtcgtc atcgagctta gctacagcgg ctccgacgga   1500
```

-continued ccatgcaaga ttccaattgt gagcgtggcc tctctcaacg atatgactcc cgtgggccgg 1560
ctggtgactg tgaacccatt cgtggccact tccagcgcta acagcaaggt gttggtggag 1620
atggagccac ctttcgggga cagctatatt gtggtggggc ggggagacaa acagatcaac 1680
catcattggc acaaggccgg gtcaacactc ggcaaggcct tttcaacaac tctcaaggga 1740
gcccagagac tggccgccct cggcgacaca gcctgggatt tcgggtcaat cggcggggtg 1800
ttcaactcaa tcgggaaggc tgtccaccag gtgttcggcg gagcctttcg gaccctg 1857

<210> SEQ ID NO 24
<211> LENGTH: 619
<212> TYPE: PRT
<213> ORGANISM: Artificial Sequence
<220> FEATURE:
<223> OTHER INFORMATION: prM-EdeltaTM protein.

<400> SEQUENCE: 24

Met Lys Leu Ser Asn Phe Gln Gly Lys Leu Leu Met Thr Ile Asn Asn
1 5 10 15

Thr Asp Ile Ala Asp Val Ile Val Ile Pro Thr Ser Lys Gly Glu Asn
20 25 30

Arg Cys Trp Val Arg Ala Ile Asp Val Gly Tyr Met Cys Glu Asp Thr
35 40 45

Ile Thr Tyr Glu Cys Pro Lys Leu Thr Met Gly Asn Asp Pro Glu Asp
50 55 60

Val Asp Cys Trp Cys Asp Asn Gln Glu Val Tyr Val Gln Tyr Gly Arg
65 70 75 80

Cys Thr Arg Thr Arg His Ser Lys Arg Ser Arg Arg Ser Val Ser Val
85 90 95

Gln Thr His Gly Glu Ser Ser Leu Val Asn Lys Lys Glu Ala Trp Leu
100 105 110

Asp Ser Thr Lys Ala Thr Arg Tyr Leu Met Lys Thr Glu Asn Trp Ile
115 120 125

Ile Arg Asn Pro Gly Tyr Ala Phe Leu Ala Ala Val Leu Gly Trp Met
130 135 140

Leu Gly Ser Asn Asn Gly Gln Arg Val Val Phe Thr Ile Leu Leu Leu
145 150 155 160

Leu Val Ala Pro Ala Tyr Ser Phe Asn Cys Leu Gly Met Gly Asn Arg
165 170 175

Asp Phe Ile Glu Gly Ala Ser Gly Ala Thr Trp Val Asp Leu Val Leu
180 185 190

Glu Gly Asp Ser Cys Leu Thr Ile Met Ala Asn Asp Lys Pro Thr Leu
195 200 205

Asp Val Arg Met Ile Asn Ile Glu Ala Ser Gln Leu Ala Glu Val Arg
210 215 220

Ser Tyr Cys Tyr His Ala Ser Val Thr Asp Ile Ser Thr Val Ala Arg
225 230 235 240

Cys Pro Thr Thr Gly Glu Ala His Asn Glu Lys Arg Ala Asp Ser Ser
245 250 255

Tyr Val Cys Lys Gln Gly Phe Thr Asp Arg Gly Trp Gly Asn Gly Cys
260 265 270

Gly Leu Phe Gly Lys Gly Ser Ile Asp Thr Cys Ala Lys Phe Ser Cys
275 280 285

Thr Ser Lys Ala Ile Gly Arg Thr Ile Gln Pro Glu Asn Ile Lys Tyr
290 295 300

Glu Val Gly Ile Phe Val His Gly Thr Thr Thr Ser Glu Asn His Gly
305 310 315 320

Asn Tyr Ser Ala Gln Val Gly Ala Ser Gln Ala Ala Lys Phe Thr Val
325 330 335

Thr Pro Asn Ala Pro Ser Ile Thr Leu Lys Leu Gly Asp Tyr Gly Glu
340 345 350

Val Thr Leu Asp Cys Glu Pro Arg Ser Gly Leu Asn Thr Glu Ala Phe
355 360 365

Tyr Val Met Thr Val Gly Ser Lys Ser Phe Leu Val His Arg Glu Trp
370 375 380

Phe His Asp Leu Ala Leu Pro Trp Thr Ser Pro Ser Ser Thr Ala Trp
385 390 395 400

Arg Asn Arg Glu Leu Leu Met Glu Phe Glu Glu Ala His Ala Thr Lys
405 410 415

Gln Ser Val Val Ala Leu Gly Ser Gln Glu Gly Gly Leu His Gln Ala
420 425 430

Leu Ala Gly Ala Ile Val Val Glu Tyr Ser Ser Ser Val Lys Leu Thr
435 440 445

Ser Gly His Leu Lys Cys Arg Leu Lys Met Asp Lys Leu Ala Leu Lys
450 455 460

Gly Thr Thr Tyr Gly Met Cys Thr Glu Lys Phe Ser Phe Ala Lys Asn
465 470 475 480

Pro Ala Asp Thr Gly His Gly Thr Val Val Ile Glu Leu Ser Tyr Ser
485 490 495

Gly Ser Asp Gly Pro Cys Lys Ile Pro Ile Val Ser Val Ala Ser Leu
500 505 510

Asn Asp Met Thr Pro Val Gly Arg Leu Val Thr Val Asn Pro Phe Val
515 520 525

Ala Thr Ser Ser Ala Asn Ser Lys Val Leu Val Glu Met Glu Pro Pro
530 535 540

Phe Gly Asp Ser Tyr Ile Val Val Gly Arg Gly Asp Lys Gln Ile Asn
545 550 555 560

His His Trp His Lys Ala Gly Ser Thr Leu Gly Lys Ala Phe Ser Thr
565 570 575

Thr Leu Lys Gly Ala Gln Arg Leu Ala Ala Leu Gly Asp Thr Ala Trp
580 585 590

Asp Phe Gly Ser Ile Gly Gly Val Phe Asn Ser Ile Gly Lys Ala Val
595 600 605

His Gln Val Phe Gly Gly Ala Phe Arg Thr Leu
610 615

<210> SEQ ID NO 25
<211> LENGTH: 15
<212> TYPE: PRT
<213> ORGANISM: Artificial Sequence
<220> FEATURE:
<223> OTHER INFORMATION: the last 15 amino acids of the prM/M protein.

<400> SEQUENCE: 25

Val Val Phe Thr Ile Leu Leu Leu Leu Val Ala Pro Ala Tyr Ser
1 5 10 15

<210> SEQ ID NO 26
<211> LENGTH: 636
<212> TYPE: DNA
<213> ORGANISM: Artificial Sequence
<220> FEATURE:

<223> OTHER INFORMATION: nucleotide sequence of HIV1- 5'LTR

<400> SEQUENCE: 26
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240
agagagaagt gttagagtgg aggtttgaca gccgcctagc atttcatcac ggtggcccga 300
gagctgcatc cggagtactt caagaactgc tgatatcgag cttgctacaa gggactttcc 360 gctggggac tttccaggga ggcgtggcct gggcgggact ggggagtggc gagccctcag 420
atcctgcata taagcagctg ctttttgcct gtactgggtc tctctggtta gaccagatct 480
gagcctggga gctctctggc taactaggga acccactgct taagcctcaa taaagcttgc 540
cttgagtgct tcaagtagtg tgtgcccgtc tgttgtgtga ctctggtaac tagagatccc 600
tcagaccctt ttagtcagtg tggaaaatct ctagca 636

<210> SEQ ID NO 27
<211> LENGTH: 234
<212> TYPE: DNA
<213> ORGANISM: Artificial Sequence
<220> FEATURE:
<223> OTHER INFORMATION: nucleotide sequence of RRE

<400> SEQUENCE: 27
aggagctttg ttccttgggt tcttgggagc agcaggaagc actatgggcg cagcgtcaat 60
gacgctgacg gtacaggcca gacaattatt gtctggtata gtgcagcagc agaacaattt 120
gctgagggct attgaggcgc aacagcatct gttgcaactc acagtctggg gcatcaagca 180
gctccaggca agaatcctgg ctgtggaaag atacctaaag gatcaacagc tcct 234

<210> SEQ ID NO 28
<211> LENGTH: 124
<212> TYPE: DNA
<213> ORGANISM: Artificial Sequence
<220> FEATURE:
<223> OTHER INFORMATION: nucleotide sequence of cPPT-CTS

<400> SEQUENCE: 28
ttttaaaaga aaagggggga ttggggggta cagtgcaggg gaaagaatag tagacataat 60
agcaacagac atacaaacta aagaattaca aaaacaaatt acaaaaattc aaaattttcg 120
ggtt 124

<210> SEQ ID NO 29
<211> LENGTH: 527
<212> TYPE: DNA
<213> ORGANISM: Artificial Sequence
<220> FEATURE:
<223> OTHER INFORMATION: nucleotide sequence of CMV promoter

<400> SEQUENCE: 29
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagctcg tttagtgaac cgtcaga 527

<210> SEQ ID NO 30
<211> LENGTH: 605
<212> TYPE: DNA
<213> ORGANISM: Artificial Sequence
<220> FEATURE:
<223> OTHER INFORMATION: nucleotide sequence of WPRE

<400> SEQUENCE: 30
aattcccgat aatcaacctc tggattacaa aatttgtgaa agattgactg gtattcttaa 60
ctatgttgct ccttttacgc tatgtggata cgctgcttta atgcctttgt atcatgctat 120
tgcttcccgt atggctttca ttttctcctc cttgtataaa tcctggttgc tgtctcttta 180
tgaggagttg tggcccgttg tcaggcaacg tggcgtggtg tgcactgtgt ttgctgacgc 240
aacccccact ggttggggca ttgccaccac ctgtcagctc ctttccggga ctttcgcttt 300
ccccctccct attgccacgg cggaactcat cgccgcctgc cttgcccgct gctggacagg 360
ggctcggctg ttgggcactg acaattccgt ggtgttgtcg gggaagctga cgtcctttcc 420
atggctgctc gcctgtgttg ccacctggat tctgcgcggg acgtccttct gctacgtccc 480
ttcggccctc aatccagcgg accttccttc ccgcggcctg ctgccggctc tgcggcctct 540
tccgcgtctt cgccttcgcc ctcagacgag tcggatctcc ctttgggccg cctccccgca 600
tcggg 605

<210> SEQ ID NO 31
<211> LENGTH: 262
<212> TYPE: DNA
<213> ORGANISM: Artificial Sequence
<220> FEATURE:
<223> OTHER INFORMATION: nucleotide sequence of HIV1- 3'LTR

<400> SEQUENCE: 31
actggaaggg ctaattcact cccaacgaag acaagatcgt cgagagatgc tgcatataag 60
cagctgcttt ttgcttgtac tgggtctctc tggttagacc agatctgagc ctgggagctc 120
tctggctaac tagggaaccc actgcttaag cctcaataaa gcttgccttg agtgcttcaa 180
gtagtgtgtg cccgtctgtt gtgtgactct ggtaactaga gatccctcag acccttttag 240
tcagtgtgga aaatctctag ca 262

<210> SEQ ID NO 32
<211> LENGTH: 2073
<212> TYPE: DNA
<213> ORGANISM: Artificial Sequence
<220> FEATURE:
<223> OTHER INFORMATION: nucleotide sequence of the polynucleotide
encoding the signal peptide-prME protein.

<400> SEQUENCE: 32
atgggcggaa acgaagggtc cattatgtgg ctcgcctccc tggccgtggt gatcgcctgc 60
gccggagcaa tgaagctgtc caactttcag gggaagctgc tcatgacaat taacaacact 120
gatattgccg atgtcattgt catccctaca tccaagggcg aaaaccggtg ctgggtccgg 180
gccatcgacg tcgggtacat gtgcgaagat accattacat acgaatgccc caagctgacc 240

-continued atgggaaacg atcctgagga cgtggattgc tggtgcgaca accaggaggt gtacgtgcag 300
tacgggcggt gcacaaggac acggcactcc aagcgctctc ggcggagcgt gtccgtgcag 360
acccacggcg agtcttctct cgtcaacaag aaggaggcat ggctggatag cactaaggcc 420
acccgctacc tcatgaagac tgagaactgg atcattcgga accctggata cgcttttctg 480
gctgccgtgc tggggtggat gctggggagc aacaacggac agcgcgtggt cttcaccatt 540
cttctcttgt tggtcgctcc tgcttacagc tttaactgct tgggcatggg caacagggat 600
ttcatcgagg gcgcctccgg ggcaacctgg gtggatttgg tgctcgaagg agacagctgc 660
ctcaccatca tggccaacga caagcccacc ctcgacgtga ggatgatcaa catcgaggct 720
tcccaactgg ccgaggtcag aagctactgt taccatgcca gcgtgacaga tatttccaca 780
gtggctaggt gcccaactac aggcgaggcc cacaacgaga aaagggctga tagtagctat 840
gtctgtaaac agggctttac cgatcggggg tggggcaacg ggtgtgggct gttcgggaag 900
gggtccattg atacctgtgc taagttcagt tgcacttcca aggccatcgg caggacaatt 960
cagcctgaga atattaagta cgaggtcggc atctttgtgc acgggacaac cacaagcgag 1020
aaccacggga actactccgc tcaagtgggc gccagccagg ccgccaagtt tacagtgact 1080
cccaacgccc ccagtattac tctgaagctg ggagactatg gcgaggtgac cctggattgc 1140
gagcccagat ccggcctgaa caccgaggct ttttacgtga tgacagtcgg ctccaagagt 1200
ttcttggtgc acagggagtg gtttcacgac ctcgctctcc cctggacaag cccctcctca 1260
actgcttgga gaaacagaga gctcctgatg gagttcgaag aggctcatgc cactaagcag 1320
agcgtcgtgg cattggggag tcaggaaggc ggactccacc aggcccttgc cggagccatc 1380
gtggtcgagt acagctcaag cgtgaagttg accagtggac acctgaagtg tagactgaag 1440
atggacaaac tggctctgaa ggggacaaca tacggcatgt gcaccgagaa gttcagcttc 1500
gccaaaaatc ccgcagacac cgggcatggg acagtcgtca tcgagcttag ctacagcggc 1560
tccgacggac catgcaagat tccaattgtg agcgtggcct ctctcaacga tatgactccc 1620
gtgggccggc tggtgactgt gaacccattc gtggccactt ccagcgctaa cagcaaggtg 1680
ttggtggaga tggagccacc tttcggggac agctatattg tggtggggcg gggagacaaa 1740
cagatcaacc atcattggca caaggccggg tcaacactcg gcaaggcctt ttcaacaact 1800
ctcaagggag cccagagact ggccgccctc ggcgacacag cctgggattt cgggtcaatc 1860
ggcggggtgt tcaactcaat cggaaaggct gtccaccagg tgttcggcgg agcctttcgg 1920
accctgtttg gggaatgtc ttggattact caggggctga tgggggctct gcttctttgg 1980
atgggcgtca acgcccggga caggagtatc gctctggctt tcctggccac aggcggggtg 2040
ctcgtgtttc tggctaccaa tgtccatgct tga 2073

<210> SEQ ID NO 33
<211> LENGTH: 1929
<212> TYPE: DNA
<213> ORGANISM: Artificial Sequence
<220> FEATURE:
<223> OTHER INFORMATION: nucleotide sequence of the polynucleotide encoding the signal peptide-prMEdeltaTM protein.

<400> SEQUENCE: 33
atgggcggaa acgaagggtc cattatgtgg ctcgcctccc tggccgtggt gatcgcctgc 60
gccggagcaa tgaagctgtc caactttcag gggaagctgc tcatgacaat taacaacact 120
gatattgccg atgtcattgt catccctaca tccaagggcg aaaaccggtg ctgggtccgg 180
gccatcgacg tcgggtacat gtgcgaagat accattacat acgaatgccc caagctgacc 240
atgggaaacg atcctgagga cgtggattgc tggtgcgaca accaggaggt gtacgtgcag 300
tacgggcggt gcacaaggac acggcactcc aagcgctctc ggcggagcgt gtccgtgcag 360
acccacggcg agtcttctct cgtcaacaag aaggaggcat ggctggatag cactaaggcc 420
acccgctacc tcatgaagac tgagaactgg atcattcgga accctggata cgcttttctg 480
gctgccgtgc tggggtggat gctggggagc aacaacggac agcgcgtggt cttcaccatt 540
cttctcttgt tggtcgctcc tgcttacagc tttaactgct tgggcatggg caacagggat 600
ttcatcgagg gcgcctccgg ggcaacctgg gtggatttgg tgctcgaagg agacagctgc 660
ctcaccatca tggccaacga caagcccacc ctcgacgtga ggatgatcaa catcgaggct 720
tcccaactgg ccgaggtcag aagctactgt taccatgcca gcgtgacaga tatttccaca 780
gtggctaggt gcccaactac aggcgaggcc cacaacgaga aaagggctga tagtagctat 840
gtctgtaaac agggctttac cgatcggggg tggggcaacg ggtgtgggct gttcgggaag 900
gggtccattg atacctgtgc taagttcagt tgcacttcca aggccatcgg caggacaatt 960
cagcctgaga atattaagta cgaggtcggc atctttgtgc acgggacaac cacaagcgag 1020
aaccacggga actactccgc tcaagtgggc gccagccagg ccgccaagtt tacagtgact 1080
cccaacgccc ccagtattac tctgaagctg ggagactatg gcgaggtgac cctggattgc 1140
gagcccagat ccggcctgaa caccgaggct ttttacgtga tgacagtcgg ctccaagagt 1200
ttcttggtgc acagggagtg gtttcacgac ctcgctctcc cctggacaag cccctcctca 1260
actgcttgga gaaacagaga gctcctgatg gagttcgaag aggctcatgc cactaagcag 1320
agcgtcgtgg cattggggag tcaggaaggc ggactccacc aggcccttgc cggagccatc 1380
gtggtcgagt acagctcaag cgtgaagttg accagtggac acctgaagtg tagactgaag 1440
atggacaaac tggctctgaa ggggacaaca tacggcatgt gcaccgagaa gttcagcttc 1500
gccaaaaatc ccgcagacac cgggcatggg acagtcgtca tcgagcttag ctacagcggc 1560
tccgacggac catgcaagat tccaattgtg agcgtggcct ctctcaacga tatgactccc 1620
gtgggccggc tggtgactgt gaacccattc gtggccactt ccagcgctaa cagcaaggtg 1680
ttggtggaga tggagccacc tttcggggac agctatattg tggtggggcg gggagacaaa 1740
cagatcaacc atcattggca caaggccggg tcaacactcg gcaaggcctt ttcaacaact 1800
ctcaagggag cccagagact ggccgccctc ggcgacacag cctgggattt cgggtcaatc 1860
ggcggggtgt tcaactcaat cgggaaggct gtccaccagg tgttcggcgg agcctttcgg 1920
accctgtga 1929

<210> SEQ ID NO 34
<211> LENGTH: 5866
<212> TYPE: DNA
<213> ORGANISM: Artificial Sequence
<220> FEATURE:
<223> OTHER INFORMATION: recombinant lentiviral backbone
TRIPdeltaU3.CMV/JEV.prME

<400> SEQUENCE: 34
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240

-continued

```
agagagaagt gttagagtgg aggtttgaca gccgcctagc atttcatcac ggtggcccga    300
gagctgcatc cggagtactt caagaactgc tgatatcgag cttgctacaa gggactttcc    360
gctggggac tttccaggga ggcgtggcct gggcgggact ggggagtggc gagccctcag    420
atcctgcata taagcagctg ctttttgcct gtactgggtc tctctggtta gaccagatct    480
gagcctggga gctctctggc taactaggga acccactgct taagcctcaa taaagcttgc    540
cttgagtgct tcaagtagtg tgtgcccgtc tgttgtgtga ctctggtaac tagagatccc    600
tcagaccctt ttagtcagtg tggaaaatct ctagcagtgg cgcccgaaca gggacttgaa    660
agcgaaaggg aaaccagagg agctctctcg acgcaggact cggcttgctg aagcgcgcac    720
ggcaagaggc gaggggcggc gactggtgag tacgccaaaa attttgacta gcggaggcta    780
gaaggagaga gatgggtgcg agagcgtcag tattaagcgg gggagaatta gatcgcgatg    840
ggaaaaaatt cggttaaggc cagggggaaa gaaaaaatat aaattaaaac atatagtatg    900
ggcaagcagg gagctagaac gattcgcagt taatcctggc ctgttagaaa catcagaagg    960
ctgtagacaa atactgggac agctacaacc atcccttcag acaggatcag aagaacttag   1020
atcattatat aatacagtag caaccctcta ttgtgtgcat caaaggatag agataaaaga   1080
caccaaggaa gctttagaca agatagagga agagcaaaac aaaagtaaga ccaccgcaca   1140
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
```

-continued

```
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgggcgg aaacgaaggg tccattatgt ggctcgcctc cctggccgtg gtgatcgcct   2880
gcgccggagc aatgaagctg tccaactttc aggggaagct gctcatgaca attaacaaca   2940
ctgatattgc cgatgtcatt gtcatcccta catccaaggg cgaaaaccgg tgctgggtcc   3000
gggccatcga cgtcgggtac atgtgcgaag ataccattac atacgaatgc cccaagctga   3060
ccatgggaaa cgatcctgag gacgtggatt gctggtgcga caaccaggag gtgtacgtgc   3120
agtacgggcg gtgcacaagg acacggcact ccaagcgctc tcggcggagc gtgtccgtgc   3180
agacccacgg cgagtcttct ctcgtcaaca agaaggaggc atggctggat agcactaagg   3240
ccacccgcta cctcatgaag actgagaact ggatcattcg gaaccctgga tacgcttttc   3300
tggctgccgt gctggggtgg atgctgggga gcaacaacgg acagcgcgtg gtcttcacca   3360
ttcttctctt gttggtcgct cctgcttaca gctttaactg cttgggcatg ggcaacaggg   3420
atttcatcga gggcgcctcc ggggcaacct gggtggattt ggtgctcgaa ggagacagct   3480
gcctcaccat catggccaac gacaagccca ccctcgacgt gaggatgatc aacatcgagg   3540
cttcccaact ggccgaggtc agaagctact gttaccatgc cagcgtgaca gatatttcca   3600
cagtggctag gtgcccaact acaggcgagg cccacaacga gaaaagggct gatagtagct   3660
atgtctgtaa acagggcttt accgatcggg ggtggggcaa cgggtgtggg ctgttcggga   3720
aggggtccat tgatacctgt gctaagttca gttgcacttc caaggccatc ggcaggacaa   3780
ttcagcctga gaatattaag tacgaggtcg gcatctttgt gcacgggaca accacaagcg   3840
agaaccacgg gaactactcc gctcaagtgg gcgccagcca ggccgccaag tttacagtga   3900
ctcccaacgc ccccagtatt actctgaagc tgggagacta tggcgaggtg accctggatt   3960
gcgagcccag atccggcctg aacaccgagg ctttttacgt gatgacagtc ggctccaaga   4020
gtttcttggt gcacagggag tggtttcacg acctcgctct cccctggaca agcccctcct   4080
caactgcttg gagaaacaga gagctcctga tggagttcga agaggctcat gccactaagc   4140
agagcgtcgt ggcattgggg agtcaggaag gcggactcca ccaggccctt gccggagcca   4200
tcgtggtcga gtacagctca agcgtgaagt tgaccagtgg acacctgaag tgtagactga   4260
agatggacaa actggctctg aaggggacaa catacggcat gtgcaccgag aagttcagct   4320
tcgccaaaaa tcccgcagac accgggcatg ggacagtcgt catcgagctt agctacagcg   4380
gctccgacgg accatgcaag attccaattg tgagcgtggc ctctctcaac gatatgactc   4440
ccgtgggccg gctggtgact gtgaacccat tcgtggccac ttccagcgct aacagcaagg   4500
tgttggtgga gatggagcca ccctttcggg acagctatat tgtggtgggg cggggagaca   4560
aacagatcaa ccatcattgg cacaaggccg ggtcaacact cggcaaggcc ttttcaacaa   4620
ctctcaaggg agcccagaga ctggccgccc tcggcgacac agcctgggat ttcgggtcaa   4680
tcggcggggt gttcaactca atcgggaagg ctgtccacca ggtgttcggc ggagcctttc   4740
ggaccctgtt tgggggaatg tcttggatta ctcaggggct gatgggggct ctgcttcttt   4800
ggatgggcgt caacgcccgg gacaggagta tcgctctggc tttcctggcc acaggcgggg   4860
tgctcgtgtt tctggctacc aatgtccatg cttgatgact cgagctcaag cttcgaattc   4920
ccgataatca acctctggat tacaaaattt gtgaaagatt gactggtatt cttaactatg   4980
```

-continued ttgctccttt tacgctatgt ggatacgctg ctttaatgcc tttgtatcat gctattgctt 5040
cccgtatggc tttcattttc tcctccttgt ataaatcctg gttgctgtct ctttatgagg 5100
agttgtggcc cgttgtcagg caacgtggcg tggtgtgcac tgtgtttgct gacgcaaccc 5160
ccactggttg gggcattgcc accacctgtc agctcctttc cgggactttc gctttccccc 5220
tccctattgc cacggcggaa ctcatcgccg cctgccttgc ccgctgctgg acaggggctc 5280
ggctgttggg cactgacaat tccgtggtgt tgtcggggaa gctgacgtcc tttccatggc 5340
tgctcgcctg tgttgccacc tggattctgc gcgggacgtc cttctgctac gtcccttcgg 5400
ccctcaatcc agcggacctt ccttcccgcg gcctgctgcc ggctctgcgg cctcttccgc 5460
gtcttcgcct tcgccctcag acgagtcgga tctccctttg ggccgcctcc ccgcatcggg 5520
aattctgcag tcgacggtac ctttaagacc aatgacttac aaggcagctg tagatcttag 5580
ccacttttta aaagaaaagg ggggactgga agggctaatt cactcccaac gaagacaaga 5640
tcgtcgagag atgctgcata taagcagctg ctttttgctt gtactgggtc tctctggtta 5700
gaccagatct gagcctggga gctctctggc taactaggga acccactgct taagcctcaa 5760
taaagcttgc cttgagtgct tcaagtagtg tgtgcccgtc tgttgtgtga ctctggtaac 5820
tagagatccc tcagaccctt ttagtcagtg tggaaaatct ctagca 5866

<210> SEQ ID NO 35
<211> LENGTH: 5722
<212> TYPE: DNA
<213> ORGANISM: Artificial Sequence
<220> FEATURE:
<223> OTHER INFORMATION: recombinant lentiviral backbone TRIPdeltaU3.CMV/JEV.prMEdeltaTM

<400> SEQUENCE: 35
tggaagggct aattcactcc caacgaagac aagatatcct tgatctgtgg atctaccaca 60
cacaaggcta cttccctgat tagcagaact acacaccagg gccagggatc agatatccac 120
tgacctttgg atggtgctac aagctagtac cagttgagcc agagaagtta gaagaagcca 180
acaaaggaga gaacaccagc ttgttacaac ctgtgagcct gcatgggatg gatgacccgg 240
agagagaagt gttagagtgg aggtttgaca gccgcctagc atttcatcac ggtggcccga 300
gagctgcatc cggagtactt caagaactgc tgatatcgag cttgctacaa gggactttcc 360
gctgggggac tttccaggga ggcgtggcct gggcgggact ggggagtggc gagccctcag 420
atcctgcata taagcagctg ctttttgcct gtactgggtc tctctggtta gaccagatct 480
gagcctggga gctctctggc taactaggga acccactgct taagcctcaa taaagcttgc 540
cttgagtgct tcaagtagtg tgtgcccgtc tgttgtgtga ctctggtaac tagagatccc 600
tcagaccctt ttagtcagtg tggaaaatct ctagcagtgg cgcccgaaca gggacttgaa 660
agcgaaaggg aaaccagagg agctctctcg acgcaggact cggcttgctg aagcgcgcac 720
ggcaagaggc gaggggcggc gactggtgag tacgccaaaa attttgacta gcggaggcta 780
gaaggagaga gatgggtgcg agagcgtcag tattaagcgg gggagaatta gatcgcgatg 840
ggaaaaaatt cggttaaggc cagggggaaa gaaaaaatat aaattaaaac atatagtatg 900
ggcaagcagg gagctagaac gattcgcagt taatcctggc ctgttagaaa catcagaagg 960
ctgtagacaa atactgggac agctacaacc atcccttcag acaggatcag aagaacttag 1020
atcattatat aatacagtag caaccctcta ttgtgtgcat caaaggatag agataaaaga 1080
caccaaggaa gctttagaca agatagagga agagcaaaac aaaagtaaga ccaccgcaca 1140

```
gcaagcggcc gctgatcttc agacctggag gaggagatat gagggacaat tggagaagtg   1200
aattatataa atataaagta gtaaaaattg aaccattagg agtagcaccc accaaggcaa   1260
agagaagagt ggtgcagaga gaaaaaagag cagtgggaat aggagctttg ttccttgggt   1320
tcttgggagc agcaggaagc actatgggcg cagcgtcaat gacgctgacg gtacaggcca   1380
gacaattatt gtctggtata gtgcagcagc agaacaattt gctgagggct attgaggcgc   1440
aacagcatct gttgcaactc acagtctggg gcatcaagca gctccaggca agaatcctgg   1500
ctgtggaaag atacctaaag gatcaacagc tcctggggat ttggggttgc tctggaaaac   1560
tcatttgcac cactgctgtg ccttggaatg ctagttggag taataaatct ctggaacaga   1620
tttggaatca cacgacctgg atggagtggg acagagaaat taacaattac acaagcttaa   1680
tacactcctt aattgaagaa tcgcaaaacc agcaagaaaa gaatgaacaa gaattattgg   1740
aattagataa atgggcaagt ttgtggaatt ggtttaacat aacaaattgg ctgtggtata   1800
taaaattatt cataatgata gtaggaggct tggtaggttt aagaatagtt tttgctgtac   1860
tttctatagt gaatagagtt aggcagggat attcaccatt atcgtttcag acccacctcc   1920
caaccccgag gggacccgac aggcccgaag gaatagaaga agaaggtgga gagagagaca   1980
gagacagatc cattcgatta gtgaacggat ctcgacggta tcgccgaatt cacaaatggc   2040
agtattcatc cacaatttta aaagaaaagg ggggattggg gggtacagtg caggggaaag   2100
aatagtagac ataatagcaa cagacataca aactaaagaa ttacaaaaac aaattacaaa   2160
aattcaaaat tttcgggttt attacaggga cagcagagat ccactttggc tgatacgcgt   2220
ggagttccgc gttacataac ttacggtaaa tggcccgcct ggctgaccgc ccaacgaccc   2280
ccgcccattg acgtcaataa tgacgtatgt tcccatagta acgccaatag ggactttcca   2340
ttgacgtcaa tgggtggagt atttacggta aactgcccac ttggcagtac atcaagtgta   2400
tcatatgcca agtacgcccc ctattgacgt caatgacggt aaatggcccg cctggcatta   2460
tgcccagtac atgaccttat gggactttcc tacttggcag tacatctacg tattagtcat   2520
cgctattacc atggtgatgc ggttttggca gtacatcaat gggcgtggat agcggtttga   2580
ctcacgggga tttccaagtc tccaccccat tgacgtcaat gggagtttgt tttggcacca   2640
aaatcaacgg gactttccaa aatgtcgtaa caactccgcc ccattgacgc aaatgggcgg   2700
taggcgtgta cggtgggagg tctatataag cagagctcgt ttagtgaacc gtcagatcgc   2760
ctggagacgc catccacgct gttttgacct ccatagaaga caccgcgatc ggatccgcca   2820
ccatgggcgg aaacgaaggg tccattatgt ggctcgcctc cctggccgtg gtgatcgcct   2880
gcgccggagc aatgaagctg tccaactttc aggggaagct gctcatgaca attaacaaca   2940
ctgatattgc cgatgtcatt gtcatcccta catccaaggg cgaaaaccgg tgctgggtcc   3000
gggccatcga cgtcgggtac atgtgcgaag ataccattac atacgaatgc cccaagctga   3060
ccatgggaaa cgatcctgag gacgtggatt gctggtgcga caaccaggag gtgtacgtgc   3120
agtacgggcg gtgcacaagg acacggcact ccaagcgctc tcggcggagc gtgtccgtgc   3180
agacccacgg cgagtcttct ctcgtcaaca agaaggaggc atggctggat agcactaagg   3240
ccacccgcta cctcatgaag actgagaact ggatcattcg gaaccctgga tacgcttttc   3300
tggctgccgt gctggggtgg atgctgggga gcaacaacgg acagcgcgtg gtcttcacca   3360
ttcttctctt gttggtcgct cctgcttaca gctttaactg cttgggcatg ggcaacaggg   3420
atttcatcga gggcgcctcc ggggcaacct gggtggattt ggtgctcgaa ggagacagct   3480
```

```
gcctcaccat catggccaac gacaagccca ccctcgacgt gaggatgatc aacatcgagg   3540
cttcccaact ggccgaggtc agaagctact gttaccatgc cagcgtgaca gatatttcca   3600
cagtggctag gtgcccaact acaggcgagg cccacaacga gaaaagggct gatagtagct   3660
atgtctgtaa acagggcttt accgatcggg ggtggggcaa cgggtgtggg ctgttcggga   3720
aggggtccat tgatacctgt gctaagttca gttgcacttc caaggccatc ggcaggacaa   3780
ttcagcctga gaatattaag tacgaggtcg gcatctttgt gcacgggaca accacaagcg   3840
agaaccacgg gaactactcc gctcaagtgg gcgccagcca ggccgccaag tttacagtga   3900
ctcccaacgc ccccagtatt actctgaagc tgggagacta tggcgaggtg accctggatt   3960
gcgagcccag atccggcctg aacaccgagg ctttttacgt gatgacagtc ggctccaaga   4020
gtttcttggt gcacagggag tggtttcacg acctcgctct cccctggaca agcccctcct   4080
caactgcttg gagaaacaga gagctcctga tggagttcga agaggctcat gccactaagc   4140
agagcgtcgt ggcattgggg agtcaggaag gcggactcca ccaggccctt gccggagcca   4200
tcgtggtcga gtacagctca agcgtgaagt tgaccagtgg acacctgaag tgtagactga   4260
agatggacaa actggctctg aaggggacaa catacggcat gtgcaccgag aagttcagct   4320
tcgccaaaaa tcccgcagac accgggcatg ggacagtcgt catcgagctt agctacagcg   4380
gctccgacgg accatgcaag attccaattg tgagcgtggc ctctctcaac gatatgactc   4440
ccgtgggccg gctggtgact gtgaacccat tcgtggccac ttccagcgct aacagcaagg   4500
tgttggtgga gatggagcca cctttcgggg acagctatat tgtggtgggg cggggagaca   4560
aacagatcaa ccatcattgg cacaaggccg ggtcaacact cggcaaggcc ttttcaacaa   4620
ctctcaaggg agcccagaga ctggccgccc tcggcgacac agcctgggat ttcgggtcaa   4680
tcggcggggt gttcaactca atcgggaagg ctgtccacca ggtgttcggc ggagcctttc   4740
ggaccctgtg atgactcgag ctcaagcttc gaattcccga taatcaacct ctggattaca   4800
aaatttgtga aagattgact ggtattctta actatgttgc tccttttacg ctatgtggat   4860
acgctgcttt aatgcctttg tatcatgcta ttgcttcccg tatggctttc attttctcct   4920
ccttgtataa atcctggttg ctgtctcttt atgaggagtt gtggcccgtt gtcaggcaac   4980
gtggcgtggt gtgcactgtg tttgctgacg caacccccac tggttggggc attgccacca   5040
cctgtcagct cctttccggg actttcgctt tccccctccc tattgccacg gcggaactca   5100
tcgccgcctg ccttgcccgc tgctggacag gggctcggct gttgggcact gacaattccg   5160
tggtgttgtc ggggaagctg acgtcctttc catggctgct cgcctgtgtt gccacctgga   5220
ttctgcgcgg gacgtccttc tgctacgtcc cttcggccct caatccagcg gaccttcctt   5280
cccgcggcct gctgccggct ctgcggcctc ttccgcgtct tcgccttcgc cctcagacga   5340
gtcggatctc cctttgggcc gcctccccgc atcgggaatt ctgcagtcga cggtaccttt   5400
aagaccaatg acttacaagg cagctgtaga tcttagccac tttttaaaag aaaagggggg   5460
actggaaggg ctaattcact cccaacgaag acaagatcgt cgagagatgc tgcatataag   5520
cagctgcttt ttgcttgtac tgggtctctc tggttagacc agatctgagc ctgggagctc   5580
tctggctaac tagggaaccc actgcttaag cctcaataaa gcttgccttg agtgcttcaa   5640
gtagtgtgtg cccgtctgtt gtgtgactct ggtaactaga gatccctcag acccttttag   5700
tcagtgtgga aaatctctag ca                                            5722
```

<210> SEQ ID NO 36
<211> LENGTH: 24

```
<212> TYPE: DNA
<213> ORGANISM: Artificial Sequence
<220> FEATURE:
<223> OTHER INFORMATION: Primer

<400> SEQUENCE: 36

ctcgagttta ctccctatca gtga                                          24

<210> SEQ ID NO 37
<211> LENGTH: 36
<212> TYPE: DNA
<213> ORGANISM: Artificial Sequence
<220> FEATURE:
<223> OTHER INFORMATION: Primer

<400> SEQUENCE: 37

tcacacagat aaacttctcg gttcactaaa cgagct                             36

<210> SEQ ID NO 38
<211> LENGTH: 36
<212> TYPE: DNA
<213> ORGANISM: Artificial Sequence
<220> FEATURE:
<223> OTHER INFORMATION: Primer

<400> SEQUENCE: 38

agctcgttta gtgaaccgag aagtttatct gtgtga                             36

<210> SEQ ID NO 39
<211> LENGTH: 22
<212> TYPE: DNA
<213> ORGANISM: Artificial Sequence
<220> FEATURE:
<223> OTHER INFORMATION: Primer

<400> SEQUENCE: 39

tgataagagc cagcacgaat cg                                            22

<210> SEQ ID NO 40
<211> LENGTH: 35
<212> TYPE: DNA
<213> ORGANISM: Artificial Sequence
<220> FEATURE:
<223> OTHER INFORMATION: Primer

<400> SEQUENCE: 40

gaagatctat gactaaaaaa ccaggagggc ccggt                              35

<210> SEQ ID NO 41
<211> LENGTH: 34
<212> TYPE: DNA
<213> ORGANISM: Artificial Sequence
<220> FEATURE:
<223> OTHER INFORMATION: Primer

<400> SEQUENCE: 41

ttctgcagtc aagcatgcac attggtcgct aaga                               34
```

LENTIVIRAL VECTOR-BASED JAPANESE ENCEPHALITIS IMMUNOGENIC COMPOSITION

The instant application contains a Sequence Listing which has been filed electronically in ASCII format and is hereby incorporated by reference in its entirety. Said ASCII copy, created on Feb. 19, 2020, is named 15531157.txt and is 72,018 bytes in size.

FIELD OF THE INVENTION

The present invention relates to a lentiviral vector-based Japanese encephalitis (JE) immunogenic composition. The present invention is directed to a recombinant lentiviral vector expressing the precursor of membrane (prM) and the envelope (E) protein, in particular glycoprotein of a Japanese encephalitis virus (JEV) or immunogenic fragments thereof. The present invention also provides cells expressing the lentiviral vector, uses and methods to prevent a JEV infection in a mammalian host, especially in a human or an animal host, in particular a pig or a piglet, preferably a domestic pig or a domestic piglet.

BACKGROUND OF THE INVENTION

Japanese encephalitis is due to an infection with the mosquito-borne Japanese encephalitis virus (JEV), a member of the *Flavivirus* genus in the Flaviviridae family (Go et al., 2014; Hubalek et al., 2014; Weaver and Barrett, 2004; Yun and Lee, 2014). JEV contains a positive single-stranded RNA genome encoding a polyprotein that is processed into three structural proteins, the capsid (C), the precursor of membrane (prM) and the envelope (E), and seven nonstructural proteins NS1 to NS5 (Yun and Lee, 2014). Viral assembly occurs in the lumen of endoplasmic reticulum membrane where the nucleocapsids associate with the heterodimers prME to form immature JEV virion. The latter transits through the secretory pathway, where the virion is matured through cleavage of prM into the membrane (M) protein by furin in the trans-Golgi (Yun and Lee, 2014). Additionally, like other Flaviviruses, JEV produces Virus-Like Particles (VLPs), which are assembled solely from prM and E proteins, and undergo the same maturation process as genuine viral particles (Kuwahara and Konishi, 2010). These VLPs can be produced in the absence of any other viral component and display similar biological activity as genuine virions (Kuwahara and Konishi, 2010).

JEV is usually maintained in an enzootic cycle between *Culex tritaeniorhynchus* mosquitoes and amplifying vertebrate hosts, such as waterbirds and domestic swine (Go et al., 2014; Hubalek et al., 2014; Impoinvil et al., 2013). Horses and humans are thought to be dead-end hosts, since they do not develop a level of viremia sufficient to infect mosquitoes (Impoinvil et al., 2013). In the past decades, there has been an expansion of JEV geographic distribution in Asia and possible introduction of JEV in Europe has been recently documented (Campbell et al., 2011; Zeller 2012).

Phylogenetic studies based on the viral envelope protein sequences allow the division of JEV strains into genotypes G1 to G5 (Gao et al., 2014; Hubalek et al., 2014; Le Flohic et al., 2013; Schuh et al., 2013; Solomon et al., 2003; Weaver and Barrett, 2004). Initially, most of the circulating strains of JEV belong to G3 and were at the origin of major epidemics in Southeast Asian countries. Recently a shift in prevalence from JEV G3 to G1 has been observed in several Asian countries, while some strains of JEV G5 have been occasionally isolated in China and South Korea (Gao et al., 2013; Le Flohic et al., 2013; Li et al., 2014; Pan et al., 2011; Schuh et al., 2014; Takhampunya et al., 2011).

JEV is the etiologic agent of the most important viral encephalitis of medical interest in Asia, with an incidence of 50,000 cases and about 10,000 deaths per year (Campbell et al., 2011; Go et al., 2014; Yun and Lee, 2014). About 20 to 30% of the symptomatic human cases are fatal, while 30 to 50% of no lethal cases can develop long-term neurologic sequelae. No antiviral treatment is available for JE disease. Vaccines against JEV are currently available to humans and for some animals such as horses and swine: those are inactivated mouse brain-derived, inactivated cell culture derived, live-attenuated and live-attenuated chimeric yellow fever virus-JEV vaccines (Bonaparte et al., 2014; Dubischar-Kastner and Kanesan-Thasna, 2012; Erra et al., 2013; Fan et al., 2013; Halstead and Thomas, 2011; Impoinvil et al., 2013; Ishikawa et al., 2014; Marks et al., 2012; Song et al., 2012; Yang et al., 2014; Yun and Lee, 2014). However, some of them lack of long-term immunity and live-attenuated vaccine strains carry a possible risk of reversion to virulence (Yun and Lee, 2014). Also the cost effectiveness of JEV vaccines is considered as a major obstacle (Impoinvil et al., 2013).

Lentiviral vectors represent a novel and attractive platform for gene-based immunization. The ability of lentiviral vectors to efficiently transduce non-dividing dendritic cells (DCs) allows a prolonged antigen presentation through the endogenous pathway, which in turns translates into the induction of strong, multi-epitopic and long lasting humoral as well as cellular immune responses. Consequently, an increasing number of pre-clinical studies show a great vaccine efficacy of lentiviral vectors in both infectious diseases and anti-tumor vaccination fields (Beignon et al., 2009; Di Nunzio et al., 2012; Fontana et al., 2014; Grasso et al., 2013; Hu et al., 2011; Sakuma et al., 2012). The inventors previously demonstrated that both integrative and non-integrative lentiviral vectors are promising vaccination vectors against arboviruses such as West Nile virus (WNV) that belongs to the JE serocomplex of *Flavivirus* genus (Coutant et al., 2008; Iglesias et al., 2006). These reports represented the first demonstration of the ability of lentiviral vectors for eliciting a protective antibody response against an infectious pathogen. Indeed immunization with a single minute dose of recombinant lentiviral TRIP vectors that express the soluble form of WNV E protein confers a robust sterilizing protection against a lethal challenge with WNV in mice (Coutant et al., 2008; Iglesias et al., 2006). Humoral immunity plays a pivotal role in protecting from JEV infection (Konishi, 2013; Dubischar-Kastner and Kanesan-Thasna, 2012) and consequently, the elicitation of protective antibody response is critical in the development of safe JEV vaccines (Larena et al., 2013).

International patent application WO2005/111221 relates to a recombinant lentiviral vector for expression of a protein of a Flaviviridae and to its applications as a vaccine. In particular it describes the use of a recombinant lentiviral vector comprising a polynucleotide fragment encoding at least one protein of a virus of the family Flaviviridae or an immunogenic peptide of at least 8 amino acids of said protein, for preparing an immunogenic composition intended for the prevention and/or the treatment of a Flaviviridae infection in a sensitive species.

International patent application WO2007/052165 relates to the use of a lentiviral vector comprising a heterologous nucleic acid encoding an antigen, and wherein expression of the antigen in a cell of an animal elicits a humoral response in said animal, for the preparation of a medicament able to produce antibodies when administered to said animal. For example, expression of the antigen induces protective immunity against a *flavivirus*, i.e. WNV.

International patent application WO2009/019612 relates to lentiviral gene transfer vectors and to their medicinal application. These vectors may be used to elicit an immune response to prevent or to treat a pathogenic state, including virus infections, parasite and bacterial infections or cancers. Said lentiviral vector can comprise a polynucleotide encoding at least one antigenic polypeptide derived from a *flavivirus*, for example from JEV.

International patent application WO2005/065707 relates to two recombinant adenoviruses (RAds), namely RAdEa expressing prM and the membrane-anchored E protein (Ea) of JEV, and RAdEs expressing prM and the secretory E protein (Es) of JEV. Plasmids pMEa and pMEs containing the cDNAs encoding prM and said Ea or Es of JEV have been described by Kaur et al. (2002).

Having considered the persistent need for a vaccine providing a protective humoral immune response against a JEV infection including against multiple JEV genotypes, the inventors have designed a novel lentivirus vector expressing JEV selected proteins that proved to elicit a protective immune response against one or more JEV of different genotypes. The obtained results show that recombinant TRIP vectors expressing JEV prM and E proteins may prime and boost antigen-specific humoral broadly neutralizing responses in vaccinated mice.

DESCRIPTION OF THE INVENTION

The present invention relates to a recombinant lentiviral vector genome comprising lentiviral cis-active elements including long terminal repeats (LTRs), or modified LTRs including partially deleted of most of the U3 region in the 3'LTR, psi (ψ) packaging signal, Rev responsive element (RRE) and DNA flap central polypurine tract (cPPT)/central termination sequence (CTS), together with a transcription unit encoding the precursor of membrane (prM) protein and the envelope (E) protein of a Japanese encephalitis virus (JEV), or immunogenic fragments thereof. In addition, the vector genome may comprise a WPRE sequence of lentiviral origin.

In a preferred embodiment of the invention, the sequences of the lentivirus contained in the lentiviral vector genome encompass the following cis-active sequences: HIV1-5'LTR (positions 1-636, disclosed as SEQ ID NO: 26), RRE (positions 1301-1534, disclosed as SEQ ID NO: 27), CPPT-CTS (positions 2056-2179, disclosed as SEQ ID NO: 28), WPRE (positions 4916-5520 in the vector genome recombined with the polynucleotide encoding prME or positions 4772-5376 in the vector genome recombined with the polynucleotide encoding prME$^{\Delta TM}$, disclosed as SEQ ID NO: 30), HIV1-3'LTR (positions 5605-5866 in the vector genome recombined with the polynucleotide encoding prME or positions 5461-5722 in the vector genome recombined with the polynucleotide encoding prME$^{\Delta TM}$, disclosed as SEQ ID NO: 31). Advantageously, the vector genome is devoid of sequences that encode functional structural proteins of the lentivirus.

As used herein, the term "recombinant lentiviral vector genome" refers to a polynucleotide construct which is transferred in a host cell as a result of transfection of said host cells with a plasmid (transfer vector) which is recombined with said construct or as a result of transduction of a host cell with a vector particles that comprise said vector genome as their genome.

The expression «E protein» qualifies, according to the invention, the full-length protein or glycoprotein as expressed from the genome of a JEV and also encompasses the variant of this protein or glycoprotein consisting of its soluble form, i.e., the protein/glycoprotein modified with respect to the full-length protein by deletion of its two transmembrane (TM) domains. Thus unless otherwise stated in the present application, the full-length protein/glycoprotein and the soluble protein/glycoprotein are similarly concerned by the disclosed embodiments.

"Immunogenic fragments thereof" refers to a portion of the prM or the E protein of JEV, wherein said portion comprises B epitopes which elicit an antibody response, when expressed by the recombinant lentiviral vector of the invention.

The present invention also relates to a recombinant lentiviral vector genome consisting of lentiviral cis-active elements including LTRs, or modified LTRs including partially deleted 3'LTR, ψ packaging signal, RRE and DNA flap cPPT/CTS, together with a transcription unit encoding the prM and the E protein of a JEV, or immunogenic fragments thereof.

According to the invention, the transcription unit comprises a polynucleotide encoding said proteins of a JEV type 3, for example the JEV RP9 strain or the JEV of the Nakayama strain.

In a particular embodiment, the transcription unit is a codon-optimized sequence based on the sequences encoding the prM and the E protein, wherein codon-optimization has been performed to improve the level of expression of these JEV proteins in a mammalian host cell, in particular in a human cell. The skilled person knows how to achieve codon-optimization for expression in mammalian cells and specific examples of codon-optimized sequences are disclosed in the present application.

In a particular embodiment, the native and codon-optimized nucleotide sequences of the polynucleotide encoding the signal peptide for prM as well as the amino acid sequence of the signal peptide for prM used in the invention are the sequences disclosed as SEQ ID No: 1, SEQ ID No: 2 and SEQ ID No: 3 respectively.

In a particular embodiment, the native and codon-optimized nucleotide sequences of the polynucleotide encoding the full-length prM protein as well as the amino acid sequence of the full-length prM protein used in the invention are the sequences disclosed as SEQ ID No: 4, SEQ ID No: 5 and SEQ ID No: 6 respectively.

In a preferred embodiment, the E protein is either the full-length E protein. In another embodiment, the E protein is the soluble form (sE or E$^{\Delta TM}$) lacking the two C-terminal transmembrane domains of the full-length E protein. The obtained protein may be a glycoprotein when expressed in a determined host cell. Glycosylation may be different depending on the cell expressing the E protein.

In a particular embodiment, the native and codon-optimized nucleotide sequences of the polynucleotide encoding the full-length E protein as well as the amino acid sequence of the full-length E protein of the invention are the sequences disclosed as SEQ ID No: 7, SEQ ID No: 8 and SEQ ID No: 9 respectively.

In a particular embodiment, the native and codon-optimized nucleotide sequences of the polynucleotide encoding the soluble form of the full-length E protein lacking the two C-terminal transmembrane domains as well as the amino acid sequence soluble form of the full-length E glycoprotein lacking the two C-terminal transmembrane domains of the invention are the sequences disclosed as SEQ ID No: 10, SEQ ID No: 11 and SEQ ID No: 12 respectively.

In a particular embodiment, the native and codon-optimized nucleotide sequences of the polynucleotide encoding the first transmembrane domain (TMD1) as well as the amino acid sequence of the first transmembrane domain (TMD1) of the E protein are the sequences disclosed as SEQ ID No: 13, SEQ ID No: 14 and SEQ ID No: 15 respectively.

In a particular embodiment, the native and codon-optimized nucleotide sequences of the polynucleotide encoding the second transmembrane domain (TMD2) as well as the amino acid sequence of the second transmembrane domain (TMD2) of the E protein are the sequences disclosed as SEQ ID No: 16, SEQ ID No: 17 and SEQ ID No: 18 respectively.

In a preferred embodiment, the polynucleotide encoding the prM protein has the sequence of SEQ ID NO: 5 and the polynucleotide encoding the E protein has the sequence of SEQ ID NO: 8 or SEQ ID NO: 11.

In a particular embodiment, the native and codon-optimized nucleotide sequences of the polynucleotide encoding the prM protein and the full-length E protein (the prM-E protein) as well as the amino acid sequence of the prM-E protein of the invention are the sequences disclosed as SEQ ID No: 19, SEQ ID No: 20 and SEQ ID No: 21 respectively.

In a particular embodiment, the native and codon-optimized nucleotide sequences of the polynucleotide encoding the prM protein and the soluble form of the full-length E protein lacking the two C-terminal transmembrane domains (the prME$^{\Delta TM}$ protein) as well as the amino acid sequence of the prM-soluble form of the E protein lacking the two C-terminal transmembrane domains (the prME$^{\Delta TM}$ protein) of the invention are the sequences disclosed as SEQ ID No: 22, SEQ ID No: 23 and SEQ ID No: 24 respectively.

In a preferred embodiment of the invention, the prM protein and the E protein either full-length or soluble are those of the JEV of genotype 3.

In a particular embodiment, the present invention relates to a recombinant lentiviral vector genome, wherein a JEV providing the prM and E proteins is a JEV of genotype 3 (G3) such as the strain RP-9.

As used herein, the term “encoding” defines the ability of a nucleic acid molecule to be transcribed and where appropriate translated for product expression into selected cells or cell lines, when said molecule is placed under expression control sequences including promoter for transcription. Accordingly a “polynucleotide encoding” according to the invention designates the nucleic acid having the sequence translated into the amino acid sequence and that may be cloned or placed under the control of expression control sequences, especially a heterologous promoter to provide a transcription unit.

In a particular embodiment, the present invention relates to a recombinant lentiviral vector genome, which can be derived from an Human Immunodeficiency Virus (HIV), for example HIV-1 or HIV-2, Caprine Arthritis Encephalitis Virus (CAEV), Equine Infectious Anaemia Virus (EIAV), VISNA, Simian Immunodeficiency Virus (SIV), Feline Immunodeficiency Virus (FIV) or Bovine Immunodeficiency Virus (BIV).

In a preferred embodiment, the lentiviral vector genome is derived from the genome of HIV, especially of HIV-1.

In another preferred embodiment, the lentiviral vector genome is derived from the genome of FIV.

The lentiviral-based vectors according to the invention are replacement vectors, meaning that the sequences of the original lentivirus genome encoding the lentiviral proteins are essentially deleted in the genome of the vector resulting in a lack of expression of any viral protein from the parental lentivirus.

According to another particular embodiment, the recombinant lentiviral vector genome is replication-incompetent as a result of lack of expression of any lentiviral protein, i.e. as a result of deletion of all or part of the gag and pol genes of the lentiviral genome or mutation in the gag and pol genes of the lentiviral genome, so that the gag and pol genes are not capable of encoding functional GAG and POL proteins.

The vector genome as defined herein is devoid of the structural genes of the lentivirus or devoid of parts of all the structural genes of the lentivirus, thereby preventing expression of the structural proteins from its sequence. As a consequence, the vector genome when recombined with a DNA plasmid is a transfer vector.

Accordingly, a vector genome may be a replacement vector in which all the viral protein coding sequences between the 2 LTRs have been deleted and replaced by the recombinant polynucleotide encoding the polypeptide of JEV, and wherein the DNA flap element has been re-inserted in association with the required cis-acting sequences described herein. Further features relating to the composition of the vector genome are disclosed in relation to the preparation of the particles.

In a preferred embodiment, in said vector genome, the 3' LTR sequence of the lentiviral vector genome is devoid of at least the activator (enhancer) and of the promoter of the U3 region. In another particular embodiment, the 3' LTR region is devoid of the U3 region (delta U3). In this respect, reference is made to the corresponding description in WO 01/27300 and WO 01/27304.

In a particular embodiment, in the vector genome, the U3 region of the LTR 5' is replaced by a non lentiviral U3 or by a promoter suitable to drive tat-independent primary transcription. In such a case, the vector is independent of tat transactivator.

The vector genome also comprises the psi (ψ) packaging signal. The packaging signal includes a sequence coding the N-terminal fragment (about 15-30 AA) of the gag ORF. In a particular embodiment, its sequence could be modified by frameshift mutation(s) or a mutation in ATG initiation codon in order to prevent any interference of a possible transcription/translation of gag peptide, with that of the transcription unit.

The vector genome may optionally also comprise elements selected among a splice donor site (SD), a splice acceptor site (SA) and/or a RRE.

A lentiviral-based vector encompassing the vector genome of the invention and comprising a DNA flap is according to the invention, a so-called TRIP-based vector.

The structure and composition of the vector genome used to prepare the lentiviral vectors of the invention are based on the principles described in the art and on examples of such lentiviral vectors primarily disclosed in (Zennou et al, 2000; Firat H. et al, 2002; VandenDriessche T. et al, 2002). For example, pTRIP[delta]U3 CMV-GFP has been deposited on Oct. 11, 1999 at the CNCM under number I-2330 (Institut Pasteur, 25-28 Rue du Docteur Roux, 75724, PARIS Cedex 15, France). Reference is also made to the disclosure, including to the deposited biological material, in patent applications WO 99/55892, WO 01/27300 and WO 01/27304.

Nucleotide sequence of DNA flap lentiviral origin comprising two essential regions, i.e., the cPPT and the CTS regions, wherein the cPPT and CTS regions induce a threestranded DNA structure during replication of DNA containing them (previously defined in Zennou et al., *Cell,* 2000, 101, 173-185; and in the international patent applications WO99/55892 and WO01/27300).

In a particular embodiment, the DNA flap is inserted upstream of the polynucleotide of interest, advantageously but not necessarily to be located in an approximate central position in the vector genome. A DNA flap suitable for the invention may be obtained from a lentivirus, in particular a human lentivirus.

It may be alternatively obtained from the CAEV (Caprine Arthritis Encephalitis Virus) virus, the EIAV (Equine Infectious Anaemia Virus) virus, the VISNA virus, the SIV (Simian Immunodeficiency Virus) virus or the FIV (Feline Immunodeficiency Virus) virus. The DNA flap may be either prepared synthetically (chemical synthesis) or by amplification of the DNA providing the DNA flap from the appropriate source as defined above such as by Polymerase chain reaction (PCR). In a more preferred embodiment, the DNA flap is obtained from an HIV retrovirus, for example HIV-1 or HIV-2 virus including any isolate of these two types.

As defined above, the present invention relates to a recombinant lentiviral vector genome which further comprises a polynucleotide which is placed under the control of a heterologous promoter (i.e. a promoter which does not derive from the lentiviral genome providing the cis-active sequences), thereby providing a transcription unit. The promoter may advantageously be one that favors the B cell response. A particular promoter is the cytomegalovirus immediate early (CMVie) promoter having the sequence of SEQ ID NO: 29. Other promoters may in particular be selected for their properties as constitutive promoters, tissue-specific promoters, or inducible promoters. Examples of suitable promoters encompass the promoters of the following genes: EF1$\alpha$, human PGK, PPI (preproinsulin), thiodextrin, Ferritin L chain or Ferritin H chain, Chymosin beta 4, Chymosin beta 10, Cystatin Ribosomal Protein L41, CAG, SV40 or MND.

Accordingly, in another more particular embodiment, the present invention relates to a recombinant lentiviral vector as defined herein, the genome of which comprises a 3'-LTR in which the promoter and the activator of the U3 region have been deleted and a polynucleotide encoding the prM and E proteins which is placed under the control of a heterologous promoter, to form a transcription unit.

The thus obtained vector genome is recombined with or cloned in a plasmid vector to be used as a transfer vector.

Accordingly, in a particular embodiment, the present invention relates to a recombinant lentiviral transfer vector, which is a TRIP-based vector.

In a particular embodiment of the invention, the genome vector is accordingly provided as a pTRIP plasmid as disclosed herein, which is an HIV1-based vector including a DNA flap sequence as defined above and in Iglesias, M. C et al. (*J. Gene Med.,* 2006, 8: 265-274).

In another particular embodiment of the invention, the genome vector is provided as a pTRIP plasmid which is an FIV-based vector including a DNA-Flap sequence issued from an FIV.

Preferably, the present invention relates to a recombinant lentiviral transfer vector pTRIPΔU3.CMV wherein a polynucleotide encoding the prM and the E proteins (either full-length or soluble E, sE) of a JEV is cloned, and relates to recombinant lentiviral vector particles obtained with it.

In a particular embodiment, the present invention relates to a recombinant lentiviral transfer vector, pTRIPΔU3.CMV/JEV.prME vector whose recombinant lentiviral backbone has the nucleic acid sequence is as defined in SEQ ID NO: 34, and relates to recombinant lentiviral vector particles obtained with it.

In another particular embodiment, the present invention relates to a recombinant lentiviral transfer vector, pTRIPΔU3.CMV/JEV.prME$^{\Delta TM}$ vector whose recombinant lentiviral backbone has the nucleic acid sequence is as defined in SEQ ID NO: 35, and relates to recombinant lentiviral vector particles obtained with it.

In a particular embodiment, in the above construct used for the preparation of the recombinant lentiviral vector genome of the invention, the CMV promoter of the transfer vector is replaced by a promoter disclosed in the above list.

The present invention also relates to a DNA plasmid comprising the recombinant lentiviral vector genome of the invention.

The present invention also relates to a host cell either transfected or genetically transformed with a DNA plasmid comprising the recombinant lentiviral vector genome of the invention (transfer vector).

The present invention also relates to a host cell either transfected or genetically transformed with the recombinant lentiviral transfer vector of the invention and with additional plasmid vectors for packaging and for expression of the envelope for pseudotyping.

The host cell of the invention is transfected with these vectors by methods well known to the person skilled in the art, i.e. by chemical transfection (calcium phosphate, lipofectamine), lipid-based techniques (liposome), electroporation, photoporation, . . . .

As used herein, the term "transfected" refers to a cell comprising a recombinant lentiviral transfer vector of the invention (transient expression), whereas the term "genetically transformed" refers to a cell whose genome has been definitively modified by a polynucleotide of the invention (permanent expression).

Said transitory or stably transformed cells can be any prokaryotic (bacteria) or eukaryotic (yeast, insect or animal including mammal especially human) cells. In an embodiment, cells are non-human cells. In a particular embodiment, cells of the invention are isolated human cells, "isolated" meaning outside of their natural environment.

In a particular embodiment of the invention, the cell is HEK 293T (human embryonic kidney) cell line, in particular as disclosed in Zennou et al. (*Cell,* 2000, 101, 173-185).

A production cell for the expression of lentiviral vector particles which is either transfected or genetically transformed with a DNA plasmid according to the invention and with a DNA plasmid encoding a heterologous envelope protein, in particular an envelope protein of a VSV selected among VSV-G of Indiana strain, of VSV-G of New Jersey strain and packaging construct(s) as DNA plasmid(s) encoding the GAG and POL proteins of the lentivirus. The gene encoding the POL protein may be mutated to enable preparation of non-integrative lentiviral vectors.

The present invention also relates to recombinant lentiviral vector particles obtained using the transfer vector disclosed herein, in particular with pTRIPΔU3.CMV/JEV.prME vector and pTRIPΔU3.CMV/JEV.prME$^{\Delta TM}$ vector, and produced according to well-known methods and which are pseudotyped with at least one envelope protein of another virus.

The expressions "recombinant lentiviral vector" or "recombinant lentiviral vector particles" defines the obtained virus-like particles (VLPs) expressed in a host cell or production cells following transfection by the plasmid vectors consisting of the transfer vector, the envelope vector encoding the selected envelope protein and the packaging vector providing lentiviral proteins in trans (such as lentiviral GAG and POL proteins, in particular mutated POL protein for the avoidance of integration) according to methods well-known in the art.

The terms "recombinant lentiviral vector particles" encompass recombinant viral particles, and recombinant virus-like particles.

Virus-like particles result from incomplete assembly of the proteins present for encapsidation of the recombinant lentiviral genome in a way that does not enable the formation of true viral particles.

The lentiviral vector particles of the invention are formed from the transduction of lentiviral vectors of the invention into cells. These particles contain prM multimers non-covalently associated with the E protein corresponding to the cleavage product of the precursor prM.E into prM and E by enzymes from endoplasmic reticulum (signalases) at the level of the last 15 amino acids of the prM/M protein, i.e. WFTILLLLVAPAYS, whose amino acid sequence is as defined in SEQ ID NO: 25.

In another embodiment of the invention, the lentiviral vector particles express prM and sE proteins.

By contrast to what has been disclosed in Iglesias M. C. et al (2006), the inventors have observed that the expression of the E protein of JEV by the lentiviral vector particles does not effectively induce an antibody response in the host receiving the particles. Rather, they obtained effective antibody response when the E protein was co-expressed with the prM protein. A higher antibody response was obtained with the lentiviral vector particles encoding prME when compared to the results obtained with the lentiviral vector particles encoding prME$^{\Delta TM}$.

Said pseudotyping envelope protein may be the vesicular stomatitis virus glycoprotein G (VSV-G), which is a transmembrane protein that functions as the surface coat of the wild type viral particles. It is also a common coat protein for engineered lentiviral vectors.

Vesicular stomatitis Indiana virus (VSV-G IND) and Vesicular stomatitis New Jersey virus (VSV-NJV) are preferred viruses to pseudotype the lentiviral vector genomes of the invention. Their VSV-G proteins are disclosed in Genbank, where several strains are presented. For VSV-G New Jersey strain, reference is especially made to the sequence having accession number V01214. Other strains such as Isfahan, VSV-G CV, Cocal could alternatively be used.

The most preferred VSV-G is Vesicular stomatitis Indiana virus (VSV-G IND) having accession number AAA48370.1 in Genbank corresponding to strain JO2428.

According to another particular embodiment of the invention, the recombinant lentiviral vector particles are integration defective (or non-integrative) as a result of mutation or deletion in the pol gene of the lentivirus present on the plasmid vector providing the packaging construct. Suitable mutations enabling formation of integration defective particles are well-known in the art and illustrated in WO 2009/019612.

In a particular embodiment, the recombinant lentiviral vector particles are used as active ingredient in the prophylactic treatment against JEV infection in a mammal, either an animal or a human.

As defined herein, the term "animal" refers to a vertebrate host, preferably domestic animals and farmed animals. Preferred animal candidates for treatment with the recombinant lentiviral particles of the invention are pigs, in particular domestic pigs, birds, in particular ardeid birds and horses. A non-exhaustive list of targeted animals includes non-avian vertebrates, poultry, donkeys, cattle, including bovines, ovins, caprins, sheep, goats, wild mammals, reptiles, amphibians, chickens, ducks, geese, turkeys, rabbits, rodents, including hamsters, rats and mice, pets, including dogs and cats . . . .

In the most preferred embodiment, said animal is a pig or a piglet, in particular a domestic pig or a domestic piglet.

In another particular embodiment, the recombinant lentiviral vector particles are used as active ingredient and administered at a dose, either as a single dose or as multiple doses, suitable for the elicitation of an antibody response against JEV prM and/or E protein(s), especially a protective antibody response against JEV prM and/or E protein(s).

More particularly, the recombinant lentiviral vector particles are used as active ingredient in the prophylactic treatment against JEV infection in a mammal, either an animal or a human, wherein the treatment involves administering said recombinant lentiviral vector in a prime-boost regimen.

Preferably, said lentiviral vector particles for priming the immunological response and the lentiviral vector particles for boosting the response are pseudotyped with different non-cross reacting VSV-G envelope proteins as defined above, in particular are pseudotyped with the VSV-G protein of the Indiana VSV strain or with the VSV-G protein of the New-Jersey VSV strain.

In a particular embodiment, said recombinant lentiviral vector particles are used in the prophylactic treatment against infection by JEV of genotype G3.

In another embodiment, said recombinant lentiviral vector particles are used in the prophylactic treatment against infection by JEV of genotypes G1 and G3 or of genotypes G1, G3 and G5.

In a particular embodiment, the recombinant lentiviral vector particles of the invention elicit neutralizing antibodies against multiple JEV genotypes, in particular against G1 and G3 genotypes, or against G1, G3 and G5 genotypes.

The recombinant lentiviral vector particles of the invention are used for the preparation of an immunogenic composition for immunisation, in particular for prophylactic immunisation against a JEV infection in a mammalian host, especially in a human or an animal host.

In a particular embodiment, the recombinant lentiviral vector particles of the invention elicit a protective humoral immune response against JEV infection in a mammalian host, especially in a human or an animal host, i.e. elicits a protective antibody response against JEV infection, in particular elicit neutralizing antibodies in the host.

Although for obvious reason, the observation of this immune response has not yet been carried out in human being, the disclosed results on the animal host are highly in favour of similar expectation in human.

The particular lentiviral vector particles of the invention thus provide specific interesting candidates for prophylactic vaccination against JEV.

In a further aspect, the present invention relates to an immunogenic composition comprising the recombinant lentiviral vector particles according to the invention, in a dose sufficient to elicit an immune antibody response, which does or which does not comprise an accessory adjuvant.

The expression "immunogenic composition" refers to a composition comprising at least the lentiviral vector particles of the invention as active principle, said composition being suitable for administration into a host, in particular in a mammalian host, especially in a human or an animal host. This composition may comprise further a pharmaceutically suitable excipient or carrier and/or vehicle, when used for systemic or local administration. A "pharmaceutically acceptable carrier" refers to a non-toxic solid, semisolid or liquid filler, diluent, encapsulating material or formulation auxiliary of any conventional type. A "pharmaceutically acceptable carrier" is non-toxic to recipients at the dosages and concentrations employed and is compatible with other ingredients of the formulation; suitable carriers include, but are not limited to, phosphate buffered saline solutions, distilled water, emulsions such as an oil/water emulsions, various types of wetting agents sterile solutions and the like, dextrose, glycerol, saline, ethanol, and combinations thereof.

In a preferred embodiment of the invention, the immunogenic composition is in freeze-dried form, the freeze-drying being carried out in the presence of cryoprotective compounds such as trehalose (Bieganski et al. *Biotechnol Prog,* 1998, 14, 615-620).

The immunogenic composition of the invention has the capacity to elicit an immune response i.e., any reaction by the immune system of the host against said at least one polypeptide (encoded by said transcription unit), in particular by elicitation of antibody response. Lentiviral vectors of the invention which are integration-defective have also shown their capacity to elicit antibodies in the host.

As defined herein, the immune response encompasses a humoral response i.e., antibodies, elicited by said composition, that are produced against said at least one JEV polypeptide expressed by the lentiviral vector genome. In a particular embodiment, said humoral response is a protective humoral response. The protective humoral response results mainly in maturated antibodies, having a high affinity for their antigen, such as IgG. In a particular embodiment, the protective humoral response induces the production of neutralizing antibodies.

In a particular embodiment of the invention, the lentiviral vector genome of the invention, despite the defective integrase, is able to elicit an early immune response, especially to induce antibody response. The expression "early immune response" refers to a protective immune response (protection against the JEV infection) that is conferred within about one week after the "boost" administration of the composition.

In another embodiment, the immune response conferred by the composition of the invention is a long lasting immune response i.e., said immune response can be still detected at least two months, preferably at least 3 months and most preferably at least 6 months after the administration of the composition. When the immune response is humoral, the long lasting response can be shown by the detection of specific antibodies, by any suitable methods such as ELISA, immunofluorescence (IFA), focus reduction neutralization tests (FRNT), immunoprecipitation, or Western blotting.

In another embodiment, independent of the above-embodiment, the strength of the immune response conferred by the composition of the invention is dependent upon the injected doses of the lentiviral vectors.

Interestingly, said immune response, early immune response and/or long lasting immune response, is elicited with the non-integrative gene transfer vector, after a single prime-boost administration of the composition of the invention.

The present invention also relates to a vaccine composition comprising the recombinant lentiviral vector particles according to the invention expressing the defined JEV proteins, which does or which does not comprise an accessory adjuvant.

It is considered that the composition of the invention (in particular the recombinant lentiviral vector genome as defined herein or the recombinant lentiviral vector particles of the invention) has a protective capacity against JEV infection when after challenge of immunized host with JEV, it enables the delay and/or the attenuation of the symptoms usually elicited after infection with said JEV against which protection is sought by the administration of the composition of the invention, or when especially the JEV infection is delayed.

According to a particular embodiment of the invention, the immunogenic composition is formulated for an administration through parental route such as subcutaneous (s.c.), intradermal (i.d.), intramuscular (i.m.), intraperitoneal (i.p.) or intravenous (i.v.) injection.

The most preferred administration is the intramuscular (i.m.) injection.

According to another particular embodiment of the invention, the immunogenic composition is formulated for administration in one or multiple administration dose(s), in particular in a prime-boost administration regime.

As used herein, the term "prime-boost regimen" encompasses a first administration step eliciting an immune response and one or several later administration step(s) boosting the immune reaction.

Accordingly, an efficient prime-boost system can be used for iterative administration, enabling successively priming and boosting the immune response in a host, especially after injections in a host in need thereof. "Iterative" means that the active principle, i.e. the recombinant lentiviral particles of the invention, is administered twice or more to the host. The priming and boosting immunization can be administered to the host at different or identical doses, and injections can be administered at intervals of several weeks, in particular at intervals of four weeks or more.

In a particular embodiment, the immunogenic composition does not comprise an accessory adjuvant.

The quantity to be administered (dosage) depends on the subject to be treated, including the condition of the patient, the state of the individual's immune system, the route of administration and the size of the host. Suitable dosages range from $10^3$ TU (Transcription Units) to $10^7$ TU and can be modified by one skilled in the art, depending on circumstances.

Preferably, the immunogenic composition is administered in one administration dose and comprises a dose of recombinant lentiviral vector particles of the invention equivalent to 0.5 ng to 5000 ng, preferably 0.5 ng to 50 ng, and more preferably 50 to 500 ng.

The present invention also relates to an immunologically effective quantity of recombinant lentiviral vector particles according to the invention, or an immunogenic composition according to the invention, or a vaccine composition according to the invention, for use in prophylactic immunisation against JEV infection, in particular when JEV is of genotype 3 or 1 or 5, in a mammalian host, especially in a human or an animal host, wherein said particles or composition are in admixture with a pharmaceutically acceptable vehicle, and/or an adjuvant.

The present invention also relates to a method to protect against a JEV infection in a mammalian host, especially in a human or an animal host, comprising administering a pharmaceutically effective quantity of recombinant lentiviral vector particles according to the invention, or an immunogenic composition according to the invention, or a vaccine composition according to the invention, wherein said particles or composition are in admixture with a pharmaceutically acceptable vehicle, and/or an adjuvant.

As used herein, the expression "to protect against JEV infection" refers to a method by which a Japanese encephalitis virus infection is obstructed or delayed, especially when the symptoms accompanying or following the infection are attenuated, delayed or alleviated or when the infecting virus is cleared from the host.

As defined herein, a "pharmaceutically acceptable vehicle" encompasses any substance that enables the formulation of the recombinant lentiviral vector according to the invention within a composition. A vehicle is any substance or combination of substances physiologically acceptable i.e., appropriate for its use in a composition in contact with a host, especially a human, and thus non-toxic. Examples of such vehicles are phosphate buffered saline solutions, distilled water, emulsions such as oil/water emulsions, various types of wetting agents sterile solutions and the like. Such vehicles also include cryoprotective compounds such as trehalose when the immunogenic composition is in freeze-dried form.

As defined herein, an "adjuvant" includes, for example, liposomes, oily phases, such as Freund type adjuvants, generally used in the form of an emulsion with an aqueous phase or can comprise water-insoluble inorganic salts, such as aluminium hydroxide, zinc sulphate, colloidal iron hydroxide, calcium phosphate or calcium chloride.

The present invention also relates to a method to produce recombinant lentiviral vector particles suitable for the preparation of a JEV vaccine, comprising or consisting of:

a) transfecting the recombinant lentiviral transfer vector carrying the lentiviral vector genome according to the invention, in a host cell, for example a HEK-293T cell line;

b) co-transfecting the cell of step a) with a plasmid vector encoding the envelope protein VSG, in particular the VSV-G of Indiana or of New Jersey VSV strains and with a plasmid vector encoding the lentiviral GAG and POL or mutated POL protein as packaging construct;

c) recovering the recombinant lentiviral particles expressing JEV antigens.

The present invention also relates to the use of the recombinant lentiviral vector genome according to the invention or recombinant lentiviral vector particles according to the invention as active ingredient for the in vitro production of an immunogenic composition or a vaccine composition.

Other features and advantages of the invention will be apparent from the examples which follow and will also be illustrated in the figures.

A. Production of an inducible JEV replicon cell line. A previously described JEV-RP9 (g3) replicon that expresses a *Renilla* luciferase reporter in place of the JEV structural proteins (Chien H-L, et al. 2011. *J Virol* 85:4698-4706) was modified so that expression of the replicon RNA could be induced with Tet-Express™. HEK293T cells were stably transformed with this JEV replicon. The *Renilla* luciferase signal, which serves as a marker for the steady-state accumulation of replicon RNA, was measured at 4, 24, 48, and 72 h post-induction of the stable JEV replicon cells. The inventors observed a progressive increase in signal from 24 through 72 h, corresponding to replication of the input RNA. A representative experiment out of n>3 repeats is shown.

B. Production of JEV RVPs. In order to produce RVPs, the JEV replicon cell line was transfected with a JEV plasmid encoding the JEV structural genes under the control of a Tet-Express™ inducible promoter. The expression of the JEV replicon and structural genes was induced and supernatants containing the RVPs were collected at 24, 48 and 72 h post-induction. The supernatants from cells that had not been transfected with the JEV structural genes served as a control. The successful production of RVPs was detected using an infectivity assay, where BHK21 cells were infected with 200 μl of supernatants and analyzed for *Renilla* expression at 24 h post-infection. The peak in RVP production was obtained at 48 h post-induction. A representative experiment out of n >3 repeats is shown. RLU, *Renilla* light units.

C. and D. Production and characterization of JEV g3 and g5 RVPs. The JEV replicon cells were transfected with plasmids expressing either JEV g3 or JEV g5 structural genes. The synthesis and production of RVPs was analyzed at 48 h post-induction. A representative experiment out of n >3 repeats is shown. C. The cell lysates were analyzed by Western blotting for JEV E and calnexin (CNX) as a loading control. The accumulation of intracellular JEV g5 E was lower than observed for the JEV g3 protein. The RVPs released in the supernatants were purified and analyzed by Western blotting using JEV E antibody (extracellular). The production of JEV g5 RVP was significantly lower compared to JEV g3 RVP production. D. The content of RVPs in the culture supernatants was also analyzed by quantification of the replicon RNA. As observed for the accumulation of viral proteins, there was much less replicon RNA in the JEV g5 RVP supernatants than in the JEV g3 RVP supernatants. The replicon RNA levels quantification was plotted along with the values obtained from the corresponding infectivity assay (as described in B.). Despite the reduced yield of JEV g5 RVPs, the particles produced appeared as competent for entry into new cells as the JEV g3 RVPs.

Figure 7:
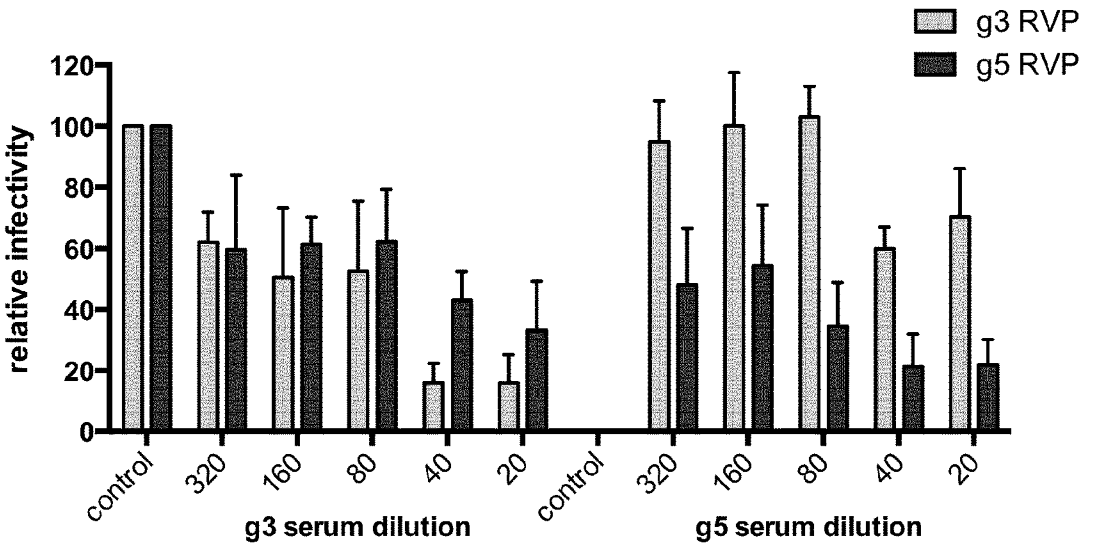

FIG. 7. JEV g3 or g5 RVPs were incubated with serial dilutions of sera collected at 20 days from mice inoculated with 1000 ffu of either JEV g3 (left) or JEV g5 (right). Sera collected from three individual mice were used in each experiment and sera collected from DPBS injected mice served as a control. After incubation, the RVPs were used to infect BHK21 cells. Intracellular *Renilla* luciferase activity was quantified at 24 h post-infection as a measure of successful RVP entry. Infectivity was measured as a function of the *Renilla* luciferase activity obtained with the control sera. Sera collected from JEV inoculated mice potently inhibited RVP entry.

Figure 8:
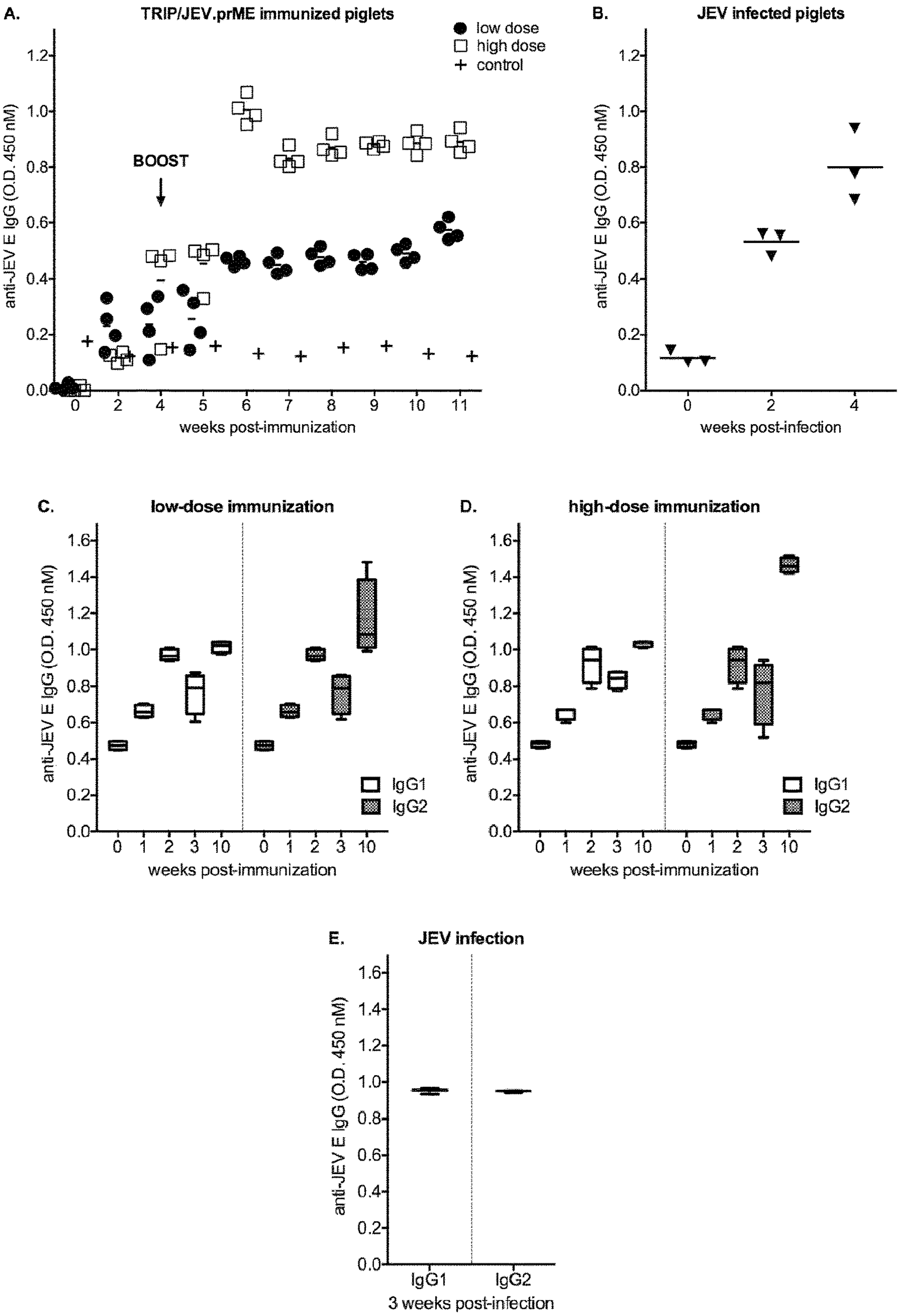

FIG. 8. Anti-JEV IgG responses of piglets immunized with TRIP/JEV.prME. In (A), two groups of four piglets were immunized intramuscularly with 6 (low dose) or 7 $\log_{10}$ TU (high dose) of TRIP/JEV.prME. As a control, two animals were inoculated with either low or high dose of TRIP/GFP. Animals were boosted 4 weeks after primary immunization with the same initial dose (vertical arrow). Serum samples were collected weekly and tested at a dilution of 1:400 for the presence of anti-JEV E IgGs by indirect ELISA. In (B), a group of three animals were experimentally infected with JEV strain Nakayama. The immune sera were tested at a dilution of 1:400 for the presence of anti-JEV E IgGs by indirect ELISA. In (C, D), box plots of the anti-JEV E IgG1/IgG2 from 1 to 10 weeks after immunization with the low (C) or high (D) dose of TRIP/JEV.prME are depicted. The vertical arrow indicates the boost. In (E), the levels of anti-JEV E IgG1/IgG2 in immune sera from piglets infected with JEV strain Nakayama.

Figure 9:
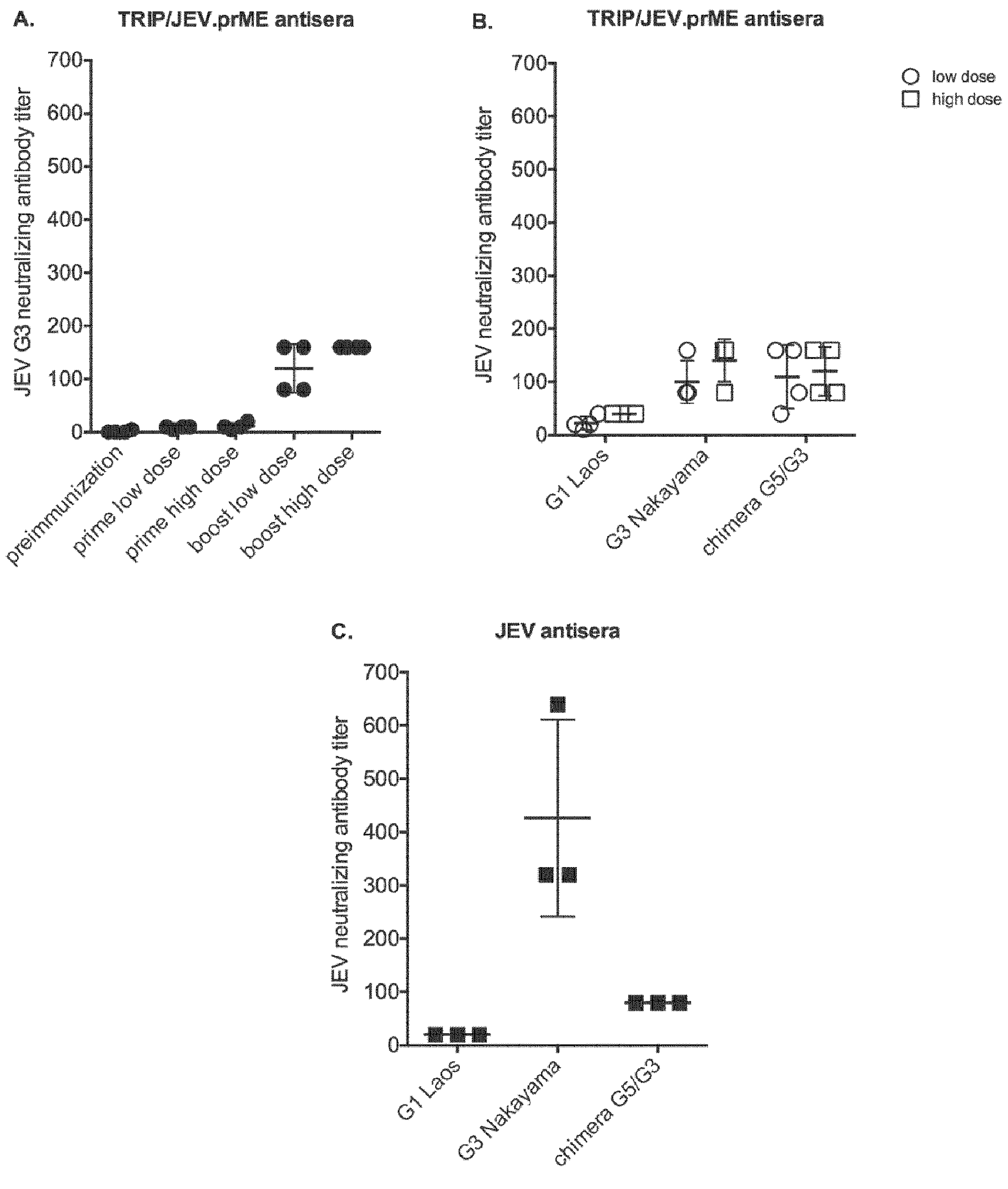

FIG. 9. Neutralizing antibody response in piglets immunized with TRIP/JEV.prME. Sera from piglets immunized with a low or high dose of TRIP/JEV. prME were tested for neutralization ability against JEV by PRNT50. In (A), the piglet sera collected prior immunization, 3 weeks after priming or 6 weeks after the boost were tested against the JEV G3 strain RP-9. In (B), the TRIP/JEV.prME antisera collected after the boost were tested for their cross-neutralizing capacity against JEV G1 and G3 strains, and JEV chimera G5/G3. In (C) the neutralizing activity of anti-JEV antibodies from animals experimentally infected with JEV G3 strain Nakayama was tested against JEV G1, G3, and the JEV chimera G5/G3 by PRNT50.

EXAMPLES

Materials and Methods

Cells and Antibodies

Mosquito *Aedes albopictus* C6/36 cells were maintained at 28° C. in Leibovitz medium (L15) supplemented with 10% heat-inactivated fetal bovine serum (FBS). African green monkey kidney-derived Vero cells were maintained at 37° C. in Dulbecco's modified Eagle medium (DMEM) supplemented with 5% FBS. Human neuroblastoma-derived SK-N-SH, and human kidney-derived HEK-293T cells were maintained in DMEM supplemented with 10% FBS.

Highly purified anti-pan*flavivirus* E monoclonal antibody (mAb) 4G2 was produced by RD Biotech (Besancon, France). Mouse mAb anti-JEV NS5 has been previously described (Katoh et al. 2011). Antibodies against Calnexin and SNAP-Tag® were purchased from Enzo Life Sciences and New England Biolabs, respectively. Horseradish peroxidase (HRP)-conjugated goat anti-mouse IgG and anti-rabbit IgG antibodies were obtained from Bio-Rad Laboratories. HRP-conjugated goat anti-pig antibody was obtained from Bethyl Laboratories. Alexa Fluor 488®-conjugated goat anti-mouse IgG antibody was obtained from Jackson ImmunoResearch.

Generation of Live Chimeric JEV

The molecular clone of JEV G3 strain RP-9 (Chen et al., 1996; Lin et al., 1996) used in the present study, pBR322 (CMV)-JEV-RP-9, has been previously described (Liang et al. 2009). The JEV G3 strain Nakayama was obtained from the National Collection of Pathogenic Viruses (NCPV, Salisbury, UK) and passaged twice on Vero cells. The construction of plasmids for generation of chimeric live JEV will be described in detail elsewhere. Briefly, a silent mutation that created a unique restriction site (Afl II) at position 2208-2213 (residues 705 and 706 of the viral polyprotein) was introduced directly in pBR322(CMV)-JEV-RP-9 through PCR mutagenesis. The resulting pBR322(CMV)-JEV-RP-9 (Afl II) plasmid was used as template to generate chimeric JEV. The fragment corresponding to nucleotides from 114 to 2213 and flanked by the unique sites Apa I and Afl II was substituted either with the fragment of JEV G1 strain CNS769_Laos_2009 (Genbank access number KC196115) corresponding to region 115-2214 excised from a JEV cDNA (Aubry et al. 2013) or JEV G5 strain XZ0934 (Genbank access number JF915894) (Li et al. 2011) corresponding to the region 114-2213 obtained from a synthetic gene (Genecust). The resulting plasmids had the backbone of JEV G3 in which the structural region has been replaced by the counterpart derived from JEV G1 or G5. To produce live JEV, the recombinant molecular clones pBR322(CMV)-JEV-G1/3 and pBR322(CMV)-JEV-G5/3 were transfected into HEK-293T cells using Lipofectamine 2000 (Life Technologies). At three days post-transfection, viral supernatants were collected and used to infect C6/36 cells in order to grow final stocks of chimeric JEV G1/3 and JEV G5/3. Their sequences were verified by extraction of viral RNA, followed by reverse transcription-PCR and sequencing.

Generation of Recombinant Lentiviral Vectors

For the construction of recombinant lentiviral vectors expressing JEV proteins, modifications that optimize the expression of prM and E genes in mammalian cells were done on the original sequence of JEV strain RP-9 of G3 using a synthetic gene (Genecust). The mammalian codon-optimized sequence coding for prM signal peptide followed by prM and E glycoproteins was cloned into the BamH1 and Xho1 restriction sites of the pTRIPΔU3CMV plasmid, to generate pTRIPΔU3CMV/JEVprME. The optimized sequence was further modified by mutagenesis PCR to generate TRIPΔU3CMV/JEVprME$^{\Delta TM}$ which contains the genes encoding prM and E lacking its two transmembrane domains (E$^{\Delta TM}$).

Lentiviral particles were produced by transient calcium co-transfection of 293T cells as described previously (Zennou et al., 2000), but with the following modifications: 24 h hours post-transfection, cell culture medium was replaced by serum-free DMEM (Dulbecco). Supernatants were collected 48 hours post-transfection, clarified by several rounds of low-speed centrifugation, and stoked at −20° C. The recombinant lentiviral vectors were pseudotyped with VSV-G envelope protein of serotype Indiana (IND) or New Jersey (NJ) (Beignon et al., 2009). In the resulting vectors TRIP/JEV.prME and TRIP/JEV.prME$^{\Delta TM}$ the CMV immediate early promoter (CMVie) drives the constitutive expression of recombinant JEV proteins. The TRIP/JEV vector stocks were titrated by real-time PCR on cell lysates from transduced 293T cells and expressed as transduction unit (TU)/ml (Iglesias et al., 2006). Titers of non-concentrated TRIP/JEV.prM vector bearing IND or NJ VSV.G envelope protein were 6.69 $10^6$ TU/ml and 1.78 $10^6$ TU/ml respectively. Titers of TRIP/JEV.prME$^{\Delta TM}$ vector bearing IND or NJ VSV.G envelope protein were 1.26 $10^7$ TU/ml and 1.76 $10^6$ TU/ml respectively. Vaccine stocks were adjusted by dilution in PBS and were inoculated in mice or pigs without further concentration.

Focus Immuno Assay for Measuring Virus Titers

Vero cells were seeded in 24-well plates. Tenfold dilutions of virus samples were prepared in duplicate in DMEM, and 200 μl of each dilution was added to the cells. The plates were incubated for 1 h at 37° C. Unadsorbed virus was removed, after which 1 ml of DMEM supplemented with 1.6% carboxymethyl cellulose (CMC), 10 mM HEPES buffer, 72 mM sodium bicarbonate, and 2% FBS was added to each well, followed by incubation at 37° C. for 2 days. The CMC overlay was aspirated, and the cells were washed with PBS and fixed with 4% paraformaldehyde for 15 min, followed by permeabilization with 0.1% Triton-X100 for 5 min. After fixation, the cells were washed with PBS and incubated for 1 h at room temperature with anti-E mAb 4G2, followed by incubation with HRP-conjugated anti-mouse IgG antibody. The plates were developed with the Vector® VIP peroxidase substrate kit (Vector Laboratories) according to the manufacturer's instructions.

Production of JEV Antigens

Large flasks of Vero cell monolayers were inoculated with JEV at low multiplicity of infection or mock-infected. The supernatant fluids of cells infected with JEV (JEV antigen) or mock-infected (normal cell antigen or NCA) were harvested and clarified.

The supernatants were precipitated with 7% w/v PEG 6,000 (Fluka), centrifuged, and the viral pellet was suspended in cold PBS supplemented with 0.1% β-propiolactone in 0.1 M Sorensen buffer (pH 9.0) for JEV inactivation. The working dilution of inactivated JEV antigen (1:200) was estimated based on «in-house» indirect ELISA using well-characterized human positive JEV serum samples and already validated JEV antigen.

For the purification of recombinant JEV VLPs, supernatants from TRIP/JEV-transduced cells were clarified by centrifugation at 3,000 g for 5 min at 4° C., loaded over a sucrose cushion (15% sucrose in 10 mM Tris-HCl [pH 7.5], 2.5 mM EDTA, 50 mM NaCl), and then centrifuged at 100,000 g for 2.5 h at 4° C. After centrifugation, the pellet was suspended in 50 μl of cold THE buffer and analyzed by immunoblot assay.

The DES® expression system (Life Technologies) was required for the production of recombinant viral antigens in *Drosophila* S2 cells. A synthetic gene coding for prM followed by E$^{\Delta TM}$ from JEV strain SA-14 of G3 (Genbank access number M55506) was cloned into the shuttle plasmid vector pMT/BiP/SNAP, a derived pMT/BiP/V5-His vector (Life Technologies) in which the SNAP-tag sequence (Covalys BioSciences AG) had been inserted in frame with the insect BiP signal peptide (unpublished data). The resulting plasmid pMT/BiP/JEV.prME$^{\Delta TM}$-SNAP encodes prM followed by E$^{\Delta TM}$ in fusion with the N-terminus of SNAP-Tag®. The synthetic genes coding for the E protein domain III (EDIII) of JEV strain JaNAr0102/Japan/2002/Mosquito of G1 (Genbank access number AY377577), JEV strain GP05 of G3 (Genbank access number FJ979830), and JEV strain 10-1827 of G5 (Genbank access number JN587258) were fused in frame to the C-terminus of SNAP-tag into the plasmid pMT/BiP/SNAP. The resulting plasmids pMT/BiP/JEV.prME$^{\Delta TM}$-SNAP and pMT/BiP/SNAP-JEV.EDIII were transfected into S2 cells to establish stable cell lines S2/JEV.prME$^{\Delta TM}$-SNAP and S2/SNAP-JEV.EDIII for G1, G3, and G5 according to the manufacturer's recommendations (Life Technologies). After 10 days cadmium induction of S2/JEV.prME$^{\Delta TM}$-SNAP and S2/SNAP-JEV.EDIII cell lines, secreted soluble His-tagged chimeric proteins were purified on chelating column chromatography and then Superdex column. The protein estimation of purified chimeric proteins E$^{\Delta TM}$-SNAP protein and SNAP-JEV.EDIII proteins was determined using a BCA protein assay kit (Thermo Scientific). Recombinant SNAP protein served as a negative antigen control.

Immunodetection of Viral Proteins

For immunoblot assay, protein samples were applied to a NuPAGE® Bis-Tris 4-12% gel (Life Technologies) and followed by electroblotting onto a PDVF membrane. Proteins were probed with appropriate dilution of the primary monoclonal antibody or mouse polyclonal immune serum. After washes in PBS-Tween, the membrane was incubated with HRP-conjugated secondary antibodies. The reactions were detected using Pierce™ ECL Western Blotting Substrate (Thermo Scientific).

For immunofluorescence assay, cells were fixed with 3.2% paraformaldehyde in PBS and permeabilized with 0.1% Triton X-100 in PBS. JEV E protein was detected with the mAb 4G2, followed by incubation with AlexaFluor488-conjugated secondary antibody. The cover slips were mounted with ProLong® Gold Antifade Reagent with DAPI (Life Technologies). The slides were examined using a fluorescent microscope (Axioplan 2 Imaging, Zeiss).

Immunization and Challenge of Mice

Six-week-old female Balb/c mice were housed under pathogen-free conditions at the Institut Pasteur animal facility. The protocols and subsequent experiments were ethically approved by the Ethic Committee for Control of Experiments on Animals (CETEA) at the Institut Pasteur and declared to the Ministère de l'Enseignement Supérieur et de la Recherche (n° 000762.1) in accordance with regulations in France.

Experiments were conducted following the guidelines of the Office Laboratory of Animal Care at the Institut Pasteur. Groups of mice were intraperitoneally (i.p.) inoculated with recombinant lentiviral vectors in 0.1 ml DPBS supplemented with 0.2% endotoxin-free serum albumin. Immunized mice were bled by puncturing at the retro-orbital sinus level. A very low individual variability exists within each group of mice inoculated with recombinant lentiviral vectors justifying the use of pooled sera in subsequent experiments (Iglesias et al., 2006). For passive seroprotection experiments, pooled immune sera were transferred i.p. into 3-week-old C57/Bl6 mice one day before challenge with JEV strain RP-9 by i.p. route. The challenged mice were monitored for signs of morbidity and mortality. Euthanasia was applied on animals showing the symptoms of viral encephalitis.

Immunization and Challenge of Piglets, as Described in De Wispelaere Et al., *PLOS Negl. Trop. Dis.* 2015

Pig experiments were conducted following the guidelines of Swiss Animal Welfare Regulations (Veterinary Service of LANAT).

Groups of 7-week-old specific pathogen free Swiss Land Race piglets from in-house breeding were housed in groups, and an adaptation time to the new environment of one week was given before starting the experiment.

For immunization, the TRIP/JEV.prME lentiviral vector was diluted to a final volume of 0.5 ml with PBS (Life Technologies). Immunization with the TRIP/GFP lentiviral vector was used as a negative control (Iglesias et al., 2006). From a group of 5 piglets, four were vaccinated intramuscularly with various doses of the TRIP/JEV.prME vector and one was injected with the equivalent dose of control lentiviral vector TRIP/GFP. Immunized animals were bled before the first vaccination and then weekly until the end of the experiment. Four weeks after the first vaccination, all animals got a booster vaccination with the same dose of recombinant lentiviral vectors as at the first time point. For ethical reasons no lethal challenge was performed as protection in pigs. As a control, 3 animals were inoculated by the oronasal route with 7 $\log_{10}$ TCID50 of live JEV Nakayama G3. All pigs developed temporary fever and viremia and recovered completely after 4-6 days. The animal sera were examined weekly for anti-JEV antibody.

Detection of Antibodies by Indirect ELISA and Neutralization Test

Indirect ELISA measured the production of anti-JEV IgGs in immunized mice and piglets. The 96-well ELISA plates (Nunc) were coated with 0.1 ml of inactivated native JEV antigen or highly purified recombinant JEV antigens diluted in PBS at the concentration of 1 μg·mL-1 at 4° C. overnight. NCA and SNAP served as negative control antigens. After washing, plates were incubated with two-fold serial dilutions of pooled serum samples starting at a 1:100 dilution, and then incubated with a 1:10,000 dilution of HRP-conjugated anti-mouse IgG antibody. After addition of the TMB substrate, absorbance was measured at 450 nm. The Immune Status Ratio (ISR) of each group of immunized mice or piglets is obtained by dividing the average of JEV antigen $OD_{450}$ values by the average control antigen $OD_{450}$ values. The end-point titers of anti-JEV antibodies in mouse sera were calculated as the reciprocal of the last dilution of serum having ISR value >3.0. Pig sera were tested as described for the mice, using HRP-conjugated goat anti-pig antibody as a secondary antibody. Pig sera obtained prior immunization were used as a negative control. Indirect ELISA was performed as described in de Wispelaere et al, *J. Virol.* 2015.

Neutralizing ability of mouse and pig serum antibodies against JEV was determined by focus reduction neutralization tests (FRNT) or plaque (PRNT) reduction neutralization tests on Vero cells, respectively. Mouse serum samples from each group were pooled. Pig sera were tested individually in triplicates starting at a 1:5 serum dilution. Pooled mouse or individual pig serum samples were two-fold serial diluted in DMEM supplemented with 2% FBS, with a starting dilution of 1:10, and incubated for 2 h at 37° C. with an equal volume of viral suspension containing 100 FFU of JEV. Remaining infectivity was assayed on Vero cell monolayers by FFA (see above). The end-point titer was calculated as the reciprocal of the highest serum dilution tested that reduced the number of FFU by 50% (FRNT50) or PFU ($PRNT_{50}$) by 50%.

Statistical Analysis

Statistical comparisons among groups were analyzed with one way ANOVA using GraphPad Prism version 6.0a for MacOSX (GraphPad Software Inc, La Jolla California USA). A P value less than 0.05 was considered statistically significant.

A Log-rank (Mantel-Cox) test was used to compare survival data. Antibody levels between groups of immunized pigs were compared by Mann Whitney U test and the level of significance was set at 5%. GraphPad Prism® (GrapPad Software Inc. La Jolla, CA, USA) was used for all statistical analysis.

JEV Replicon Cell Line

The JEV-RP9 replicon plasmid, J-R2A (Chien H-L, et al. 2011. *J Virol* 85:4698-4706) was modified so that the hepatitis delta virus ribozyme was placed immediately adjacent to JEV-RP9 3'-end, and was followed by a simian virus 40 (SV40) poly(A) sequence. To do so, the corresponding sequence in the pBR322(CMV)-JEV-RP9 plasmid was excised through digestion with NsiI and ClaI, and cloned into the similarly treated J-R2A. Next, the plasmid was modified to replace the SP6 promoter with an inducible $P_{TRE3G}$ promoter (Clontech). The $P_{TRE3G}$ promoter was amplified from the pTRE3G vector (Clontech, catalog no. 631173) using the primers

```
5'-ctcgagtttactccctatcagtga-3'
(SEQ ID NO: 36, XhoI site underlined)
and

5'-tcacacagataaacttctcggttcactaaacgagct-3'
(SEQ ID NO: 37,
JEV-RP9 nucleotides 1 to 18 underlined).
```

Nucleotides 1 to 249 of the JEV-RP9 genome were amplified using the primers

```
5'-agctcgtttagtgaaccgagaagtttatctgtgtga-3'
(SEQ ID NO: 38, P_TRE3G promoter nucleotides
291 to 308 underlined)
and

5'-tgataagagccagcacgaatcg-3' (SEQ ID NO: 39).
```

The primers were designed so that both fragments shared a sequence homology of 36 nucleotides. A second round of PCR using these first two fragments allowed the amplification of a fragment composed of the $P_{TRE3G}$ promoter fused to the nucleotides 1 to 249 of JEV-RP9. This fragment was digested with XhoI and ApaI and cloned into the J-R2A plasmid treated with SalI and ApaI. The resulting pTRE3G-JEV-RP9.replicon plasmid was amplified in Stbl2 cells (Life Technologies, catalog no. 10268-019). HEK293T cells were cotransfected with the pTRE3G-JEV-RP9.replicon and the pTK-Hyg selection vector (Clontech, catalog no. 631750) and stable cells were selected with 50 μg/ml of hygromycin.

The expression of the JEV replicon was induced using the Tet-Express™ system (Clontech, catalog no. 631177) according to the manufacturer's instructions. At 1 h post-induction, the medium containing the inducer was removed and DMEM supplemented with 2% FBS was added to the cells. At the indicated times post-induction, the cells were collected, and the samples were processed according to the instructions in the *Renilla* luciferase assay system (Promega, catalog no. E2820). The luciferase signal was read using a Centro XS3 LB960 (Berthold Technologies) plate reader.

Reporter Viral Particles (RVP)

The fragment encompassing the structural genes of JEV-RP9 was amplified using the primers

```
5'-gaagatctatgactaaaaaaccaggagggcccggt-3'
(SEQ ID NO: 40, BgIII site underlined)
and

5'-ttctgcagtcaagcatgcacattggtcgctaaga-3'
(SEQ ID NO: 41, PstI site underlined).
```

The fragment was digested with BglII and PstI and cloned into the similarly treated pTRE3G vector (Clontech, catalog no. 631173). The resulting pTRE3G-JEV-RP9.CprME plasmid was amplified in Stbl2 cells (Life Technologies, catalog no. 10268-019). The pTRE3G-JEV-XZ0934.CprME plasmid containing JEV-XZ0934 structural genes was designed similarly to the pTRE3G-JEV-RP9.CprME plasmid and was synthesized by GeneGust. To produce JEV g3 or JEV g5 RVPs, HEK293T-JEV-RP9.replicon cells were plated in a 10-cm dish and then transfected respectively with pTRE3G-JEV-RP9.CprME or pTRE3G-JEV-XZ0934.CprME using Lipofectamine 2000 (Life Technologies, catalog no. 11668-019) according to the manufacturer's instructions. The expression of the JEV replicon and structural genes was induced using the Tet-Express™ system (Clontech, catalog no. 631177) according to the manufacturer's instructions. The supernatants containing RVPs were collected at 48 h post-induction and clarified by centrifugation for 5 min at 1,000 g, and aliquots were stored at −80° C.

For RVP purification, the clarified supernatant was loaded over a sucrose cushion (15% sucrose in TNE (10 mM Tris-HCl [pH 7.5], 2.5 mM EDTA, 50 mM NaCl)), and centrifuged at 100,000 g for 2.5 h at 4° C. The supernatants were discarded, and the purified RVPs were suspended in TNE buffer.

For the infectivity assays, BHK21 cells were seeded in 24-well or 96-well tissue culture plates in DMEM supplemented with 2% FBS. Then, purified RVPs or portions of supernatants containing RVPs were added to the cells, and the plates were incubated for 1 h at 37° C. Unadsorbed RVPs were removed, after which DMEM supplemented with 2% FBS was added to the cells, followed by incubation at 37° C. At 24 h post-infection, the samples were processed according to the instructions in the *Renilla* luciferase assay system (24-well format, Promega, catalog no. E2820) or the *Renilla*-Glo® Luciferase Assay System (96-well format, Promega, catalog no. E2720). The *Renilla* luciferase signal was read using a Centro XS3 LB960 (Berthold Technologies) plate reader.

Results

Generation of TRIP/JEV Vectors

Figure 1:
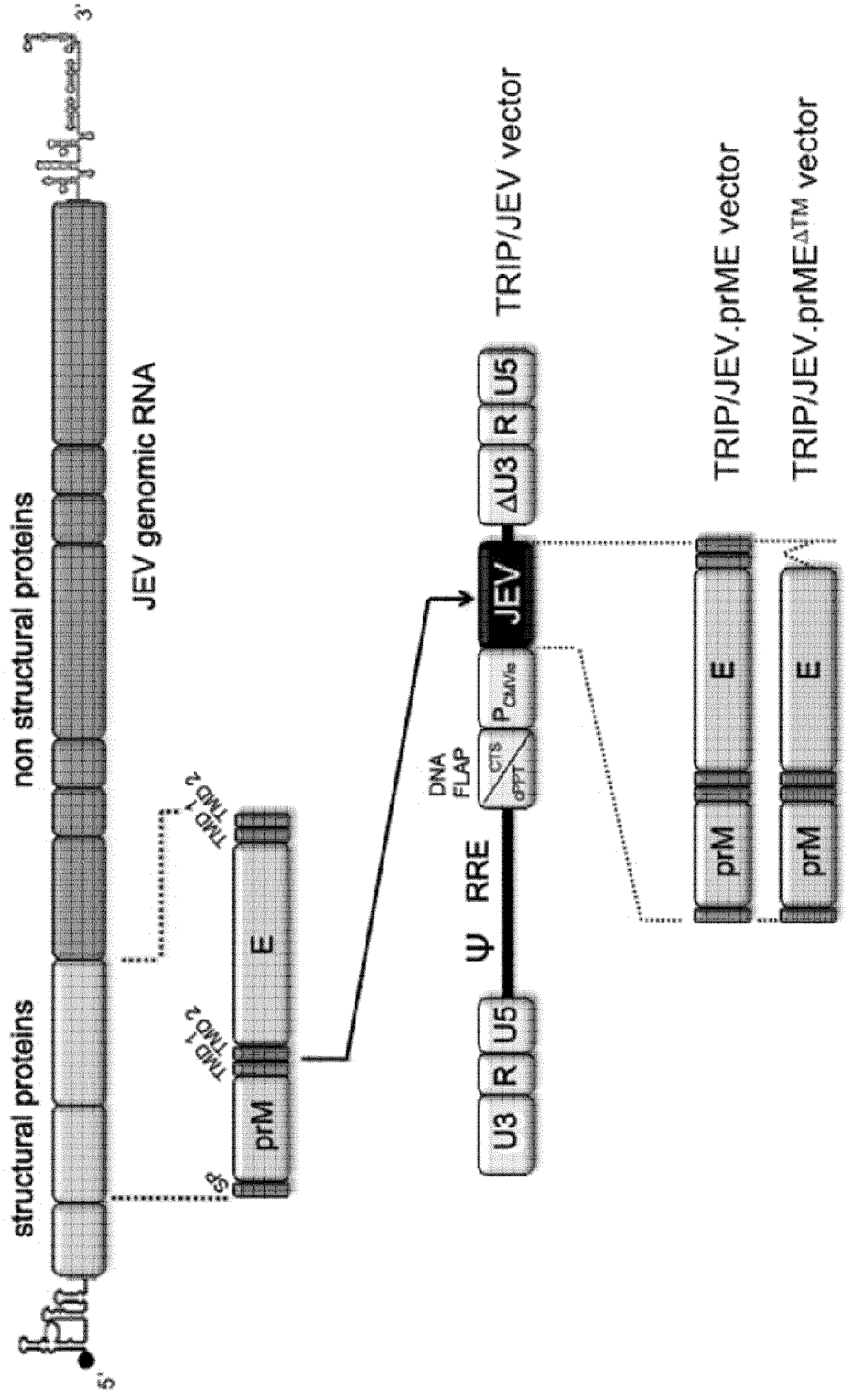
FIG. 1. Construction strategy of TRIP/JEV vectors. Schematic representation of the two strategies to construct TRIP/JEV vectors. In top, the schematic representation of genomic RNA organization from JEV with the prM and E genes. The codon-optimized sequence encoding prM and E from JEV strain RP-9 of G3 was cloned into the TRIP lentiviral vector under the control of human cytomegalovirus immediate early promoter (CMVie). TRIP/JEV.prME vector includes the signal peptide sequence for prM (SP) followed by the entire prM and E gene regions of JEV strain RP-9 of G3. TRIP/prME$^{\Delta TM}$ vector includes the same JEV sequence except that E was deleted from its two transmembrane domains TMD1 and TMD2.

The inventors have reported earlier that a single immunization with a non-replicative lentiviral vector expressing the soluble form of West Nile E glycoprotein induced a robust protective humoral response in a mouse model of WNV encephalitis (Iglesias et al., 2006, Coutant et al., 2008). To assess the potential of lentiviral vectors expressing envelope proteins from JEV at eliciting humoral response capable of protecting against JEV infection, codon-optimized gene encoding JEV prM and E of G3 was inserted into the lentivirus TRIP vector (FIG. 1). The inventors generated TRIP/JEV.prME and TRIP/JEV.prME$^{\Delta TM}$ lentiviral vectors, expressing the prM signal peptide followed by the membrane protein prM and the envelope glycoprotein E (prME) either native or lacking its two C-terminal transmembrane domains (prME$^{\Delta TM}$). In these constructs, prM contributes to the folding, stability, and efficient secretion of the glycoprotein E.

Lentiviral vectors which expressed JEV proteins were pseudotyped with VSV-G protein of the Indiana serotype. Non-replicative TRIP/JEV.prME and TRIP/JEV.prME$^{\Delta TM}$ particles were produced on HEK-293T cells, achieving titers of 6.8 and 7.1 $log_{10}$ TU per ml, respectively.

Figure 2:
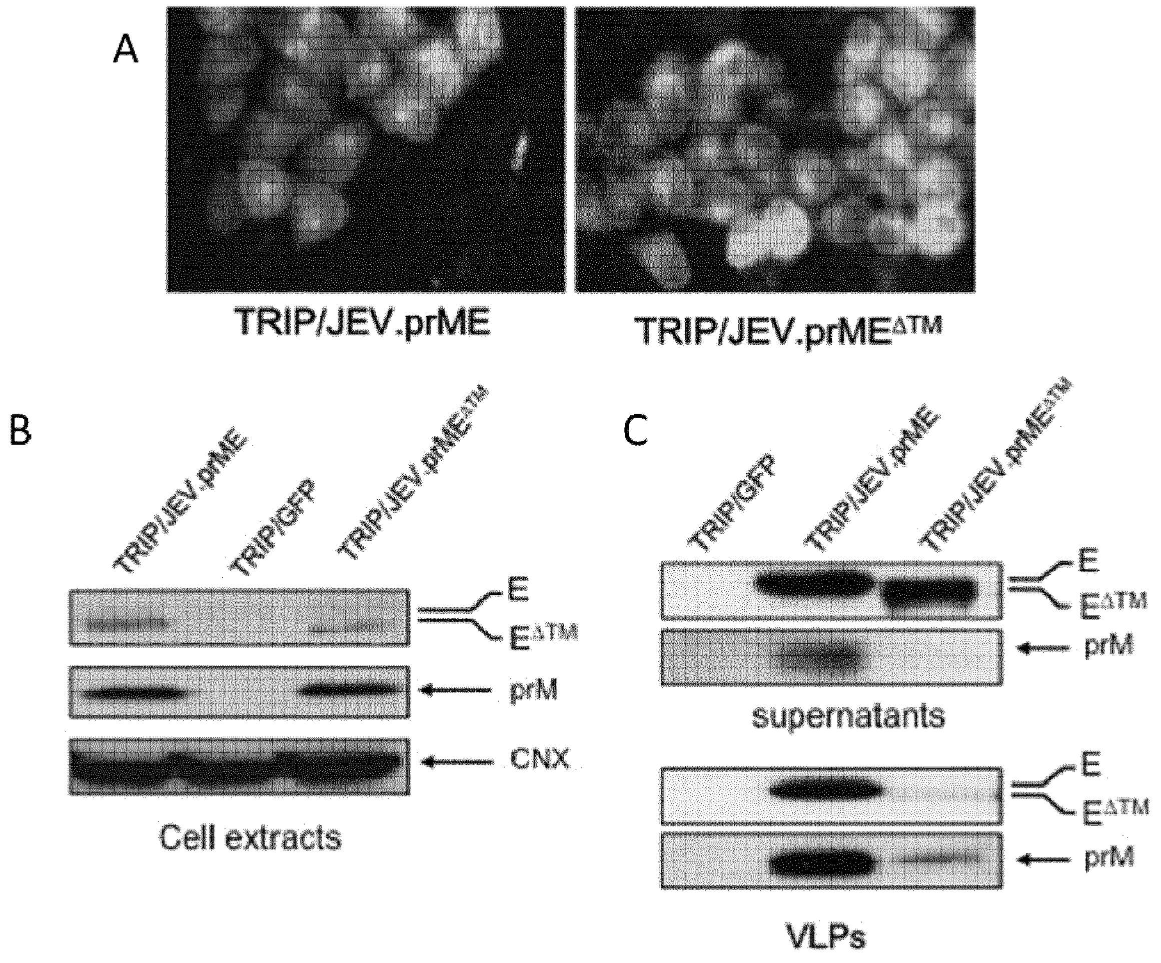
FIG. 2. Expression of recombinant prM and E from JEV by TRIP/JEV vectors. Detection of recombinant JEV prM and E proteins in TRIP/JEV-transduced 293T cells. (A) Immunofluorescence analysis of transduced cells using anti-E mAb 4G2 as primary antibody. (B, C) immunoblot analysis of prM and E from radio immunoprecipitation assays (RIPA) cell lysates (B) or supernatants (C) of transduced cells with TRIP/JE or TRIP/GFP vector. In (B), the intracellular prM and E were detected with a mouse polyclonal serum directed against JEV strain RP-9 (JEV antisera). In (B), JEV E and prM from supernatants of transduced cells were detected with mAb 4G2 or with a mouse polyclonal serum directed against JEV strain RP-9 (JEV antisera), respectively. In (C), JEV VLPs were concentrated from supernatants of TRIP/JE vector-transduced cells and analysed by immunoblotting with anti-E mAb 4G2 and JEV antisera. TRIP/GFP served as a negative control. The bands corresponding to prM, E or EΔTM and calnexin (CNX) are indicated with arrows to the right of the blots.

The antigenicity of recombinant JEV proteins was assessed by transducing HEK-293T cells with TRIP/JEV.prME or TRIP/JEV.prME$^{\Delta TM}$ vector. TRIP/GFP vector served as a control. At 48 h post-transduction, the inventors analyzed E intracellular expression by immunofluorescence assay and observed a similar staining pattern in TRIP/JEV-transduced cells expressing prME or prME$^{\Delta TM}$ (FIG. 2A). Immunoblot assays using mouse anti-JEV antisera (FIG. 2B) detected intracellular recombinant prM and E in RIPA lysates from HEK-293T cells transduced with TRIP/JEV vectors. Both recombinant JEV proteins were found in the supernatants of HEK-293T cells transduced with TRIP/JEV vectors but only TRIP/JEV.prME vector was efficient in the secretion of prM suggesting that expression of the soluble form of E could impair the release of prM into the intracellular compartment (FIG. 2C, top). Because JEV prM and E have the capacity to self-assemble into VLPs, the inventors decided to assess whether VLPs were secreted from 293T cells transduced with TRIP/JEV vectors by ultracentrifugation of cell supernatants through a sucrose cushion. The pellet was analysed by immunoblot assay using anti-E mAb 4G2 and anti-JEV sera (FIG. 2C, bottom). Extracellular JEV VLPs containing prM and E accumulated in the supernatant of 293T cells transduced with TRIP/JEV.prME vector but not TRIP/JEV.prME$^{\Delta TM}$ vector.

Because TRIP/JEV.prME$^{\Delta TM}$ vector was poorly efficient in the release of prM and the formation of VLPs, it is likely that the deletion of the C-terminal region of E prevents the formation of stable prME complexes. Altogether, these results show that transduction of cells by TRIP/JEV.prME vector leads to efficient secretion of recombinant JEV VLPs.

Induction of JEV-Specific Antibodies by TRIP/JEV Vector Immunization in Mice

To evaluate humoral responses induced by the lentiviral TRIP/JEV vectors, adult BALB/c mice were inoculated with increasing doses of TRIP/JEV.prME or TRIP/JEV.prME$^{\Delta TM}$ (3 to 5 $log_{10}$ TU per animal) by i.p. route. At 21 days post-immunization, sera were collected from each group of mice. Pooled sera were tested for the presence of anti-JEV IgGs by indirect ELISA using inactivated JEV particles as coating viral antigens (Table 1). NCA served as a control antigen. There was little to no antibody responses against JEV at TRIP/JE vector doses lower than 5 log TU per animal. The dose of 5 $\log_{10}$ TU induced a significant production of anti-JEV specific antibodies with a mean titer reaching 1,600 for TRIP/JEV.prME and 400 for TRIP/JEV.prME$^{\Delta TM}$ (Table 1, upper panel). At the highest dose (6 log TU) inoculated in mice, the mean titer of TRIP/JEV.prME antibody reached 10,000. The latter dose was not further used due to the too large volume of non-concentrated TRIP/JE vector inoculated in mice by i.p. route. We therefore decided to select the unique dose of 5 $\log_{10}$ TU in subsequent mouse immunizations. To determine the time course of anti-JEV production, Balb/c mice that received 5 log TU of TRIP/JEV.prME or TRIP/JEV.prME$^{\Delta TM}$ were bled at 7, 14 and 21 days post-immunization (Table 1, lower panel). Anti-JEV antibodies were detectable at Day 14 of immunization and reached significant titers at Day 21.

TABLE 1

Anti-JEV antibody responses elicited by a single dose of TRIP/JEV vectors.

| | TRIP/JEV.prME | TRIP/JEV.prME$^{\Delta TM}$ |
|---|---|---|
| Vector dose[1] (TU) | | |
| $10^3$ | <100 | <100 |
| $10^4$ | 100 | 100 |
| $10^5$ | 1,600 | 400 |
| $10^6$ | 10,000 | n.d.[3] |
| Time post-immunisations[1,2] | | |
| Day 7 | <100 | <100 |
| Day 14 | 400 | 200 |
| Day 21 | 1,600 | 400 |

[1]Mice were inoculated with TRIP/JEV vectors by the intraperitoneal route. Anti-JEV antibody titer was determined by indirect ELISA using inactivated JEV G3 as viral antigen.
[2]Mice were inoculated with 105 TU and immune sera were collected at various days post-infection.
[3]n.d.: not done.

To enhance the production of anti-JEV specific antibodies, immunized mice received a booster dose of 5 $\log_{10}$ TU of recombinant TRIP/JEV vectors bearing the VSV-G envelope protein of a different VSV strain (New-Jersey), 4 weeks after the first inoculation. Immune sera were collected 3 weeks after the boosting inoculation and ELISA measurements showed a 40-fold increase in anti-JEV antibody titers. The production of anti-JEV IgGs reached the mean titers of 64,000 for TRIP/JEV.prME and 16,000 for TRIP/JEV.prME$^{\Delta TM}$.

Figure 3:
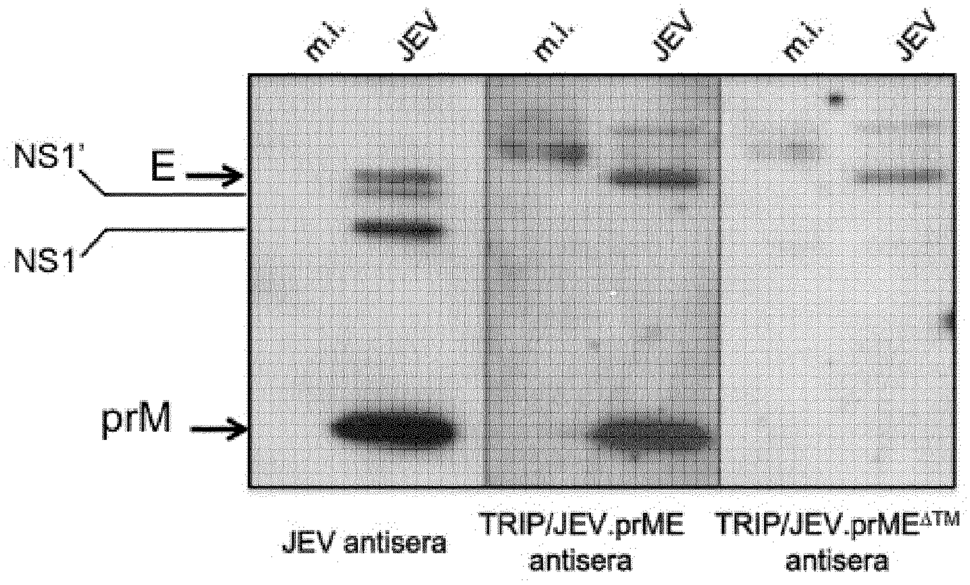
FIG. 3. Recognition of JEV prM and E by anti-TRIP/JEV antibodies. Cell lysates in RIPA buffer from Vero cells infected with JEV strain RP-9 (JEV) or mock-infected (mi.) were tested with pooled immune sera (antisera) from Balb/c mice twice inoculated with 5 $\log_{10}$ TU of TRIP/JEV.prME or TRIP/JEV.prME$^{\Delta TM}$ vector by immunoblot assay. TRIP/JEV antisera were collected 3 weeks after the boosting inoculation. Mouse polyclonal serum directed against JEV strain RP-9 (JEV antisera) served as a positive control. The bands corresponding to JEV E, NS1/NS1' and prM proteins are indicated with arrows to the left of the blot.

Mice that received TRIP/JEV.prME displayed specific antibodies against prM and E (FIG. 3). In contrast, sera from mice inoculated with TRIP/JEV.prME$^{\Delta TM}$ contained only anti-E antibody presumably due to the retention of prM in the intracellular compartment of transduced cells.

Balb/c mice that received two doses of TRIP/JEV.prME$^{\Delta TM}$ or TRIP/JEV.prME elicited anti-E antibody titers with a similar range of about 1,000 (Table 2). The inventors next assessed whether the immune sera were also reactive with the E proteins from different JEV genotypes. Because *flavivirus* EDIII is accessible on the virion surface and contains sub-type specific neutralizing epitopes, the inventors used the recombinant SNAP-tagged EDIII proteins of G1, G3, and G5 as viral antigens for indirect ELISA. Anti-JEV G3 antibodies recognize EDIII from G1 and at the lower level G5 (Table 2). Immunized mice that received either TRIP/JEV.prME or TRIP/JEV.prME$^{\Delta TM}$ elicited similar or even higher anti-EDIII antibody titers from 4,000 to 8,000 regardless of JEV genotypes tested. Thus, both TRIP/JE.prME and TRIP/JE.prME$^{\Delta TM}$ are capable of inducing a similar level of anti-EDIII antibodies that are broadly reactive with different genotypes of JEV. It is important to note that mouse JEV antisera directed against JEV G3 was less efficient to recognize EDIII from JEV of G1 and G5 than TRIP/JEV immune sera.

TABLE 2

Reactivity of TRIP/JEV antisera toward recombinant JEV antigens.

| Recombinant viral antigens[a] | JEV[b, c] | TRIP[b, d]/JEV.prME | TRIP[b, d]/JEV.prME$^{\Delta TM}$ |
|---|---|---|---|
| rE$^{\Delta TM}$ | 1,300 | 1,100 | 900 |
| rEDIII-G1 | 4,000 | 8,000 | 8,000 |
| rEDIII-G3 | 4,000 | 8,000 | 8,000 |
| rEDIII-G5 | 1,000 | 4,000 | 4,000 |

[a] Highly purified recombinant proteins produced in S2 cells served as viral antigens for indirect ELISA. rE$^{\Delta TM}$-soluble form of E from JEV of G3. rEDIII: domain III of E from JEV of different genotypes.
[b] Determined by indirect ELISA on pooled sera. The end-point titers of antibodies in mouse immune sera as the reciprocal of the last dilution of serum having ISR value >3.0.
[c] Antibody response of mice to inoculation of live JEV strain RP9 of G3.
[d] Antibody response of mice to inoculation of TRIP/JEV vector. Mice were inoculated i.p. twice with 5 log TU of TRIP/JEV vector at an interval of 1 month. Sera were collected 3 weeks after the boost.

In Vitro Cross-Protective Activity of JEV Antisera Elicited in Mice after TRIP/JEV Immunization A focus reduction neutralization test (FRNT) was performed to evaluate the ability of TRIP/JEV vectors to elicit a neutralizing antibody response against JEV of G3 (Table 3). Immune sera obtained from Balb/c mice that recovered from a lethal challenge with JEV strain RP-9 had a FRNT50 of 150. A weak titer of FRNT50 of 10 was observed in mice inoculated with a single dose of 5 $\log_{10}$ TU of TRIP/JEV vector. A booster dose one month after the prime elicited JEV-neutralizing antibodies titers from 40 (TRIP/JEV.prME$^{\Delta TM}$) to 80 (TRIP/JEV.prME) (Table 3).

Figure 4:
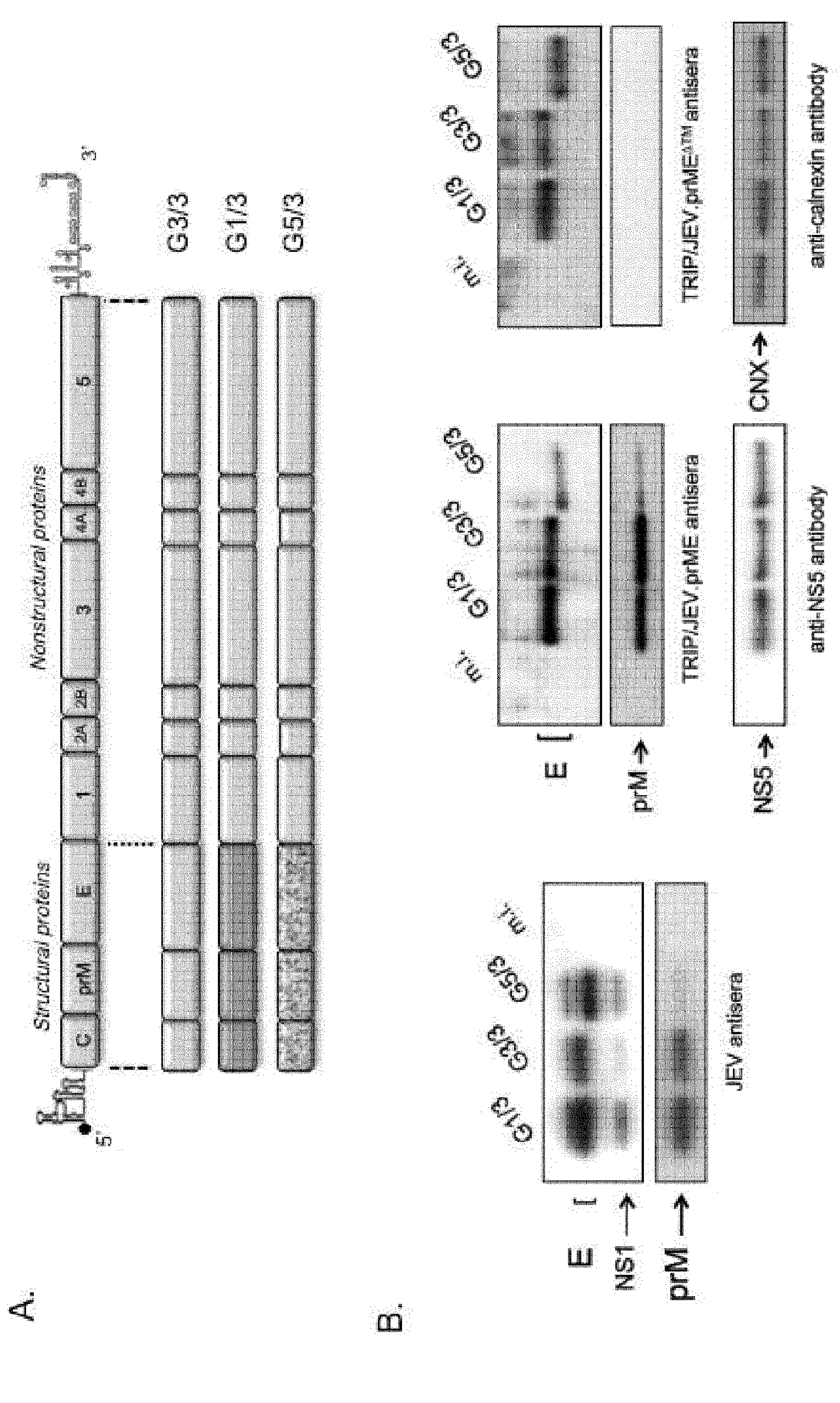
FIG. 4. Construction strategy of chimeric live JEV and their recognition by anti-TRIP/JEV sera. (A) schematic diagram of chimeric JEV in which the structural protein region from JEV of G3 (strain RP-9) was replaced by the counterpart from JEV of G1 (strain CNS_Laos_2009) or G5 (strain XZ0934). The resulting chimeric JEV G1/3 and G5/3 include the sequences encoding C, prM and E from JEV of G1 or G5 into the backbone of JEV of G3, respectively. The parental JEV was designed as JEV G3/3. (B, C) recognition of chimeric JEV proteins by JEV antisera (left) or TRIP/JEV antisera (right). Cell lysates in RIPA buffer from Vero cells infected with parental JEV of G3 (G3/3), chimeric JEV G1/3 and G5/3, or mock-infected (m.i.) were analysed by immunoblotting with the indicated antibodies. Anti-JEV.NS5 (NS5) and anti-calnexin (CNX) antibodies served to normalize protein expression level.
Figure 6:
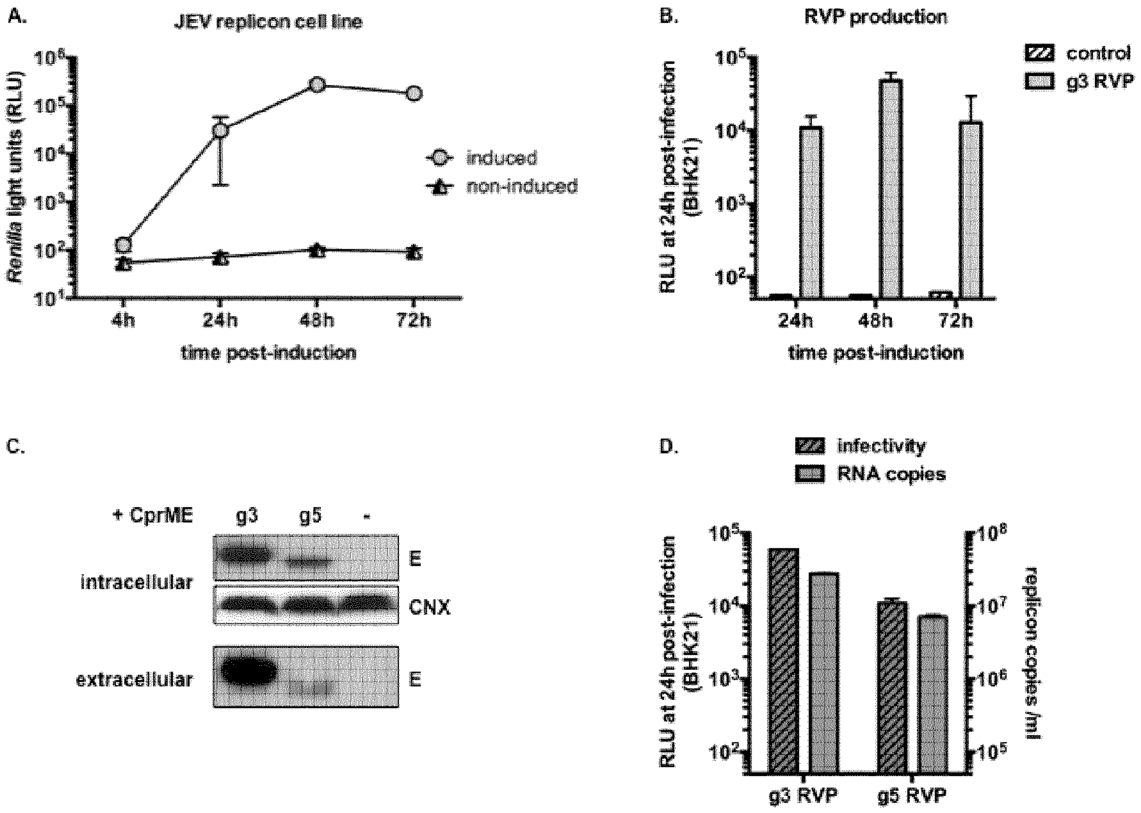
FIG. 6. Production and characterization of JEV reporter viral particles (RVPs).

Since the JEV antigens expressed by TRIP/JEV vectors were derived from a JEV G3, the inventors assessed their protective capacity against emerging JEV genotypes, namely G1 and G5. To investigate this issue, the inventors decided to substitute the region encoding C, prM and E into the infectious cDNA clone of JEV G3 by the counterpart from JEV G1 or G5 (FIG. 4A). Since immunizations with the TRIP/JEV vectors are solely directed against JEV structural proteins, the contribution of non-structural proteins of JEV G1 and G5 was not explored so far. The growth of chimeric JEV G1/3 or JEV G5/3 was comparable to that of JEV G3/3 in cultured cell lines (FIG. 6). Immunoblot analysis showed that immune sera from JEV G3/3-infected mice recognized both prM and E from JEV regardless of JEV genotype (FIG. 4B, left panel).

The inventors observed that E from chimeric JEV G5/3 migrated faster than those of other viruses and prM was weakly detected with JEV G3/3 antisera. Essentially similar results were obtained when the inventors performed this experiment with mouse immune sera generated by lentiviral vector vaccination. Sera from mice immunized with TRIP/JEV vectors recognized prM and E (TRIP/JEV.prME) or E alone (TRIP/TRIP/JEV.prME$^{\Delta TM}$) of all chimera JEV (FIG. 4B, right panel). As observed with JEV G3 antisera, immunization with TRIP/JEV.prME elicited specific anti-JEV antibodies that were poorly reactive with prM from chimeric JEV G5/3. As a control, anti-NS5 antibody showed a similar reactivity with NS5 from all chimeric JEV tested. Therefore, the low antigenic reactivity of TRIP/JEV.prME antisera toward prM from JEV of G5 was not the consequence of a lower viral growth in HEK-293T cells. In contrast to TRIP/JEV.prME, TRIP/JEV.prME$^{\Delta TM}$ was capable of inducing antibodies that can similarly recognize the E protein from chimeric JEV G1/3, G3/3 and G5/3. One explanation is that a soluble form of E exhibits a greater propensity to generate antibodies recognizing highly conserved epitopes that are potentially cryptic within the prME complexes or JEV VLPs.

FRNT assays were performed to evaluate the ability of TRIP/JEV vectors to elicit a neutralizing antibody response against JEV G1/3 or G5/3 (Table 3). Infection of Balb/c mice with JEV of G3 gave sera with a FRNT50 of 140 and 50 for chimeric JEV G1/3 and G5/3, respectively. Immunized mice that received TRIP/JEV vectors developed neutralizing antibody titers against chimeric JEV G1/3 and G5/3 (Table 3).

TABLE 3

Neutralizing activities anti-TRIP/JEV antibodies against JEV of different genotypes.

| Virus [a] | JEV [b, c] | TRIP [c, d]/ JEV.prME | TRIP [c, d]/ JEV.prME$^{\Delta TM}$ |
|---|---|---|---|
| JEV-G1/3 | 140 | 180 | 140 |
| JEV-G3/3 | 150 | 80 | 40 |
| JEV-G5/3 | 50 | 60 | 30 |

[a] Chimeric JEV G1/3 and G5/3 and parental JEV strain RP9 of G3 (G3/3).

[b] Antibody response of mice to inoculation of JEV strain RP9.

[c] FRNT50, the highest serum dilution that reduced the number of FFU of JEV by at least 50%.

[d] Antibody response of mice to inoculation of TRIP/JEV vector. Mice were inoculated i.p. twice with 5 log TU of TRIP/JEV vector at an interval of 1 month. Sera were collected 3 weeks after the boost.

TRIP/JEV.prME vector could elicit slightly higher levels of neutralizing anti-JEV antibodies when compared with TRIP/JEV.prME$^{\Delta TM}$. The lower neutralization capability of TRIP/JE-induced antibodies to chimeric JEV of G5/3 correlated well with their weak reactivity toward the E protein from JEV of G5 (FIG. 4B, right panel). These data show that TRIP/JEV vectors were capable of stimulating the production of JEV-neutralizing antibodies that worked well with the JEV of genotypes 1, 3, and to a lesser extent with G5.

Figure 5:
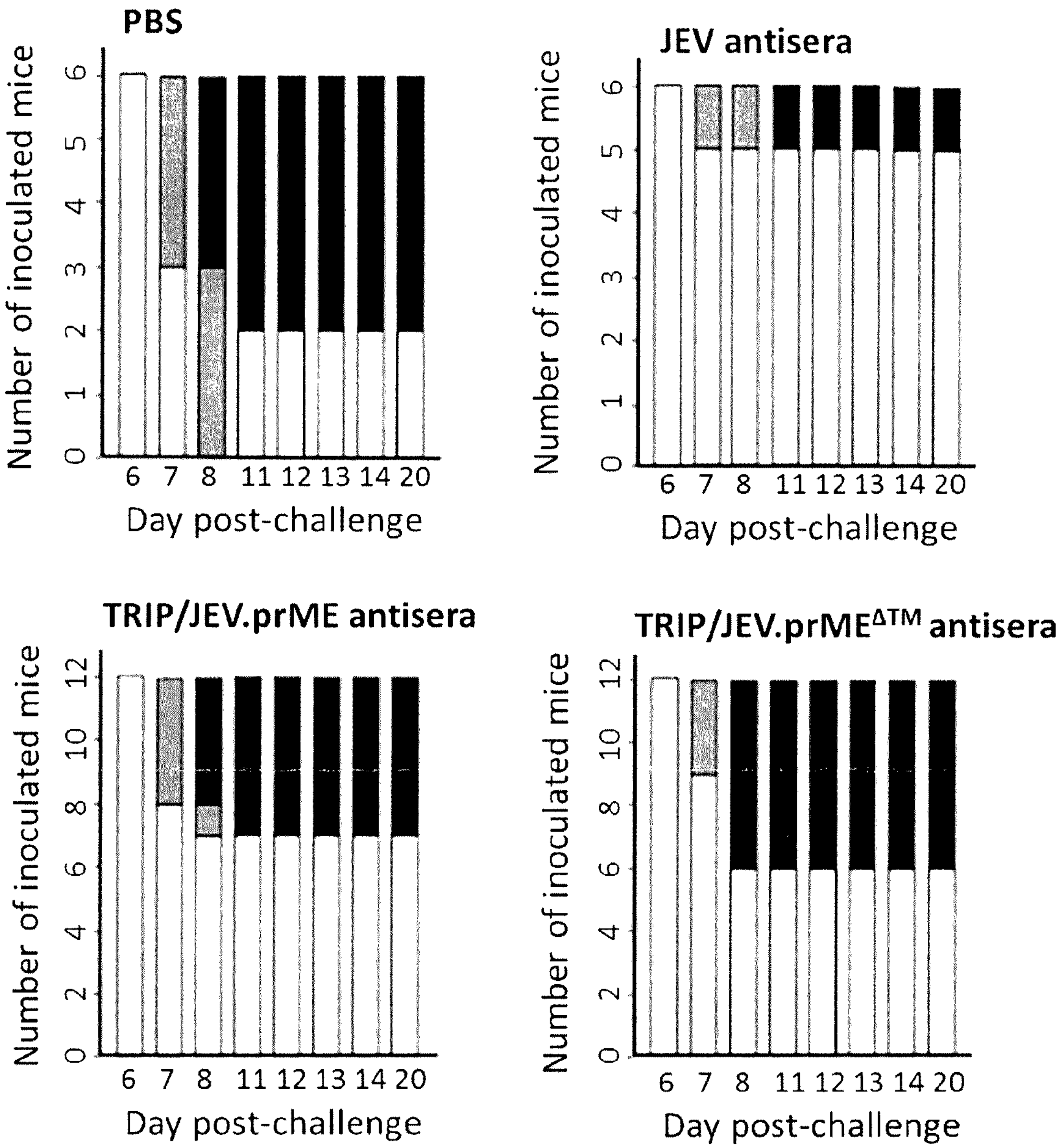
FIG. 5. In vivo protection after passive transfer of TRIP/JEV antisera. Groups of 3-week-old C56/Bl/6 mice received i.p. inoculations with 0.1 ml of DPBS containing 0.01 ml of pooled immune sera collected from JEV-infected mice (JEV G3 antisera) or TRIP/JEV-inoculated mice two months after boosting. Mice inoculated with DPBS (PBS) served as a group control. One day later, the mice were i.p. inoculated with 5 log 10 TU of JEV strain RP-9 and observed for mortality. Survival was recorded for 20 days. The grey boxes inform on the number of sick mice. The black boxes inform on the number of mice that did not survive to viral encephalitis.

In Vivo Protective Activity of JEV Antisera Elicited in Mice after TRIP/JEV Immunization Preliminary data showed that JEV strain RP9 infection of suckling C57Bl/6 mice was lethal within one week. Because the mouse susceptibility to RP9 quickly declines with age, the inventors were unable to challenge mice following the long prime-boost vaccination period with TRIP/JEV vectors. Consequently, the inventors decided to apply a protocol of passive transfer of TRIP/JEV antisera into suckling C57Bl/6 mice. To address whether the humoral immunity elicited in mice after TRIP/JEV.prME or TRIP/JEV.prME$^{\Delta TM}$ vaccination was protective in vivo, groups of twelve C57Bl/6 mice (3-week-old) received i.p. inoculation of 10 μl of pooled immune sera collected from TRIP/JEV-inoculated mice two months after boosting. Pooled immune sera of BALB/c mice inoculated with JEV strain RP-9 served as a positive control. A group of six mice inoculated with PBS was included. One day later the passive transfer of antisera, the mice were i.p. challenged with 5 $\log_{10}$ FFU of JEV strain RP-9. The animals were observed daily for clinical signs of illness and mortality over three weeks (FIG. 5).

Approximately 70% of the mice inoculated with PBS died within the 9-11 days post-challenge whereas administration of JEV immune sera induced a survival rate of 85%. Difference between the two control groups was statistically significant ($P<0.05$). Protective passive immunity was observed in C57Bl/6 mice after transfer of pooled sera from mice inoculated twice with TRIP/JEV.prME (survival rate of 60%) or TRIP/JEV.prME$^{\Delta TM}$ (survival rate of 50%). Differences between the two groups of mice receiving a single dose of TRIP/JEV immune sera and the PBS control group were statistically significant ($P<0.01$). These data show that a single dose of TRIP/JEV antisera confer partial protection in mice challenged with a lethal dose of JEV.

Seroneutralization

The neutralization activity of sera collected from surviving mice at 20 days post-inoculation was assayed using single-cycle reporter viral particles (RVPs). RVPs were produced in cells stably transformed with a JEV-RP9 (g3) subgenomic replicon expressing the viral nonstructural proteins and a *Renilla* luciferase reporter (FIG. 6A). Those cells were transfected with a plasmid that expresses either JEV g3 or JEV g5 structural proteins (C, prM and E), leading to successful release of RVPs (FIGS. 6C and 6D). Successful entry of the recombinant RVPs into new target cells leads to genome release and subsequent expression of a luciferase reporter gene. Such system has been shown to be sensitive and potent to use in seroneutralization assays (Dowd K A, et al. Jost C A, Durbin A P, Whitehead S S, Pierson T C. 2011. *PLoS Pathog.* 7:e1002111). Interestingly, the inventors showed that sera from BALB/c mice surviving JEV g3 infection potently neutralized both JEV g3 and g5 RVPs (FIG. 7, left). In a reciprocal assay, sera from BALB/c mice surviving JEV g5 infection had very potent neutralization activity against JEV g5 RVPs, but poor neutralization against JEV g3 RVPs (FIG. 7, right).

Seroneutralization Assay:

Sera samples were obtained from 3-week-old BALB/c mice at 20 days post-inoculation with 1000 ffu of JEV-RP9 (g3) or JEV-XZ0934 (g5). The sera were decomplemented by heating at 56° C. for 30 min and were two-fold serial diluted in DMEM supplemented with 2% FBS, with a starting dilution of 1:10. Each dilution was incubated for 1 h at 37° C. with an equal volume of purified g3 or g5 RVP. Remaining RVP infectivity was assayed on BHK cells seeded in a 96-well plate, as described above.

TRIP/JEV.prME Induced the Production of Neutralizing Anti-JEV Antibodies in Pigs Because lentiviral based-expression of JEV VLPs is particularly efficient at triggering neutralizing antibody responses, the inventors assessed the capacity of TRIP/JEV.prME to stimulate a protective humoral response in pigs. Groups of four 7-week-old piglets were immunized intramuscularly with 6 (low dose) or 7 (high dose) $\log_{10}$ TU of TRIP/JEV.prME (FIG. 8). As a control, two animals received a low or high dose of a recombinant lentiviral vector expressing reporter GFP. Indirect ELISA using recombinant EΔTM-SNAP protein as a viral antigen was used to assess the production of anti-JEV E antibodies in immunized pigs weekly (FIG. 8A). The monitoring of the antibody responses during the first 4 weeks after the prime inoculation revealed an efficient production of anti-JEV E antibodies. Comparison of the low and high dose immunization did not show statistically significant differences in anti-JEV E antibody production over this time period. The levels of anti-JEV E antibodies was enhanced after the boost performed on week 4, and reached a plateau at least 1.5 month after the prime. When compared to the low dose, the high dose of TRIP/JEV.prME was more effective at eliciting a high level of specific antibody production ($P=0.028$). As shown in the FIG. 8B, the anti-JEV antibody titers induced 3 weeks after experimental infection of pigs with a single dose of live JEV were comparable to those stimulated in animals by a prime/boost immunization with 7 $log_{10}$ TU of TRIP/JEV.prME lentiviral vector.

The isotyping of anti-JEV E antibodies showed that TRIP/JEV.prME stimulated the production of both IgG1 and IgG2 by 2 weeks after the prime, and was followed by a decline at week 3 even at the high dose (FIGS. 8C and 8D). The levels of both anti-JEV E IgG1 and IgG2 were similar to those observed in piglets challenged with JEV strain Nakayama at the week 3 of infection (FIG. 8E). In animals primed with TRIP/JEV.prME, the boost at week 4 enhanced preferentially the production of IgG2 by 10 weeks after the prime regardless of the inoculated dose.

The individual serum samples obtained from animals immunized with the lentiviral TRIP/JEV.prME vector were also examined for neutralizing antibodies at 3 weeks after the prime and at 6 weeks after the boost (FIG. 9). Immunized piglets that received a single dose of 6 to 7 $log_{10}$ TU of TRIP/JEV.prME developed neutralizing antibody titers ranging from 10 to 30 against the homologous JEV G3 strain RP-9 and reached titers up to 160 after the boost (FIG. 9A). The higher dose of TRIP/JEV.prME induced a stronger anamnestic neutralizing antibody response.

Examination of the piglet immune sera revealed that, regardless of the inoculated dose, TRIP/JEV.prME elicited neutralizing antibodies against the Nakayama strain of JEV G3, the strain XZ0934 (tested using the JEV G5/G3 chimera) of JEV G5 and, to a lesser extent, the strain CNS769_Laos_2009 of JEV G1 (FIG. 9B). Importantly, the pattern of neutralizing activity of anti-TRIP/JEV.prME antibody was similar to that observed in immune sera collected from a group of piglets experimentally infected with the JEV strain Nakayama (FIG. 9C).

These results showed that TRIP/JEV.prME was able to elicit high titers of neutralizing antibodies in piglets that received two inoculations with 7 $log_{10}$ TU of lentiviral vector with an interval of one month. Additionally, the inventors found that TRIP/JEV.prME was capable of stimulating the production of anti-JEV antibodies that neutralized JEV G1 and G5.

DISCUSSION

The VSV-G-pseudotyped lentiviral vectors are notably well suited for vaccine purposes with the efficient delivery of viral antigens in both dividing and non-dividing cells such as dendritic cells leading to activation of robust adaptive immunity in humans and animals (Hu et al., 2011). Direct injection of lentiviral TRIP-based vectors results in efficient viral antigen expression and antibody responses. The inventors reported that lentiviral TRIP-based vector coding for the envelope E glycoprotein from WNV can prime antibody-based responses conferring long-term immune protection against WNV encephalitis in mouse model (Coutant et al., 2008; Iglesias et al., 2006). The objective of the current study was to evaluate two lentiviral TRIP-based vectors expressing prM and E proteins from JEV, TRIP/JEV.prME vector and TRIP/JEV.prME$^{\Delta TM}$ vector, for their ability to elicit protective humoral immune response in mice and piglets. In these constructs, prM does play the role of chaperone of E and both have the capacity to self-assemble into VLPs. Co-expression of recombinant JEV prM and E resulted in extracellular secretion of VLPs in human cells transduced with TRIP/JEV.prME vector. As TRIP/JEV.prME$^{\Delta TM}$ vector could not secret JEV VLPs, the inventors inferred that E protein without its transmembrane domains could favor the retention of prM into the intracellular compartment impairing the production of VLPs.

The antibody-based immune response plays an essential role in vaccines against JEV and the E protein acts as the main target for imparting protective immunity against JEV-related disease (Erra et al., 2013; Konishi). Mice inoculated with a single low dose (5 $log_{10}$ TU) of TRIP/JEV vectors had significant levels of JEV-specific IgGs and a booster dose one month after the prime resulted in a 40-fold increase in anti-JEV antibody titers. The reactivity of anti-JEV antibodies was documented in indirect ELISA and immunoblot assays using different JEV antigens and chimeric JEV. Mice immunized with TRIP/JEV.prME vector but not TRIP/JEV.prME$^{\Delta TM}$ vector developed specific anti-prM antibodies. Such result could be related to the ability of TRIP/JEV.prME vector to produce extracellular JEV VLPs. Analysis of recognition of JEV antigens by TRIP/JEV antisera showed that immunization with the two TRIP/JEV vectors generated comparable levels of antibodies against the E proteins as well as type-specific epitopes located in its antigenic domain III (EDIII) from JEV of G1, G3, and G5. Given that EDIII contains several neutralizing epitopes and host cell receptor recognition sites for flaviviruses (Samuel et al. 2006), the results of the inventors confirm that recombinant E protein with or without its C-terminal region has essentially preserved immunogenicity of native E protein. Neutralization assays demonstrated that TRIP/JEV vectors could elicit neutralizing antibodies against JEV of G1, G3, and G5 as live JEV of G3 do. In vivo, a single dose of 10 μl of TRIP/JEV antisera was able to confer a partial protection against a lethal challenge with JEV of G3. However, TRIP/JEV.prME was slightly more efficient in the production of neutralizing anti-JEV antibodies than TRIP/JEV.prME$^{\Delta TM}$.

The fact that TRIP/JEV vectors could efficiently develop neutralization antibodies suggest that both TRIP/JEV.prME and TRIP/JEV.prME$^{\Delta TM}$ might be capable to stimulate protective humoral responses against different genotypes of JEV showing their utility in endemic regions where more than one genotype cocirculate. Even if it is widely accepted that humoral immune response is an essential component of protective immunity against JEV infection, the inventors cannot rule out that cellular immunity also plays a role in the establishment of long-term protection against JEV.

Both TRIP/JEV.prME and TRIP/JEV.prME$^{\Delta TM}$ appear as promising JEV vaccines for veterinary vaccination against different JEV genotypes. One of the marked advantage of JEV VLPs is their efficiency to stimulate long-lasting antibody-mediated immunity.

In conclusion, the objective of this study was to evaluate two lentiviral TRIP-based vectors expressing envelope prM and E glycoproteins from JEV of genotype 3, TRIP/JEV.prME vector and TRIP/JEV.prME$^{\Delta TM}$ vector, for their ability to induce protective humoral response in mice and piglets.

Transduction of 293T cells showed that TRIP/JEV.prME vector was efficient in the secretion of Virus-Like Particles (VLPs) which are assembled from prM and E whereas TRIP/JEV.prME$^{\Delta TM}$ vector only secreted the soluble form of E lacking from its two transmembrane domains. Mice inoculated with one dose of each TRIP/JEV vector had significant levels of JEV-specific IgGs and a booster dose one month after the prime resulted in a significant increase in anti-JEV antibody titers. The prime boost of mice with TRIP/JEV vectors elicited comparable levels of total antibodies against the E protein as well as type-specific epitopes from JEV of genotypes 1, 3, and 5.

Neutralization assays showed that TRIP/JEV.prME was slightly more efficient in the production of neutralizing anti-JEV antibodies than TRIP/JEV.prME$^{\Delta TM}$. By using chimeric JEV which contain prM and E from JEV of genotype 1 or 5 into the backbone of genotype 3, the inventors demonstrated that TRIP/JEV vectors could elicit neutralizing antibodies against JEV regardless the genotype. Passive seroprotection assay showed that a single dose of TRIP/JEV antisera confer partial protection in mice challenged with a lethal dose of JEV. Thus, both TRIP/JEV.prME and TRIP/JEV.prME$^{\Delta TM}$ appear as promising JEV vaccines for veterinary vaccination against different JEV genotypes showing their great utility in endemic regions.

It is widely accepted that the humoral immune response is an essential component of protective immunity against JEV infection (Dubischar-Kastner et al., 2012; Larena et al., 2013). Consistent with the notion that VLPs are suitable as vaccine against arboviral disease including Japanese encephalitis (Kuwahara et al., 2010; Piljman et al., 2015), TRIP/JEV. prME was the more efficient lentiviral vector in the production of neutralizing anti-JEV antibodies that conferred partial protection after their passive transfer in mice challenged with JEV. Inoculation of two doses of 7 $\log_{10}$ TU with a one-month of interval of TRIP/JEV.prME vector in piglets was highly efficient at eliciting high titers of anti-JEV neutralizing antibody that are potentially able to protect pigs from JEV infection. TRIP/JEV.prME was capable of stimulating the production of anti-JEV antibodies that neutralize JEV G3 and G5, and, to a lesser extent, G1. The potential impact of JEV genotype change on vaccine potency has been estimated and immune sera obtained from pigs injected with a G3 vaccine showed lower strain-specific cross-neutralizing antibody titers against JEV of G1 (Fan et al. 2012). Such observation led to the development of new veterinary vaccines for pigs specifically directed against this particular genotype of JEV (Yang et al., 2014). Although the TRIP/JEV.prME vector elicited neutralizing antibodies against a G1 virus in pigs, the inventors did note that their levels were lower when compared to the other JEV genotypes tested. However, neutralizing antibodies titers against JEV of G1 could reach 1:40, and thus could be sufficient to achieve protection in pigs.

In this study, the inventors demonstrated that immunization of pigs with a TRIP/JEV vector expressing JEV VLPs was particularly efficient at priming antigen-specific humoral immunity and triggered neutralizing antibody responses against the genotypes 1, 3, and 5 of JEV. The production of virus neutralizing antibodies was critical to protection against JEV infection in pigs (Imoto et al., 2010) and a titer at least 1:10 was indicative of protective humoral immunity (Van Gessel et al. 2011). The titers of neutralizing antibodies elicited by the lentiviral TRIP/JEV.prME vector were sufficient to confer protection in domestic pigs against different genotypes of JEV and this could be of a great utility in endemic regions where more than one genotype circulates.

BIBLIOGRAPHY

Aubry F, et al. (2013), Genome Announc. 2013 pii: e00157-12.
Beignon A S, et al. (2009), J. Virol. 83: 10963-74.
Bonaparte M, et al. (2014), BMC Infect Dis. 214:156.
Campbell G L, et al. (2011), Bull World Health Organ. 89: 766-74.
Chen L K, et al. (1996), Virology 223:79-98.
Coutant F, et al. (2008), PLoS ONE 3: e3973.
de Wispelaere et al. (2015), J. Virol. 89: 5862-5875.
de Wispelaere et al. (2015), PLOS Negl. Trop. Dis. 9(10).
Di Nunzio F, et al. (2012), Vaccine 30: 2499-509.
Dubischar-Kastner K, Kanesa-Thasan N. (2012), Expert Rev Vaccines. 11:1159-61.
Erra E O, et al. (2013), Clin Infect Dis. 56:267-70.
Fan Y C, et al. (2012), PLoS Negl Trop Dis. 6:e1834.
Fan Y C, et al. (2013), Vet. Microbiol. 163:248-56.
Firat H. et al. (2002), J. Gene Med. 4(1):38-45.
Fontana J M, et al. (2014), PLoS ONE 9(5):e97270.
Gao X, et al. (2013), PLoS Negl Trop Dis.: e2459.
Go Y Y, Balasuriya U B, Lee C K. (2014), Clin Exp Vaccine Res. 3:58-77.
Grasso F, et al. (2013), Int. J. Cancer 132:335-44.
Halstead S B, Thomas S J. (2011), Expert Rev Vaccines. 10:355-64.
Hu B, Tai A, Wang P. (2011), Immunol. rev. 239: 45-61.
Hubálek Z, Rudolf I, Nowotny N. (2014), Adv Virus Res. 89:201-75.
Iglesias M C., et al. (2006), J. Gene Med. 8: 265-74.
Imoto et al. (2010), Vaccine, 28: 7373-7380.
Impoinvil D E, Baylis M, Solomon T. (2013), Curr Top Microbiol Immunol. 365:205-47.
Ishikawa T, Yamanaka A, Konishi E. (2014), Vaccine 32:1326-3.
Katoh et al. (2011), J. Virol., 85(21):10976-88.
Kaur et al. (2002), J. Infect. Dis. 185: 1-12.
Konishi E. (2013), Expert Rev Vaccines 12:871-3.
Kuwahara M, Konishi E. (2010), Clin Vaccine Immunol. 17:875-8.
Larena M, et al. (2013), J Virol. 87:4395-402.
Le Flohic G, et al. (2013), PLoS Negl Trop Dis. 7:e2208.
Li J, et al. (2013), Vaccine. 2013 31:4136-42.
Li M H, et al. (2011), PLoS Negl Trop Dis. 5:e1231.
Li M H, et al. (2014), China. Biomed Environ Sci. 27:231-9.
Liang et al. (2009), Vaccine, 27(21):2746-54.
Marks F, et al. (2012), PLoS Negl Trop Dis. 6:e1952.
Pan X L, et al. (2011), J. Virol. 85:9847-53.
Piljman et al. (2015), Biotechnol. J. 10(5), 659-670.
Sakuma T, Barry M, Ikeda Y. (2012), Biochem. J. 443: 603-618.
Samuel et al. (2006), J. Virol., 9349-9360.
Schuh A J, et al. (2013), PLoS Negl Trop Dis. 7:e2411.
Schuh A J, et al. (2014), J Virol. 88:4522-32.
Solomon T, et al. (2003). J Virol. 77:3091-8.
Song B H, et al. (2012), J Microbiol. 50:698-706.
Takhampunya R, et al. (2011), Virol J. 2011 8:449.
VandenDriessche T. et al. (2002), Blood, 100(3):813-822.
Van Gessel et al. (2011), Vaccine, 29, 5929-5933.
Weaver S C, Barrett A D. (2004), Nat Rev Microbiol. 2: 789-801.
Yang D, et al. (2014), Vaccine 32:2675-81.
Yun S I, Lee Y M. (2014), Hum Vaccin Immunother. 10:263-279.
Zu X, et al. (2014), Antiviral Res. 104:7-14.
Zeller, H. (2012), Euro Surveill. 17:pii=20242.
Zennou V, et al. (2000), Cell 101:173-85.

The invention claimed is:

1. A method of prophylactically treating against JEV infection in a mammal, comprising administering recombinant lentiviral vector particles expressing a recombinant lentiviral vector genome to the mammal, wherein the recombinant lentiviral vector particles are able to elicit a protective immune response against genotypes 1, 3, and 5 of JEV that is conferred within about one week after a prime/boost administration of the composition;

(i) wherein said recombinant lentiviral vector genome comprises lentiviral cis-active elements including long terminal repeats (LTRs) or modified LTRs including partially deleted 3'LTR, psi (w) packaging signal, Rev responsive element (RRE) and DNA flap central polypurine tract (cPPT)/central termination sequence (CTS), together with a transcription unit encoding the precursor of membrane (prM) of SEQ ID NO: 6, and the envelope (E) protein of a Japanese encephalitis virus (JEV), wherein the E protein is either the full-length E protein of SEQ ID NO: 9, or its soluble form of SEQ ID NO: 12;

(ii) wherein said particles are pseudotyped with a vesicular stomatitis virus glycoprotein G (VSV-G) protein; and (iii) wherein said transcription unit encodes the amino acid sequence of SEQ ID NO: 3.

2. The method according to claim 1, wherein in the lentiviral 3'-LTR the promoter and the activator of the U3 region have been deleted, and wherein the polynucleotide encoding the prM and E proteins is placed under the control of a heterologous promoter.

3. The method according to claim 2, wherein the heterologous promoter is the cytomegalovirus immediate early (CMVie) promoter.

4. The method according to claim 1, wherein the polynucleotide encoding the prM protein has the sequence of SEQ ID NO: 5, the polynucleotide encoding the full-length E protein has the sequence of SEQ ID NO: 8 and the polynucleotide encoding the soluble form of the E protein has the sequence of SEQ ID NO: 11.

5. The method according to claim 1, wherein the lentiviral vector genome is derived from the genome of HIV.

6. The method according to claim 5, wherein the genome of HIV is of HIV-1.

7. The method according to claim 1, wherein the lentiviral vector genome is derived from the genome of FIV.

8. The method according to claim 1, wherein the lentiviral vector genome is replication-incompetent as a result of deletion of all or part of the gag and pol genes of the lentiviral genome or mutation in the gag and pol genes of the lentiviral genome, so that the gag and pol genes are not capable of encoding functional GAG and POL proteins.

9. The method according to claim 1, wherein the mammal is a pig or a piglet.

10. The method according to claim 1, wherein the lentiviral vector particles are integration defective as a result of mutation or deletion in the pol gene of the lentivirus.

11. The method according to claim 1, wherein the lentiviral vector particles are administered at a dose sufficient to elicit a protective antibody response against JEV prM and/or E protein(s).

12. The method according to claim 1, wherein the method comprises administering said recombinant lentiviral vector particles in a prime-boost regimen.

13. The method according to claim 12, wherein the lentiviral vector particles for priming the immunological response and the lentiviral vector particles for boosting the response are pseudotyped with different non-cross reacting VSV-G envelope proteins.

14. The method according to claim 1, wherein the JEV is a JEV of a genotype selected from G1, G3 and G5.

15. The method according to claim 1, wherein the JEV is a JEV of genotype G3.

16. The method according to claim 15, wherein the JEV is a JEV of the strain RP-9 or a JEV of the strain Nakayama.

17. The method according to claim 1, wherein said particles are in admixture with a pharmaceutically acceptable vehicle, and/or an adjuvant.

* * * * *